United States Patent
Wang et al.

(10) Patent No.: US 9,822,154 B2
(45) Date of Patent: Nov. 21, 2017

(54) IMMUNE MODULATOR FOR IMMUNOTHERAPY AND VACCINE FORMULATION

(71) Applicants: VIRGINIA COMMONWEALTH UNIVERSITY, Richmond, VA (US); HEALTH RESEARCH, INC., Buffalo, NY (US)

(72) Inventors: Xiang-Yang Wang, Richmond, VA (US); Xiaofei Yu, Richmond, VA (US); John R. Subjeck, Buffalo, NY (US)

(73) Assignees: VIRGINIA COMMONWEALTH UNIVERSITY, Richmond, VA (US); HEALTH RESEARCH, INC., Buffalo, NY (US)

( * ) Notice: Subject to any disclaimer, the term of this patent is extended or adjusted under 35 U.S.C. 154(b) by 69 days.

(21) Appl. No.: 14/652,078

(22) PCT Filed: Dec. 14, 2013

(86) PCT No.: PCT/US2013/075210
§ 371 (c)(1),
(2) Date: Jun. 12, 2015

(87) PCT Pub. No.: WO2014/093950
PCT Pub. Date: Jun. 19, 2014

(65) Prior Publication Data
US 2015/0315255 A1    Nov. 5, 2015

Related U.S. Application Data

(60) Provisional application No. 61/737,443, filed on Dec. 14, 2012.

(51) Int. Cl.
| | | |
|---|---|---|
| C12N 15/00 | (2006.01) |
| A61K 39/00 | (2006.01) |
| C07K 14/47 | (2006.01) |
| C12N 5/0783 | (2010.01) |
| A61K 39/112 | (2006.01) |
| A61K 35/17 | (2015.01) |
| C07K 14/255 | (2006.01) |
| A61K 35/761 | (2015.01) |

(52) U.S. Cl.
CPC .......... *C07K 14/47* (2013.01); *A61K 35/17* (2013.01); *A61K 35/761* (2013.01); *A61K 39/0011* (2013.01); *A61K 39/0275* (2013.01); *C07K 14/255* (2013.01); *C12N 5/0636* (2013.01); *A61K 2039/57* (2013.01); *A61K 2039/572* (2013.01); *A61K 2039/585* (2013.01); *A61K 2039/6068* (2013.01); *A61K 2039/70* (2013.01); *C07K 2319/00* (2013.01); *C07K 2319/40* (2013.01); *C12N 2710/10343* (2013.01); *C12Y 306/03044* (2013.01)

(58) Field of Classification Search
None
See application file for complete search history.

(56) References Cited

U.S. PATENT DOCUMENTS

| | | |
|---|---|---|
| 6,984,384 B1 | 1/2006 | Subjeck et al. |
| 7,378,096 B2 | 5/2008 | Subjeck et al. |
| 7,976,846 B2 | 7/2011 | Subjeck et al. |
| 8,080,388 B2 | 12/2011 | Subjeck et al. |
| 2008/0293103 A1 | 11/2008 | Subjeck et al. |
| 2012/0135037 A1 | 5/2012 | Mizel et al. |

FOREIGN PATENT DOCUMENTS

WO    WO9706821    2/1997

OTHER PUBLICATIONS

Cuadros, Camilo et al., "FLagellin fusion proteins as adjuvants or vaccines induce specific immune responses", Infection and Immunity, May 2004, vol. 72, No. 5, pp. 2810-2816.
Database UniProtKB/Swiss-Prot, P06179 (FlIC_SALTY), Jan. 23, 2007.
Lanson, Nicolas A. Jr. et al., "Replication of an Adenoviral Vector Controlled by the Human Telomerase Reverse Transcriptase Promoter Causes Tumor-Selective Tumor Lysis", Cancer Research, 2003, No. 63, pp. 7936-4179.
Jun-Eui et al., "Chaperoning function of stress protein grp 170, a member of the hsp70 superfamily, is responsible for its immunoadjuvant activity", Cancer Research, 2006, vol. 66, No. 2, pp. 1161-1168.
Wang, Xiang-Yang et al., "Characterization of Heat Shock Protein 110 and Glucose-Regulated Protein 170 as Cancer Vaccines and the Effect of Fever-Range Hyperthermia on Vaccine Activity", The Journal of Immunology, 2001, 165: pp. 490-497.
International Search Report and Written Opinion from Corresponding international application PCT/US13/75210 (WO2014093950), Dated Apr. 24, 2014.

*Primary Examiner* — Jennifer Graser
(74) *Attorney, Agent, or Firm* — Karen S. Canady; Canady & Lortz LLP

(57) ABSTRACT

A recombinant Flagrp170 protein and pharmaceutical compositions comprising a Flagrp170 protein and related molecules encoding same, and cells presenting such a protein are provided. The Flagrp170 protein comprises an NF-$_\kappa$B-activating domain of Flagellin and an ATP-binding domain truncated Grp170. The pharmaceutical compositions of the invention can be used for the treatment or prevention of cancer or infectious disease.

5 Claims, 23 Drawing Sheets

FIGS. 6C-6D
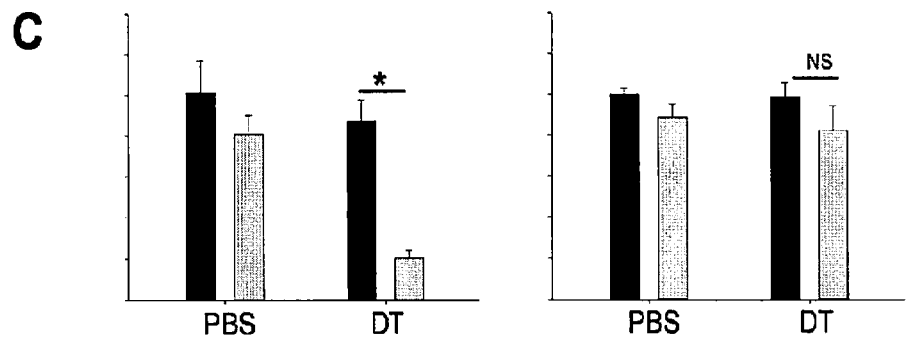
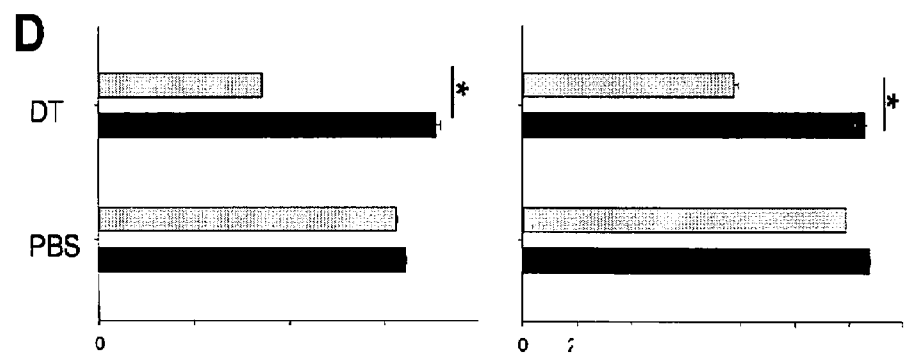
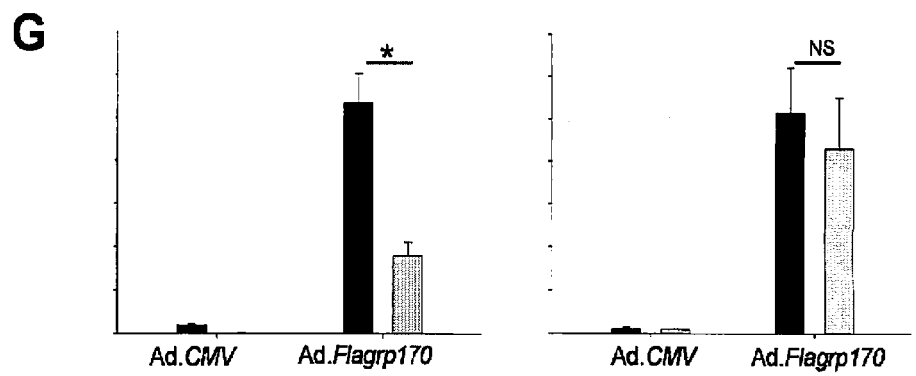
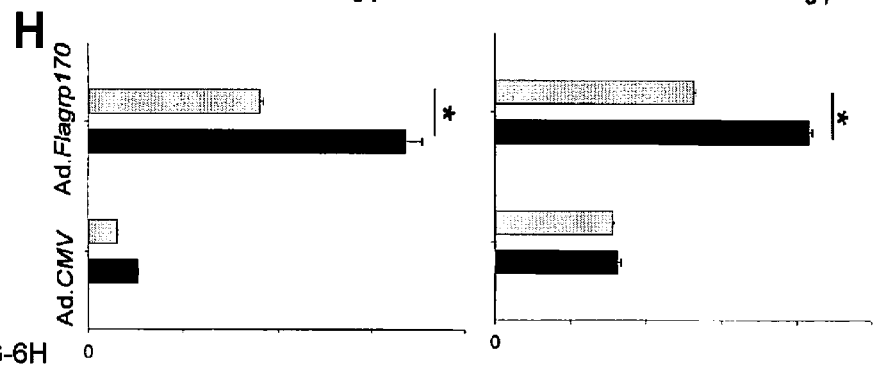
FIGS. 6G-6H

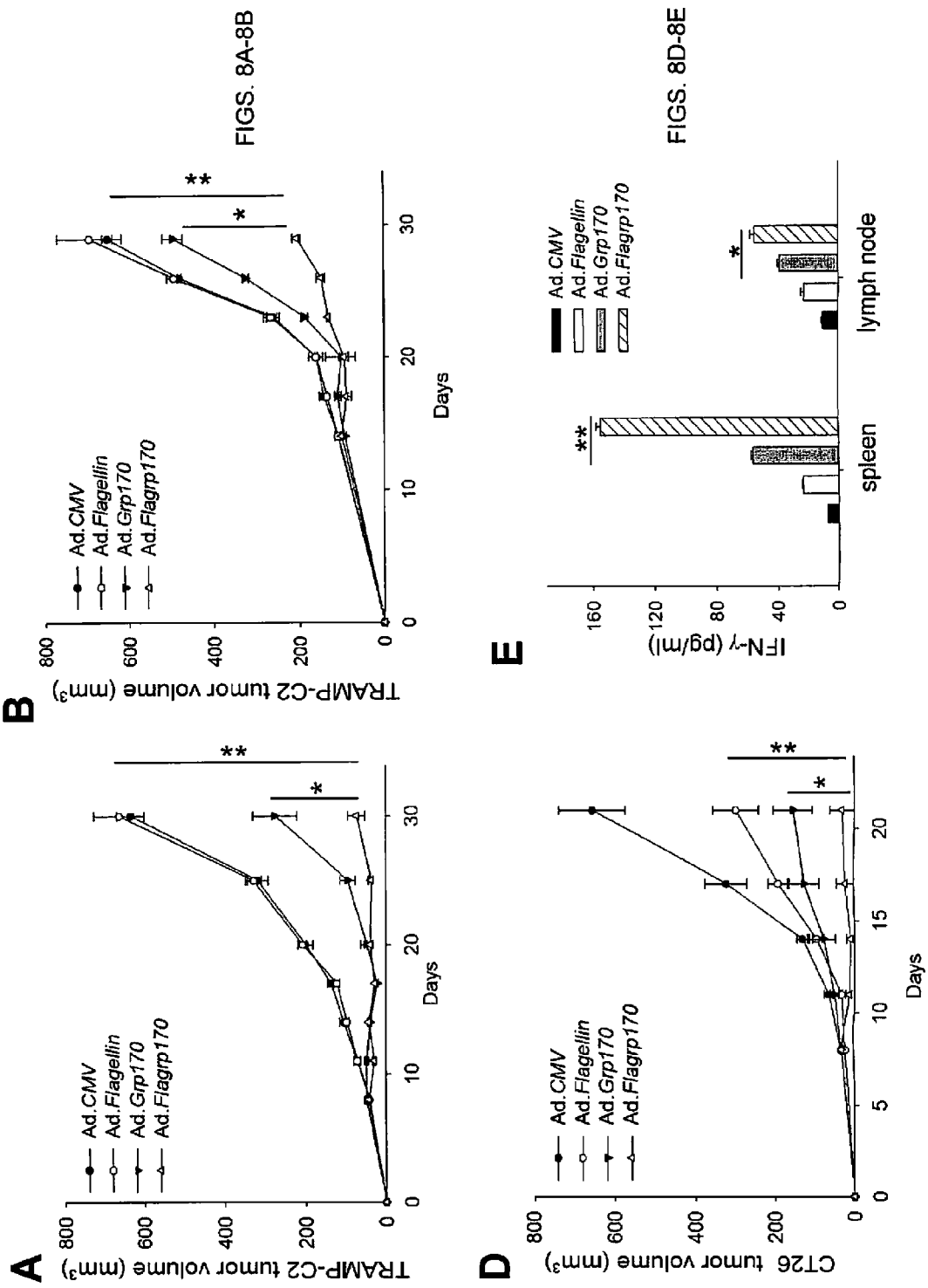

FIG. 8C
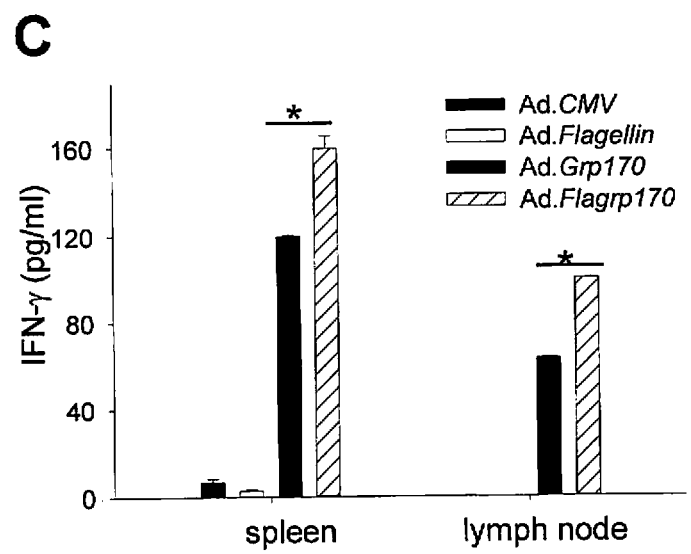
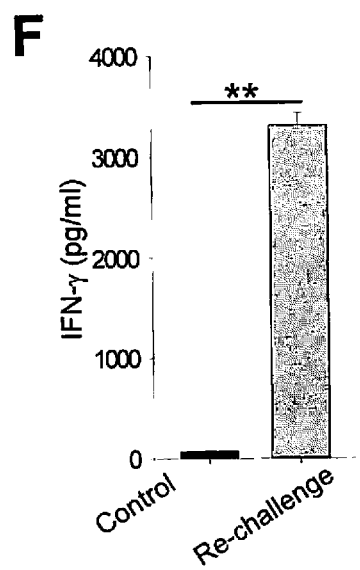
FIG. 8F

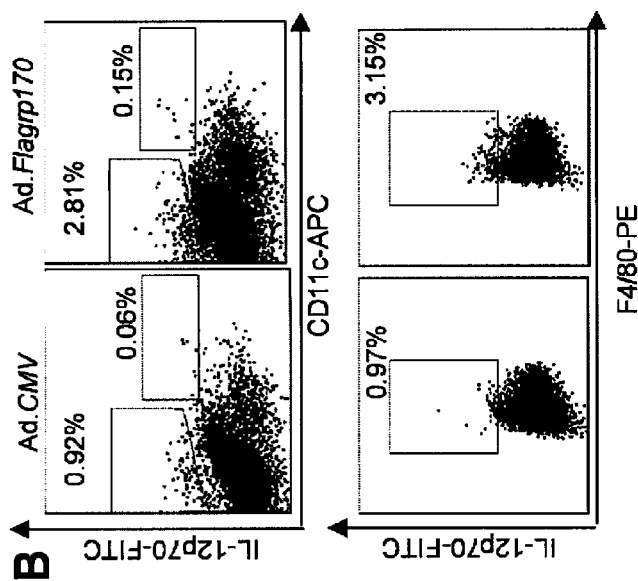
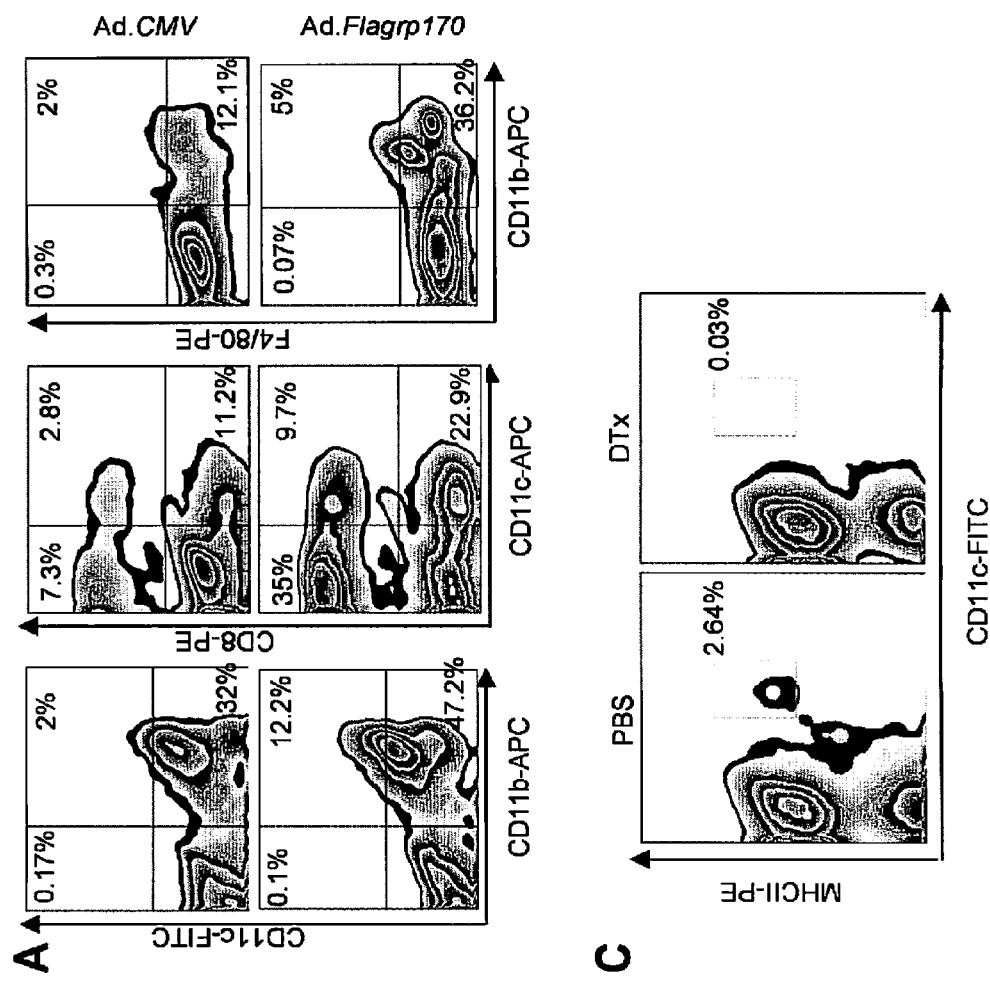
FIGS. 12A-12C

IMMUNE MODULATOR FOR IMMUNOTHERAPY AND VACCINE FORMULATION

This application is the National Stage of International Application No. PCT/US2013/075210, filed Dec. 14, 2013, which claims benefit of U.S. provisional patent application Ser. No. 61/737,443, filed Dec. 14, 2012, the entire contents of which are hereby incorporated herein by reference. Throughout this application various publications are referenced. The disclosures of these publications in their entireties are hereby incorporated by reference into this application in order to describe more fully the state of the art to which this invention pertains.

STATEMENT REGARDING FEDERALLY SPONSORED RESEARCH

This invention was made with U.S. government support under grant numbers CA129111 and CA154708 awarded by the National Institutes of Health. The U.S. government has certain rights in this invention.

TECHNICAL FIELD

The present invention relates generally to prevention and therapy of cancer and infectious disease. The invention is more specifically related to polypeptides comprising a portion of glucose-regulated protein 170 (Grp170) fused with the TLR5-activating domain of Flagellin, a major structural protein of the bacterial flagella, to form a secretable Grp170-Flagellin hybrid chaperone (Flagrp170), and to polynucleotides encoding such polypeptides. Such polypeptides, polynucleotides and related products may be used in vaccines and pharmaceutical compositions for the prevention and treatment of cancers and infectious diseases.

BACKGROUND OF THE INVENTION

Cancer and infectious disease are significant health problems throughout the world. Although advances have been made in detection and therapy of these diseases, no vaccine or other universally successful method for prevention or treatment is currently available. Current therapies, which are generally based on a combination of chemotherapy or surgery and radiation, continue to prove inadequate in many patients.

Molecular chaperones are essential for maintaining cellular functions by assisting protein folding and translocation, or by preventing protein misfolding and aggregation. Studies over the last two decades support the concept of intracellular chaperone molecules as carriers of the antigenic repertoire of cancer cells, which is attributed to their intrinsic property to interact with polypeptide chains. Autologous tumor-derived, chaperone-peptide complex preparations, therefore, provide an innovative immunotherapeutic approach to treatment of cancers. However, only limited improvement in the clinical outcome has been achieved using this approach.

In spite of considerable research into therapies for infectious disease and cancer, these diseases remain difficult to diagnose and treat effectively. Accordingly, there is a need in the art for improved methods for treating cancer and infectious disease. The present invention fulfills these needs and further provides other related advantages.

SUMMARY OF THE INVENTION

The invention provides a Flagrp170 protein or polynucleotide encoding same. The Flagrp170 protein comprises an NF-κB-activating domain of Flagellin and a truncated Grp170. The invention also provides a fusion construct comprising a polynucleotide encoding an NF-κ-activating domain of Flagellin in operable linkage with a polynucleotide encoding a truncated Grp170, and vectors comprising such constructs. Also provided is a pharmaceutical composition and/or an immunogenic composition comprising a polypeptide or fusion construct of the invention, and, optionally, a pharmaceutically acceptable carrier, further antigen or immunogenic molecule, and/or an adjuvant.

In one embodiment, the NF-κB-activating domain of Flagellin comprises N-terminal amino acids 2-175 and C-terminal amino acids 402-495 of SEQ ID NO: 8 (GenBank accession #AAL20871.1). In one embodiment, the polynucleotides encoding the N-terminal amino acids 2-175 and C-terminal amino acids 402-495 of SEQ ID NO: 8 are joined by a flexible linker. The polynucleotide encoding the NF-κB-activating domain of Flagellin and the polynucleotide encoding an ATP-binding domain truncated Grp170 can also be joined by a flexible linker.

In a typical embodiment, the Flagellin is from *Salmonella enterica* serovar *Typhimurium* LT2. In one embodiment, the Flagellin has the amino acid sequence shown in SEQ ID NO: 9. In some embodiments, the Flagellin has an amino acid sequence that is at least 90% identical to that shown in SEQ ID NO: 9, over the entire length of SEQ ID NO: 9. In some embodiments, the Flagellin amino acid sequence is at least 95% identical to the full length of SEQ ID NO: 9. In one embodiment, the Flagellin amino acid sequence differs from that of SEQ ID NO: 9 by no more than 5 amino acids.

In one embodiment, the truncated Grp170 comprises the ATP-binding domain truncated Grp170, e.g., amino acids 431-994 of SEQ ID NO: 2. In some embodiments, the truncated Grp170 is modified by deletion of the 'KNDEL' ER retention sequence (amino acids 995-999 of SEQ ID NO: 2) of Grp170. The Grp170 can be a murine, a human, or another mammalian Grp170. In a typical embodiment, the Grp170 has the amino acid sequence shown in SEQ ID NO: 2 or 3. In some embodiments, the Grp170 has an amino acid sequence that is at least 90% identical to that shown in SEQ ID NO: 2 or 3, over the entire length of SEQ ID NO: 2 or 3. In some embodiments, the Grp170 amino acid sequence is at least 95% identical to the full length of SEQ ID NO: 2 or 3. In one embodiment, the Grp170 amino acid sequence differs from that of SEQ ID NO: 2 or 3 by no more than 5 amino acids.

The fusion construct optionally further comprises a polynucleotide encoding a signal or leader peptide operably linked to the N-terminus of the fusion construct. Examples of a signal or leader peptide include, but are not limited to, the 34-amino acid leader peptide of Grp170. In some embodiments, the fusion construct further comprises a sequence encoding a selectable marker. Examples of selectable markers include, but are not limited to, a His tag or a GST tag.

Also provided is a vector comprising the fusion construct described herein. The vector can include elements that facilitate expression of the fusion protein, such as promoters and other expression control sequences. One example of a promoter suitable for use with the invention is a cytomegalovirus (CMV) promoter. The vector can be, for example, an adenovirus. Other suitable vectors include, but are not limited to, adeno-associated virus, retrovirus (e.g., lentivirus), vaccinia or other pox virus (e.g., other mammalian pox virus or avian pox virus, such as Fowlpox), Herpes simplex virus, or vesicular stomatitis virus.

In another embodiment, a vector comprises a cancer-specific promoter controlling viral replication employed together with a fusion construct of the invention, as described in Example 3 below. In one embodiment, the cancer-specific promoter is human telomerase reverse transcriptase (hTERT), such as that described at Accession No. BAC11010.

The invention additionally provides a recombinant host cell comprising an expression vector that includes the fusion construct of the invention under the control of a promoter or other expression control sequence, such as a CMV promoter. Suitable host cells can be selected by those skilled in the art, and are those in which the vector will be capable of functioning as desired.

The invention further provides a method of producing a fusion protein comprising culturing a recombinant host cell transduced with an expression vector of the invention under conditions suitable for production of the protein encoded by the fusion construct, and recovering the protein so produced. Also provided is a polypeptide produced by the method.

In some embodiments, the Flagrp170 polypeptide is additionally complexed with an immunogenic polypeptide, for example, by non-covalent interaction or by covalent interaction, including a fusion protein. The immunogenic polypeptide complexed with the Flagrp170 protein can be associated with a cancer or an infectious disease. In some embodiments, the immunogenic polypeptide is known. Where the immunogenic polypeptide is a known molecule, the immunogenic polypeptide can be provided in admixture with the Flagrp170 polypeptide, or as a complex with the Flagrp170 polypeptide. The Flagrp170 polypeptide can be complexed with the immunogenic polypeptide by non-covalent binding. Alternatively, the complex can comprise a fusion protein, wherein the stress polypeptide is linked to the immunogenic polypeptide. Examples of immunogenic polypeptides include, but are not limited to, antigens associated with cancer or infectious disease, such as the melanoma-associated antigen gp100, the breast cancer antigen her2/neu or the *Mycobacterium tuberculosis* antigens Mtb8.4, TbH9 and Mtb39. Where the immunogenic polypeptide is unknown, it can be obtained incidentally to the purification of the stress polypeptide from tissue of a subject having cancer or an infectious disease.

The Flagrp170 protein complex can further include additional stress polypeptides, including members of the hsp70, hsp90, grp78 and grp94 stress protein families. The invention additionally provides a pharmaceutical composition comprising a first polynucleotide encoding a Flagrp170 polypeptide and a second polynucleotide encoding an immunogenic polypeptide. In some embodiments involving first and second polynucleotides, the first polynucleotide is linked to the second polynucleotide. The pharmaceutical compositions of the invention can further comprise a physiologically acceptable carrier and/or an adjuvant.

The invention also provides an immunogenic composition comprising the fusion construct or a polypeptide encoded by same. The immunogenic composition can be used in a method of producing activated T cells comprising contacting a T cell with an antigen presenting cell (APC), wherein the APC is modified by contact with the immunogenic composition. The T cell can be, for example, a CD8$^+$ T cell. Also provided is a T cell produced by the method. The immunogenic composition can also be used to elicit an immune response directed against tumor cells, infected cells, or other disease-causing cells. Examples of an immune response that can be elicited through use of the immunogenic composition of the invention include, but are not limited to, increase tumor infiltration by CD8$^+$ T cells, increasing IFN-γ and IL-12 in tumor sites.

Other methods provided by the invention include a method for killing a tumor cell, comprising contacting the tumor cell with the T cell or with an immunogenic composition of the invention, a method for inhibiting tumor growth in a subject, comprising administering to the subject an effective amount of the immunogenic composition, a method for inhibiting the development of a cancer in a subject, comprising administering to the subject an effective amount of the immunogenic composition, and a method for removing tumor cells from a biological sample, comprising contacting a biological sample with the T cell of the invention. The biological sample can be, for example, blood or a fraction thereof.

Also provided is a pharmaceutical composition comprising an antigen-presenting cell (APC) modified by exposure to a Flagrp170 polypeptide or fusion construct. Preferably, the APC is a dendritic cell or a macrophage. The APC can be modified by various means including, but not limited to, peptide loading and transfection with a polynucleotide encoding an immunogenic polypeptide.

The pharmaceutical and immunogenic compositions of the invention can be administered to a subject, thereby providing methods for inhibiting *M. tuberculosis*-infection, for inhibiting tumor growth, for inhibiting the development of a cancer, and for the treatment or prevention of cancer or infectious disease.

The invention further provides a method for producing T cells directed against a tumor cell. The method comprises contacting a T cell with an antigen presenting cell (APC), wherein the APC is modified to present an immunogenic polypeptide associated with the tumor cell. Such T cells can be used in a method for killing a tumor cell, wherein the tumor cell is contacted with the T cell.

The invention also provides a method for removing tumor cells from a biological sample. The method comprises contacting a biological sample with a T cell of the invention. In a preferred embodiment, the biological sample is blood or a fraction thereof. Also provided is a method for inhibiting tumor growth in a subject. The method comprises incubating CD4$^+$ and/or CD8$^+$ T cells isolated from the subject with an antigen presenting cell (APC), wherein the APC is modified to present an immunogenic polypeptide associated with the tumor cell such that T cells proliferate. The method further comprises administering to the subject an effective amount of the proliferated T cells, and thereby inhibiting tumor growth in the subject. In an alternative embodiment, the method for inhibiting tumor growth in a subject comprises incubating CD4$^+$ and/or CD8$^+$ T cells isolated from the subject with an antigen presenting cell (APC), wherein the APC is modified to present an immunogenic polypeptide associated with the tumor cell such that T cells proliferate, cloning at least one proliferated cell, and administering to the patient an effective amount of the cloned T cells, thereby inhibiting tumor growth in the subject.

In a preferred embodiment, the immunogenic polypeptide comprises the extracellular domain (ECD; ECD-PD) or the intracellular domain (ICD) of the breast cancer antigen, her2/neu. In another preferred embodiment, the immunogenic polypeptide comprises gp100, a melanoma-associated antigen.

BRIEF DESCRIPTION OF THE FIGURES

FIG. 2. 6E-6H. Loss of CD8α$^+$ DCs attenuated Flagrp170-induced antitumor effect (E), tumor infiltration by CD8$^+$ T cells (F), intratumoral Ifnγ IFN-γ mRNA levels (G), as well as cytokine (IFN-γ and IL-2) production by splenic CD8$^+$ T cells (H).

FIGS. 8A-8B. Mice (n=5) established with TRAMP-C2 tumors with the size of 3 mm (A) or 6 mm in diameter (B) were treated as indicated. FIG. 8C. Lymphocytes from TRAMP-C2 tumor-bearing mice were stimulated with irradiated TRAMP-C2 cells; IFN-γ levels in the supernatants were measured. FIGS. 8D-8F. Ad.Flagrp170 also profoundly inhibited CT-26 tumors (D) and promoted activation of AH1-specific CD8$^+$ T cells (E). CT-26 tumor-free mice that rejected the secondary tumor challenge showed a potent T cell response to AH-1 peptide, as determined using ELISA assays for IFN-γ production (F).

FIG. 12A. Recruitment of CD8α$^+$CD11c$^+$ and CD11b$^+$ F4/80$^+$ cells to the tumor sites following Ad.Flagrp170 therapy. FIG. 12B. IL-12p70 production in tumor-infiltrating myeloid cells was measured using intracellular cytokine staining assays. FIG. 12C. Flow cytometry analysis of splenic CD11c$^+$ cells in DTx (8 ng/kg)-treated chimera mice reconstituted with BM from DTRtg mice.

DETAILED DESCRIPTION OF THE INVENTION

Figures 1A, 1B, 1C, 1D:
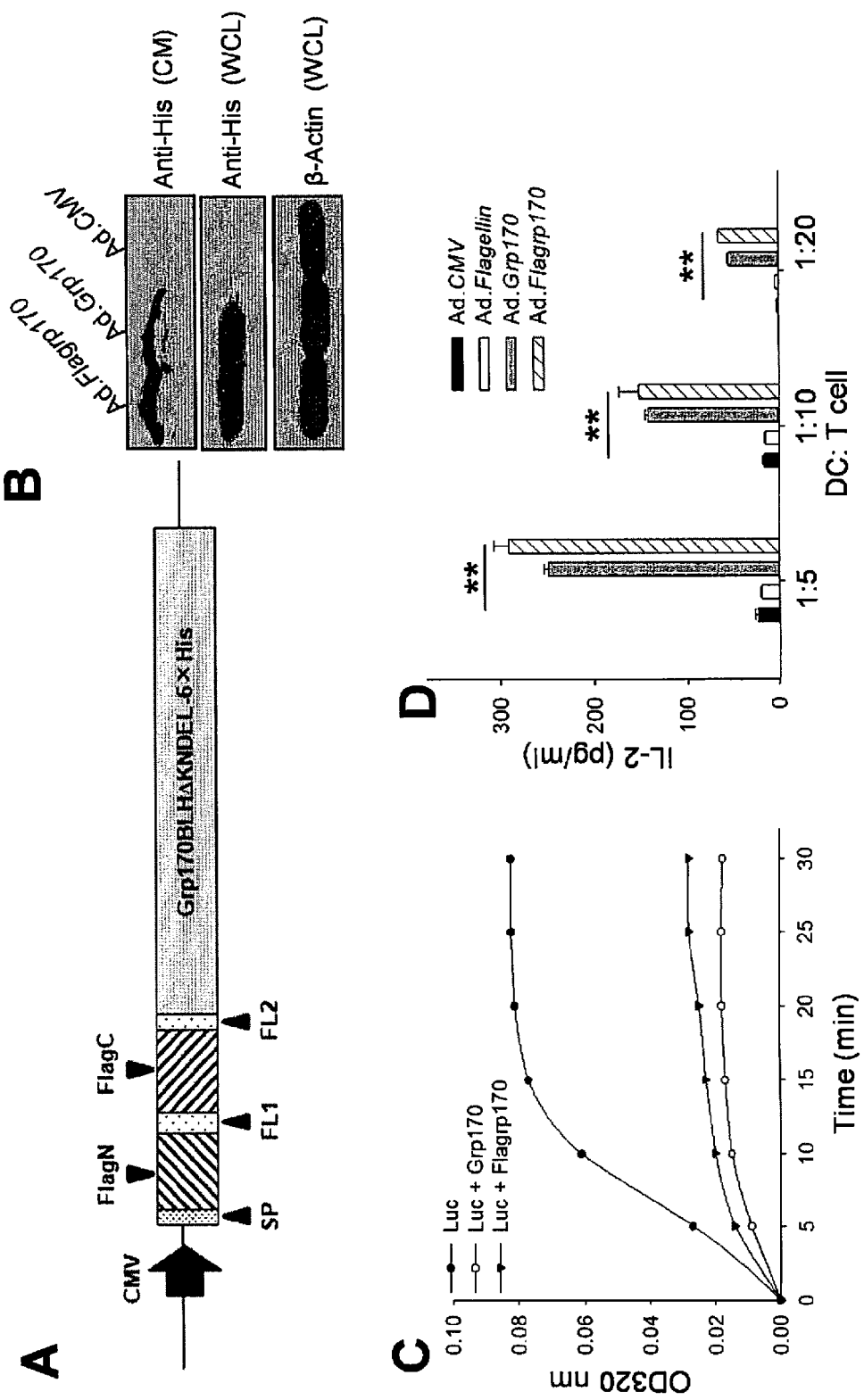
FIG. 1A. Schematic depiction of a chimeric chaperone Flagrp170.
FIG. 1B. Extracellular secretion of Flagrp170 protein following infection of B16 cells with indicated Ads at 100 MOI.
FIG. 1C. Antigen-holding capability of Flagrp170, as indicated by its ability to effectively block luciferase denaturation at 43° C.
FIG. 1D. Tumor-secreted Flagrp170 promotes antigen crosspresentation.

The present invention is based on the design and development of recombinant molecules that are remarkably effective as anti-tumor vaccines. The efficacy of these immunomodulatory molecules has been demonstrated in a number of different cancers using an animal model. The recombinant molecules bring together a select portion of the Flagellin protein with select portions of the stress protein grp170, to create a fusion protein referred to as "Flagrp170". Flagrp170 is much more efficient in generating a therapeutic antitumor immune response than either Grp170 or Flagellin alone. These molecules act through distinct mechanisms in vivo, and the Flagrp170 fusion protein exerts an unexpectedly synergistic effect, exhibiting a remarkably enhanced tumor immunogenicity effective against both local and systemic disease. This allows for full T cell activation without requiring separate administration of a co-stimulatory molecule.

Overview

Stress proteins or heat shock proteins (HSPs) are capable of integrating both innate and adaptive immune responses, and can be utilized as a physiological adjuvant to develop novel immunotherapeutic approaches. Among the HSPs, Grp170, the largest endoplasmic reticulum chaperone, displays exceptional antigen-holding capacity and superior immunostimulatory activity, which has been attributed to its highly efficient chaperoning ability. Molecular engineering of tumor cells for extracellular targeting of Grp170 strongly enhances the immunogenicity of tumor death and molecular-targeted therapy (see, e.g., U.S. Pat. No. 8,080,388, issued Dec. 20, 2011).

Recognition of a pathogen-associated molecule by toll-like receptors (TLRs) triggers an intracellular signaling cascade involving adaptor molecules, protein kinases and transcription factors. The significance of TLR signaling in enhancing antigen presentation and activating adaptive immune responses is well established. TLR-mediated activation of antigen-presenting cells, e.g., dendritic cells (DCs), that includes up-regulation of co-stimulatory signals, is a crucial step in this process. The control exerted by TLRs in linking innate and adaptive immunity is instrumental in the efficacy of vaccines containing TLR ligands. Many established and experimental vaccines incorporate agonists for TLRs, not only to protect against infectious diseases, but also in therapeutic immunization against cancer. Among TLR ligands, Flagellin, a major structural protein of the bacterial flagella and a ligand for TLR5, has been shown to serve as a potent systemic adjuvant. The activity of Flagellin is widely accepted to emanate from its ability to induce DC maturation through TLR5 signaling.

Described herein is a secretable Grp170-Flagellin hybrid chaperone (Flagrp170), which contains the defined NF-κB-activating domain derived from Flagellin. This novel chaperone molecule exhibits robust immune stimulatory activities while maintaining potent antigen-chaperoning efficacy. The studies described in the Example below demonstrate that Flagrp170 is much more efficient than either Grp170 or Flagellin in stimulating antigen- or tumor-specific T cells and controlling both local as well as distant tumors, indicating that Flagrp170 can be used as a powerful immune modulator for therapeutic treatment of cancer and other diseases.

The molecule provided by the invention combines the immunostimulating activity of Grp170 and Flagellin. It will not only shuttle and present disease-associated antigens, but also provide a pathogen-associated 'danger' signal important for activation of the immune system. More importantly, this fusion molecule Flagrp170 is much more efficient than Grp170 or Flagellin in generating a therapeutic antitumor response.

The molecules of the invention can be used in a variety of ways, including, but not limited to, the following exemplary applications:

Flagrp170 gene can be administered to tumor sites for in situ vaccination and to induce systemic tumor-specific immune responses, resulting in efficient control of both treated primary tumors and distant cancer metastases.

Recombinant Flagrp170 protein can be complexed with protein antigens derived from cancer or infectious diseases ("antigens" or "immunogenic polypeptides"). The reconstituted Flagrp170-antigen chaperone complexes can be administered to disease-bearing hosts for augmenting antigen-specific, T cell-mediated immune responses, resulting in efficient control or eradication of the diseases.

Cancer cell lines or tumor cells-derived from patients can be genetically modified with Flagrp170. Flagrp170-expressing cancer cells can be irradiated and used as cell vaccines to immunize cancer patients for induction of cancer-specific immune responses.

Large stress protein is being tested as a vaccine adjuvant for melanoma therapy. The re-engineered Grp170 (Flagrp170) displays much improved efficacy in mounting an antitumor immune response.

As compared with Grp170 or Flagellin, the Flagrp170 displays highly potent activities in antigen chaperoning/presenting and concurrent immune activation. The N-terminal NF-κB activating domain in Flagrp170, which is derived from Flagellin, permits this chimeric chaperone to strongly induce the maturation/activation of professional antigen presenting cells as shown by the enhanced expression of co-stimulatory molecules (CD40, CD80 and CD86) on CD11c+ dendritic cells. Additionally, Flagrp170 possesses an exceptional antigen-holding capacity, which is absent in Flagellin. Therefore, Flagrp170 is highly efficient in promoting the crosspresentation of tumor-associated antigens. As a result, Flagrp170 is capable of completely eradicating and establishing immune memory against murine colon cancer and prostate cancer.

The deletion of hypervariable region of Flagellin, which accounts for the toxicity of Flagellin, makes Flagrp170 much less toxic than Flagellin upon delivery to the host. Previous reports have shown that Flagellin induces the recruitment and accumulation of myeloid-derived suppressor cells (MDSCs), which acts as an important mechanism of cancer immune evasion (Rieber, N., et al., J Immunol, 2013. 190(3): p. 1276-84). Flagrp170 that lacks the hypervariable region of Flagellin has little effect on the expansion or infiltration of $CD11b^+Gr-1+$ MDSCs in the tumor microenvironment. In addition, Flagellin strongly induces neutralizing antibodies in vivo, while the Flagrp170 does not, thereby allowing for repeated delivery of Flagrp170 to enhance its therapeutic efficacy.

The mechanism of Flagrp170 action differs from that of Flagellin. As compared with Grp170 or Flagellin alone, introduction of Flagrp170 to the tumor in situ recruits various immune cells that possess tumor cytolytic activities. In addition to the $CD8^+$ cytolytic T cells and $NK1.1^+$ natural killer (NK) cells, Flagrp170 unexpectedly induces the recruitment of $CD4^+CD8^+$ T cells and $CD8^+NK1.1^+$ NKT cells following treatment of melanoma. Studies from human melanoma patients and murine leukemia model suggest the highly cytolytic potential and effector/memory functions of these two novel immune cell populations, i.e., $CD4^+CD8^+$ T cells and $CD8^+NK1.1^+$ NKT cells [Desfrancois, J., et al., PLoS One, 2010. 5(1): p. e8437; Baker, J., et al., Blood, 2001. 97(10): p. 2923-31]. Furthermore, Flagrp170, but not Grp170 or Flagellin, induces high levels of IL-15 expression in the tumor sites. IL-15 is known to be a critical cytokine for maintaining memory and effector function of T cells.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "selectable marker" refers to a nucleotide sequence which is capable of expression in cells and where expression of the selectable marker confers to cells containing the expressed gene the ability to grow in the presence of a corresponding selective agent, or under corresponding selective growth conditions.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "tumor protein" is a protein that is expressed by tumor cells. Proteins that are tumor proteins also react detectably within an immunoassay (such as an ELISA) with antisera from a patient with cancer.

An "immunogenic polypeptide," as used herein, is a portion of a protein that is recognized (i.e., specifically bound) by a B-cell and/or T-cell surface antigen receptor. Such immunogenic polypeptides generally comprise at least 5 amino acid residues, more preferably at least 10, and still more preferably at least 20 amino acid residues of a protein associated with cancer or infectious disease. Certain preferred immunogenic polypeptides include peptides in which an N-terminal leader sequence and/or transmembrane domain have been deleted. Other preferred immunogenic polypeptides may contain a small N- and/or C-terminal deletion (e.g., 1-30 amino acids, preferably 5-15 amino acids), relative to the mature protein.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, to "prevent" or "treat" a condition means to decrease or inhibit symptoms indicative of the condition or to delay the onset or reduce the severity of the condition.

As used herein, "adjuvant" includes those adjuvants commonly used in the art to facilitate an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquilla Biopharmaceuticals); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

Polynucleotides of the Invention

The invention provides polynucleotides that encode a Flagrp170 protein that includes an NF-κB-activating domain of Flagellin in operable linkage with a polynucleotide encoding a truncated Grp170. Polynucleotides encoding any of the Flagrp170 proteins and variants described herein are encompassed by the invention. Additional elements may be included in a polynucleotide construct of the invention, such as linkers, promoters, other expression control sequences, as well as sequences encoding signal or leader peptide, selectable markers, and other elements known to those skilled in the art. In one embodiment, for example, the polynucleotide is designed for incorporation into a replication-selective oncolytic virus engineered to specifically destroy cancer cells with no or minimal toxicity to normal tissue.

Preferred polynucleotides comprise at least 15 consecutive nucleotides, preferably at least 30 consecutive nucleotides and more preferably at least 45 consecutive nucleotides, that encode a portion of a Flagrp170 protein or immunogenic polypeptide. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (one that encodes the recited polypeptide) or may comprise a variant of such a sequence. Polynucleotide variants contain one or more substitutions, additions, deletions and/or insertions such that the immunogenicity of the encoded polypeptide is not diminished, relative to a native stress protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned. In some instances, identity refers to the percentage of identity between two sequences when compared over the entire length of the reference sequence.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native Flagrp170 protein (or a complementary sequence). Suitable moderately stringent conditions include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding a protein may be obtained from a cDNA library prepared from tissue expressing the protein mRNA. The protein-encoding gene may also be obtained from a genomic library or by oligonucleotide synthesis. Libraries can be screened with probes (such as antibodies to the protein or oligonucleotides of at least about 20-80 bases) designed to identify the gene of interest or the protein encoded by it. Illustrative libraries include human liver cDNA library (human liver 5' stretch plus cDNA, Clontech Laboratories, Inc.) and mouse kidney cDNA library (mouse kidney 5'-stretch cDNA, Clontech laboratories, Inc.). Screening the cDNA or genomic library with the selected probe may be conducted using standard procedures, such as those described in Green, Sambrook, *Molecular Cloning: A Laboratory Manual* (4$^{th}$ Edition, New York: Cold Spring Harbor Laboratory Press, 2012).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs, which employ various algorithms to measure homology.

Nucleic acid molecules having protein coding sequence may be obtained by screening selected cDNA or genomic libraries, and, if necessary, using conventional primer extension procedures as described in Sambrook et al., supra, to detect precursors and processing intermediates of mRNA that may not have been reverse-transcribed into cDNA.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a desired protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding the polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Flagrp170 Fusion Protein & Related Polypeptides

Within the context of the present invention, Flagrp170 polypeptides comprise at least an NF-κB-activating domain of Flagellin and a truncated Grp170, e.g. an ATP-binding domain deletion, an ER retention sequence deletion, and/or a variant thereof. In one embodiment, the Flagrp170 has the amino acid sequence of SEQ ID NO: 1. In another embodiment, the Flagrp170 is a variant of the sequence shown in SEQ ID NO: 1. For example, the variant may be altered by conservative substitutions, substitution of one or more murine-specific GRP amino acid residues with corresponding amino acids from the human Grp170 sequence (see sequence comparison below), or other minor variations that one skilled in the art would recognize as suitable for the intended use of the molecule.

Polypeptides as described herein may be of any length. Additional sequences derived from the native protein and/or heterologous sequences may be present, and such sequences may, but need not, possess further peptide binding, immunogenic or antigenic properties. In some embodiments, the polypeptide further includes all or a portion of a member of the hsp70, hsp90, grp78 and grp94 stress protein families.

Candidate fragments and variants of the stress polypeptides disclosed herein can be identified as having chaperoning activity by assessing their ability to solubilize heat-denatured luciferase and to refold luciferase in the presence of rabbit reticulocyte lysate (Oh et al., supra).

Amino acid sequence of Flagrp170 fusion protein used in the Examples below (SEQ ID NO: 1):

Met A A T V R R Q R P R R L L C W A L V A V L L A
D L L A L S D T L A A Q V I N T N S L S L L T Q N
N L N K S Q S A L G T A I E R L S S G L R I N S A
K D D A A G Q A I A N R F T A N I K G L T Q A S R
N A N D G I S I A Q T T E G A L N E I N N L Q R
V R E L A V Q S A N S T N S Q S D L D S I Q A E I
T Q R L N E I D R V S G Q T Q F N G V K V L A Q D
N T L T I Q V G A N D G E T I D I D L K Q I N S Q
T L G L D T L N V S P G I S G G G G G I L D
S Met G A T T T E N P L Q K I D A A L A Q V D T L
R S D L G A V Q N R F N S A I T N L G N T V N N L
T S A R S R I E D S D Y A T E V S N Met S R A Q I
L Q Q A G T S V L A Q A N Q V P Q N V L S L L R G
S G L A E A A A K E A A A K E A A A K E A A A K A
A A G E F K V K P F V V R D A V I Y P I L V E F T
R E V E E E P G L R S L K H N K R V L F S R Met G
P Y P Q R K V I T F N R Y S H D F N F H I N Y G D
L G F L G P E D L R V F G S Q N L T T V K L K G V
G E S F K K Y P D Y E S K G I K A H F N L D E S G
V L S L D R V E S V F E T L V E D S P E E E S T L
T K L G N T I S S L F G G G T S S D A K E N G T D

A V Q E E E E S P A E G S K D E P A E Q G E L K E
E A E P P A E E T S Q P P P S E P K G D A A R E G
E K P D E K E S G D K P E A Q K P N E K G Q A G P
E G A A P A P E E D K K P K P A R K Q K Met V E E
I G V E L A V L D L P D L P E D E L A R S V Q K L
E E L T L R D L E K Q E R E K A A N S L E A F I F
E T Q D K L Y Q P E Y Q E V S T E E Q R E E I S G
K L S A T S T W L E D E G F G A T I V Met L K D K
L A E L R K L C Q G L F F R V E E R R K W P E R L
S A L D N L L N H S S I F L K G A R L I P E Met D
Q V F T E V E Met T T L E K V I N D T W A W K N A
T L A E Q A K L P A T E K P V L L S K D I E A K
Met Met A L D R E V Q Y L L N K A K F T K P R P R
P K D K N G T R A E P P L N A S A G D Q E E K V I
P P A G Q T E E A K P I L E P D K E E T G T E P A
D S E P L E L G G P G A G P E Q E E Q S A G Q K R
P S H H H H H H G

Mouse Grp170 protein ID: AAF65544 (SEQ ID NO: 2):

```
  1 maatvrrqrp rrllcwalva vlladllals dtlavmsvdl gsesmkvaiv kpgvpmeivl
 61 nkesrrktpv tvtlkenerf lgdsaagmai knpkatlryf qhllgkqadn phvalyrsrf
121 pehelivdpq rqtvrfqisp qlqfspeevl gmvlnysrsl aedfaeqpik davitvpaff
181 nqaerravlq aarmaglkvl qlindntata lsygvfrrkd instaqnvmf ydmgsgstvc
241 tivtyqtvkt keagmqpqlq irgvgfdrtl gglemelrlr ehlaklfneq rkgqkakdvr
301 enpramakll reanrlktvl sanadhmaqi eglmddvdfk akvtrvefee lcadlfdrvp
361 gpvqqalqsa emsldqieqv ilvggatrvp kvqevllkav gkeelgknin adeaaamgav
421 yqaaalskaf kvkpfvvrda viypilveft reveeepglr slkhnkrvlf srmgpypqrk
481 vitfnryshd fnfhinygdl gflgpedlrv fgsqnlttvk lkgvgesfkk ypdyeskgik
541 ahfnldesgv lsldrvesvf etlvedspee estltklgnt isslfgggts sdakengtda
601 vqeeeespae gskdepaeqg elkeeaeppa eetsqpppse pkgdaarege kpdekesgdk
661 peaqkpnekg qagpegaapa peedkkpkpa rkqkmveeig velavldlpd lpedelarsv
721 qkleeltlrd lekqerekaa nsleafifet qdklyqpeyq evsteeqree isgklsatst
781 wledegfgat tvmlkdklae lrklcqglff rveerrkwpe rlsaldnlln hssiflkgar
```

```
841 lipemdqvft evemttlekv indtwawkna tlaeqaklpa tekpvllskd ieakmmaldr 901 evqyllnkak ftkprprpkd kngtraeppl nasagdqeek vippagqtee akpilepdke 961 etgtepadse plelggpgag peqeeqsagq krpskndel
```

Human Grp170 protein ID: NP_001124463 (SEQ ID NO: 3): (Human Grp170 is also referred to as HYOU1.)

```
  1 madkvrrqrp rrrvcwalva vlladllals dtlavmsvdl gsesmkvaiv kpgvpmeivl 61 nkesrrktpv ivtlkenerf fgdsaasmai knpkatlryf qhllgkqadn phvalyqarf 121 peheltfdpq rqtvhfqiss qlqfspeevl gmvlnysrsl aedfaeqpik davitvpvff 181 nqaerravlq aarmaglkvl qlindntata lsygvfrrkd inttaqnimf ydmgsgstvc 241 tivtyqmvkt keagmqpqlq irgvgfdrtl gglemelrlr erlaglfneq rkgqrakdvr 301 enpramakll reanrlktvl sanadhmaqi eglmddvdfk akvtrvefee lcadlfervp 361 gpvqqalqsa emsldeieqv ilvggatrvp rvqevllkav gkeelgknin adeaaamgav 421 yqaaalskaf kvkpfvvrda vvypilveft reveeepgih slkhnkrvlf srmgpypqrk 481 vitfnryshd fnfhinygdl gflgpedlrv fgsqnlttvk lkgvgdsfkk ypdyeskgik 541 ahfnldesgv lsldrvesvf etlvedsaee estltklgnt isslfgggtt pdakengtdt 601 vqeeeespae gskdepgeqv elkeeaeapv edgsqppppe pkgdatpege katekengdk 661 seaqkpseka eagpegvapa pegekkqkpa rkrrmveeig velvvldlpd lpedklaqsv 721 qklqdltlrd lekqerekaa nsleafifet qdklygpeyq evsteeqree isgklsaast 781 wledegvgat tvmlkeklae lrklcqglff rveerkkwpe rlsaldnlln hssmflkgar 841 lipemdqift evemttlekv inetwawkna tlaeqaklpa tekpvllskd ieakmmaldr 901 evqyllnkak ftkprprpkd kngtraeppl nasasdqgek vippagqted aepisepekv 961 etgsepgdte plelggpgae peqkeqstgq krplkndel
```

Amino acid sequences of mouse and human Grp170 share high homology. Alignment data of mouse (line 1 below; SEQ ID NO: 2) and human (line 2 below; SEQ ID NO: 3) Grp170:

```
1 maatvrrqrprprrllcwalvavlladllalsdtlavmsvdlgsesmkva
2 madkvrrqrprrrvcwalvavlladllalsdtlavmsvdlgsesmkva
c ** .******* :*****************************

1 ivkpgvpmeivlnkesrrktpvtvtlkenerflgdsaagmaiknpkat
2 ivkpgvpmeivlnkesrrktpvivtlkenerffgdsaasmaiknpkat
c ******************** ******** :***** .********

1 lryfqhllgkqadnphvalyrsrfpehelivdpqrqtvrfqispqlqf
2 lryfqhllgkqadnphvalyqarfpeheltfdpqrqtvhfqissqlqf
c ********************::******* .******:****.****

1 speevlgmvlnysrslaedfaeqpikdavitvpaffnqaerravlqaa
2 speevlgmvlnysrslaedfaeqpikdavitvpvffnqaerravlqaa
c ********************************.**************

1 rmaglkvlqlindntatalsygvfrrkdinstaqnvmfydmgsgstvc
2 rmaglkvlqlindntatalsygvfrrkdinttaqnimfydmgsgstvc
c ****************************** **** ************

1 tivtyqtvktkeagmqpqlqirgvgfdrtlgglemelrlrehlaklfn
2 tivtyqmvktkeagmqpqlqirgvgfdrtlgglemelrlrerlaglfn
c ******.**********************************:** ***

1 eqrkqgkakdvrenpramakllreanrlktvlsanadhmaqieglmdd
2 eqrkqgrakdvrenpramakllreanrlktvlsanadhmaqieglmdd
c ******:*****************************************

1 vdfkakvtrvefeelcadlfdrvpgpvqqalqsaemsldqieqvilvg
2 vdfkakvtrvefeelcadlfervpgpvqqalqsaemsldeieqvilvg
c *********************:*****************:********

1 gatrvpkvqevllkavgkeelgkninadeaaamgavyqaaalskafkv
2 gatrvprvqevllkavgkeelgkninadeaaamgavyqaaalskafkv
c ******:*****************************************

1 kpfvvrdaviypilveftreveeepglrslkhnkrvlfsrmgpypqrk
2 kpfvvrdavvypilveftreveeepgihslkhnkrvlfsrmgpypqrk
c ********:*****************::********************

1 vitfnryshdfnfhinygdlgflgpedlrvfgsqnlttvklkgvgesf
2 vitfnryshdfnfhinygdlgflgpedlrvfgsqnlttvklkgvgdsf
c ********************************************:**

1 kkypdyeskgikahfnldesgvlsldrvesvfetlvedspeeestltk
2 kkypdyeskgikahfnldesgvlsldrvesvfetlvedsaeeestltk
c ***************************************.********

1 lgntisslfgggtssdakengtdavqeeeespaegskdepaeqgelke
2 lgntisslfgggttpdakengtdtvqeeeespaegskdepgeqvelke
c *************:.********.****************.** ****

1 eaeppaeetsqpppsepkgdaaregekpdekesgdkpeaqkpnekgqa
2 eaeapvedgsqppppepkgdatpegekatekengdkseaqkpsekaea
c ***.*.*: ***** .****** .*** .*** .*****.**.::**
```

```
1 gpegaapapeedkkpkparkqkmveeigvelavldlpdlpedelarsv
2 gpegvapapegekkqkparkrrmveeigvelvvldlpdlpedklaqsv
c ****.***** :** *****.:**********.**********:**:**

1 qkleeltlrdlekqerekaansleafifetqdklyqpeyqevsteeqr
2 qklqdltlrdlekqerekaansleafifetqdklyqpeyqevsteeqr
c ***::********************************************

1 eeisgklsatstwledegfgattvmlkdklaelrklcqglffrveerr
2 eeisgklsaastwledegvgattvmlkeklaelrklcqglffrveerk
c *********:*******.*********.*******************:

1 kwperlsaldnllnhssiflkgarlipemdqvftevemttlekvindt
2 kwperlsaldnllnhssmflkgarlipemdqiftevemttlekvinet
c ****************:**************:**************:*

1 wawknatlaeqaklpatekpvllskdieakmmaldrevqyllnkakft
2 wawknatlaeqaklpatekpvllskdieakmmaldrevqyllnkakft
c ************************************************

1 kprprpkdkngtraepplnasagdqeekvippagqteeakpilepdke
2 kprprpkdkngtraepplnasasdqgekvippagqtedaepisepekv
c **********************.** **********.*:** **:.*
```

```
1 etgtepadseplelggpgagpeqeeqsagqkrpskndel
2 etgsepgdteplelggpgaepeqkeqstgqkrplkndel
c ***:**.*:**********.***.***:***** *****
```

The leader sequence (or signal peptide) of Grp170 is the first 34 amino acids. The N-terminal 34 amino acids comprise a typical leader sequence for targeting the protein to the endoplasmic reticulum. See Chen et al., 1996, FEBS Letters 380:68-72. Intracellular Grp170 naturally resides in the endoplasmic reticulum. This leader sequence will target newly synthesized Grp170 to the endoplasmic reticulum for post-translational modification.

Mouse leader sequence (SEQ ID NO: 4):
maatvrrqrprrllcwalvavlladllalsdtla

Human leader sequence (SEQ ID NO: 5):
madkvrrqrprrrvcwalvavlladllalsdtla

Truncated murine Grp170 (amino acids 431-994; N-terminus and ER retention sequence deleted; SEQ ID NO: 6):

```
        kvkpfvvrda viypilveft reveeepglr slkhnkrvlf srmgpypqrk
    481 vitfnryshd fnfhinygdl gflgpedlrv fgsqnlttvk lkgvgesfkk ypdyeskgik
    541 ahfnldesgv lsldrvesvf etlvedspee estltklgnt isslfgggts sdakengtda
    601 vqeeeespae gskdepaeqg elkeeaeppa eetsqpppse pkgdaarege kpdekesgdk
    661 peaqkpnekg qagpegaapa peedkkpkpa rkqkmveeig velavldlpd lpedelarsv
    721 qkleeltlrd lekqerekaa nsleafifet qdklyqpeyq evsteeqree isgklsatst
    781 wledegfgat tvmlkdklae lrklcqglff rveerrkwpe rlsaldnlln hssiflkgar
    841 lipemdqvft evemttlekv indtwawkna tlaeqaklpa tekpvllskd ieakmmaldr
    901 evqyllnkak ftkprprpkd kngtraeppl nasagdqeek vippagqtee akpilepdke
    961 etgtepadse plelggpgag peqeeqsagq krps
```

```
        kvkpfvvrda vvypilveft reveeepgih slkhnkrvlf srmgpypqrk
    481 vitfnryshd fnfhinygdl gflgpedlrv fgsqnlttvk lkgvgdsfkk ypdyeskgik
    541 ahfnldesgv lsldrvesvf etlvedsaee estltklgnt isslfgggtt pdakengtdt
    601 vqeeeespae gskdepgeqv elkeeaeapv edgsqppppe pkgdatpege katekengdk
    661 seaqkpseka eagpegvapa pegekkqkpa rkrrmveeig velvvldlpd lpedklaqsv
    721 qklqdltlrd lekqerekaa nsleafifet qdklyqpeyq evsteeqree isgklsaast
    781 wledegvgat tvmlkeklae lrklcqglff rveerkkwpe rlsaldnlln hssmflkgar
    841 lipemdqift evemttlekv inetwawkna tlaeqaklpa tekpvllskd ieakmmaldr
    901 evqyllnkak ftkprprpkd kngtraeppl nasasdqgek vippagqted aepisepekv
    961 etgsepgdte plelggpgae peqkeqstgq krpl
```

Complete amino acid sequence of Flagellin (*Salmonella enterica* serovar *Typhimurium* LT2; Accession No. AAL20871.1; SEQ ID NO: 8):

Truncated human Grp170 (amino acids 431-994; N-terminus and ER retention sequence deleted; SEQ ID NO: 7):

```
  1 maqvintnsl slltqnnlnk sqsalgtaie rlssglrins akddaagqai anrftanikg 61 ltqasrnand gisiaqtteg alneinnnlq rvrelavqsa nstnsqsdld siqaeitqrl 121 neidrvsgqt qfngvkvlaq dntltiqvga ndgetididl kqinsqtlgl dtlnvqqkyk 181 vsdtaatvtg yadttialdn stfkasatgl ggtdqkidgd lkfddttgky yakvtvtggt 241 gkdgyyevsv dktngevtla ggatspltgg lpatatedvk nvqvanadlt eakaaltaag 301 vtgtasvvkm sytdnngkti dgglavkvgd dyysatqnkd gsisinttky taddgtskta 361 lnklggadgk tevvsiggkt yaaskaeghn fkaqpdlaea aatttenplq kidaalaqvd 421 tlrsdlgavq nrfnsaitnl gntvnnltsa rsriedsdya tevsnmsraq ilqqagtsvl 481 aqanqvpqnv lsllr
```

NF-κB-activating domain of Flagellin comprises N-terminal amino acids 2-175 and C-terminal amino acids 402-495 (linker is underlined; SEQ ID NO: 9):

AQVINTNSLSLLTQNNLNKSQSALGTAIERLSSGLRINSAKDDAAGQAIA

NRFTANIKGLTQASRNANDGISIAQTTEGALNEINNNLQRVRELAVQSAN

STNSQSDLDSIQAEITQRLNEIDRVSGQTQFNGVKVLAQDNTLTIQVGAN

DGETIDIDLKQINSQTLGLDTLNV<u>SPGISGGGGGILDSMG</u>ATTTENPLQK

IDAALAQVDTLRSDLGAVQNRFNSAITNLGNTVNNLTSARSRIEDSDYAT

EVSNMSRAQILQQAGTSVLAQANQVPQNVLSLLR

In some embodiments, the immunotherapeutic protein further comprises an immunogenic polypeptide, such as one associated with a cancer or precancerous condition, or one associated with an infectious disease. One example of an immunogenic polypeptide associated with a cancer is a her-2/neu peptide (Bargmann et al., 1986, Nature 319(6050): 226-30; Bargmann et al., 1986, Cell 45(5):649-57). Examples of her-2/neu peptides include, but are not limited to, the intracellular domain of her-2/neu (amino acid residues 676-1255; see Bargmann et al. references above), p369 (also known as E75; KIFGSLAFL; SEQ ID NO: 10) of the extracellular domain of her-2/neu, ECD-PD (see WO02/12341, published Feb. 14, 2002, and WO00/44899, published Aug. 3, 2000), and p546, a transmembrane region of her-2/neu (VLQGLPREYV; SEQ ID NO: 11). These her-2/neu sequences can be found in Accession No. NP_004439. Another example of an immunogenic polypeptide associated with a cancer is gp100, a melanoma-associated antigen. In other embodiments, the immunogenic polypeptide is associated with an infectious disease. One example of an immunogenic polypeptide associated with an infectious disease is an antigen derived from M. tuberculosis, such as M. tuberculosis antigens Mtb 8.4 (Coler et al., 1998, J. Immunol. 161(5):2356-64), Mtb 39 (also known as Mtb39A; Dillon et al., 1999, Infect. Immun. 67(6):2941-50), or TbH9, the latter being an example of a tuberculosis antigen whose ability to form complexes with stress proteins has been confirmed.

The immunogenic polypeptide may be known or unknown. Unknown immunogenic polypeptides can be obtained incidentally to the purification of Flagrp170 from supernatant obtained from cultured disease cells prepared from tissue of a subject having cancer or a precancerous condition or having an infectious disease. Such cultured cells can be modified to express and produce a secretable Flagrp170, which secreted Flagrp170 would be associated with immunogenic polypeptides related to the diseased cells. In other embodiments, the immunogenic polypeptide comprises a known antigen.

Immunogenic polypeptides may generally be identified using well known techniques, such as those summarized in Paul, Fundamental Immunology, 4th ed., 663-665 (Lippincott-Raven Publishers, 1999) and references cited therein. Such techniques include screening polypeptides for the ability to react with antigen-specific antibodies, antisera and/or T-cell lines or clones. As used herein, antisera and antibodies are antigen-specific if they specifically bind to an antigen (i.e., they react with the protein in an ELISA or other immunoassay, and do not react detectably with unrelated proteins). Such antisera and antibodies may be prepared using well known techniques. An immunogenic polypeptide can be a portion of a native protein that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Stress protein complexes of the invention can be obtained through a variety of methods. In one example, a recombinant Flaprp170 is mixed with cellular material (e.g., lysate), to permit binding of the Flagrp170 polypeptide with one or more immunogenic polypeptides within the cellular material. Such binding can be enhanced or altered by stress conditions, such as heating of the mixture. In another example, target cells are transfected with Flagrp170 that has been tagged (e.g., HIS tag) for later purification. This example provides a method of producing recombinant stress polypeptide in the presence of immunogenic material. In yet another example, stress conditions are used to induce Flagrp170 in transformed target cells prior to purification of the stress polypeptide. This stressing can be performed in situ, in vitro or in cell cultures.

Polypeptide variants can be encompassed by the invention. Such variants preferably exhibit at least about 70%, more preferably at least about 90% and most preferably at least about 95% identity (determined as described above) to the identified polypeptides, over the full-length of the identified polypeptide.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein that co-translationally or post-translationally directs transfer of the protein. The polypeptide may also be conjugated to a linker or other sequence for ease of synthesis, purification or identification of the polypeptide (e.g., poly-FEs), or to enhance binding of the polypeptide to a solid support. For example, a polypeptide may be conjugated to an immunoglobulin Fc region.

Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Polypeptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

Construction of Fusion Proteins

The Flagrp170 polypeptide is a fusion protein that comprises portions of Flagellin and grp170 polypeptides as described herein, optionally further including an unrelated sequence. In some embodiments, the fusion protein comprises a truncated grp170 and the NF-κB-activating domain of Flagellin. The immunogenic polypeptide can optionally further comprise all or a portion of a tumor protein or a protein associated with an infectious disease.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86-91, 1997).

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system.

Preferably, such polypeptides are at least about 90% pure, more preferably at least about 95% pure and most preferably at least about 99% pure. A polynucleotide is considered to be isolated if, for example, it is cloned into a vector that is not a part of the natural environment.

T Cells

Immunotherapeutic compositions may also, or alternatively, comprise T cells activated as described herein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ magnetic cell selection system, available from Nexell Therapeutics, Irvine, Calif. (see also U.S. Pat. No. 5,536,475); or MACS cell separation technology from Miltenyi Biotec, including Pan T Cell Isolation Kit, CD4+ T Cell Isolation Kit, and CD8+ T Cell Isolation Kit (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a Flagrp170, polynucleotide encoding a Flagrp170 and/or an antigen presenting cell (APC) that has been in contact with Flagrp170. The stimulation is performed under conditions and for a time sufficient to permit the generation of T cells that are specific for the polypeptide. Preferably, a Flagrp170 polypeptide or polynucleotide is present within a delivery vehicle, such as a microsphere, to facilitate the generation of specific T cells.

T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065-1070, 1994.

Detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a Flagrp170 (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF-α or IFN-γ) is indicative of T cell activation (see Coligan et al., Current Protocols in Immunology, vol. 1, Wiley Interscience (Greene 1998)). T cells that have been activated in response to a Flagrp170 polypeptide, polynucleotide or polypeptide-expressing APC may be CD4+ and/or CD8+. T cells can be expanded using standard techniques.

Within preferred embodiments, the T cells are derived from either a patient or a related, or unrelated, donor and are administered to the patient following stimulation and expansion. For therapeutic purposes, CD4+ or CD8+ T cells that proliferate in response to the polypeptide, polynucleotide or APC can be expanded in number either in vitro or in vivo. Proliferation of such T cells in vitro may be accomplished in a variety of ways. For example, the T cells can be re-exposed to a stress polypeptide complexed with an immunogenic polypeptide, with or without the addition of T cell growth factors, such as interleukin-2, and/or stimulator cells that synthesize a stress protein complex. Alternatively, one or more T cells that proliferate in the presence of a stress protein complex can be expanded in number by cloning. Methods for cloning cells are well known in the art, and include limiting dilution.

Pharmaceutical Compositions and Vaccines

The invention provides Flagrp170 polypeptides, polynucleotides, T cells and/or antigen presenting cells that are incorporated into pharmaceutical compositions, including immunogenic compositions (i.e., vaccines). Pharmaceutical compositions comprise one or more such compounds and, optionally, a physiologically acceptable carrier. Vaccines may comprise one or more such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition or vaccine can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N. Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, intratumoral, or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-α, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. CpG-containing oligonucleotides (in which the CpG dinucleotide is unmethylated) also induce a predominantly Th1 response. Another preferred adjuvant is a saponin, preferably QS21, which may be used alone or in combination with other adjuvants. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham). Any vaccine provided herein may be prepared using well known methods that result in a combination of antigen, immune response enhancer and a suitable carrier or excipient.

A Flagrp170 polypeptide of the invention can also be used as an adjuvant, eliciting a predominantly Th1-type response as well. The Flagrp170 polypeptide can be used in conjunction with other vaccine components, including an immunogenic polypeptide and, optionally, additional adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Antigen Presenting Cells

Any of a variety of delivery vehicles may be employed within pharmaceutical compositions and vaccines to facilitate production of an antigen-specific immune response that targets tumor cells or infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor or anti-infective effects per se and/or to be immunologically compatible with the receiver (i.e., matched BLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNF-α to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNF-α, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II NMC, adhesion molecules (e.g., CD54 and CD11) and costimulatory molecules (e.g., CD40, CD80 and CD86).

Therapeutic and Prophylactic Methods

The Flagrp170 protein complexes and pharmaceutical compositions of the invention can be administered to a subject, thereby providing methods for inhibiting *M. tuberculosis*-infection, for inhibiting tumor growth, for inhibiting the development of a cancer, and for the treatment or prevention of cancer or infectious disease. Representative cancers to be treated using the methods and compositions of the invention include melanoma, prostate cancer, colon cancer, lung cancer, and metastatic disease.

Treatment includes prophylaxis and therapy. Prophylaxis or therapy can be accomplished by a single direct injection at a single time point or multiple time points to a single or multiple sites. Administration can also be nearly simultaneous to multiple sites.

Patients or subjects include mammals, such as human, bovine, equine, canine, feline, porcine, and ovine animals. The subject is preferably a human, and may or may not be afflicted with cancer or disease.

In some embodiments, the condition to be treated or prevented is cancer or a precancerous condition (e.g., hyperplasia, metaplasia, dysplasia). Example of cancer include, but are not limited to, fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenström's macroglobulinemia, and heavy chain disease.

In some embodiments, the condition to be treated or prevented is an infectious disease. Examples of infectious disease include, but are not limited to, infection with a pathogen, virus, bacterium, fungus or parasite. Examples of viruses include, but are not limited to, hepatitis type B or type C, influenza, varicella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I or type II. Examples of bacteria include, but are not limited to, *M. tuberculosis, mycobacterium, mycoplasma, neisseria* and *legionella*. Examples of parasites include, but are not limited to, *rickettsia* and *chlamydia*.

Accordingly, the above pharmaceutical compositions and vaccines may be used to prevent the development of a cancer or infectious disease or to treat a patient afflicted with a cancer or infectious disease. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. In a preferred embodiment, dendritic cells are modified in vitro to present the polypeptide, and these modified APCs are administered to the subject. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy.

In particular, antigen-presenting cells, such as dendritic, macrophage, monocyte, fibroblast and/or B cells, can be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Cultured effector cells can be induced to grow in vivo and to survive long term in substantial numbers by repeated stimulation with antigen supplemented with IL-2 (see, for example, Cheever et al., Immunological Reviews 157:177, 1997).

Alternatively, a vector expressing a polypeptide recited herein can be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumoral administration.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit infection or disease due to infection. Thus, the composition is administered to a subject in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10-50% above the basal (i.e., untreated) level. Such response can be monitored, for example, by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more polypeptides, the amount of each polypeptide present in a dose ranges from about 100 µg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

EXAMPLES

The following examples are presented to illustrate the present invention and to assist one of ordinary skill in making and using the same. The examples are not intended in any way to otherwise limit the scope of the invention.

Example 1: A Multi-Functional Chimeric Chaperone Serves as a Novel Immune Modulator Inducing Therapeutic Antitumor Immunity Described in this example is a novel strategy to target the immunosuppressive tumor environment using a chimeric immune chaperone, leading to systemic T cell-mediated tumor inhibition. The strategy involves incorporation of a pathogen (i.e., Flagellin)-derived, NF-κB-stimulating "danger" signal into the large stress protein or chaperone Grp170 (HYOU1/ORP150) that was previously shown to facilitate antigen crosspresentation. This engineered chimeric molecule (i.e., Flagrp170) is capable of transporting tumor antigens and concurrently inducing functional activation of dendritic cells (DC). Intratumoral administration of adenoviruses expressing Flagrp170 induces a superior antitumor response against B16 melanoma and its distant lung metastasis compared with unmodified Grp170 and flagellin. The enhanced tumor destruction is accompanied with significantly increased tumor infiltration by CD8$^+$ cells as well as elevation of IFN-γ and interleukin (IL)-12 levels in the tumor sites. In situ Ad.Flagrp170 therapy provokes systemic activation of CTLs that recognize several antigens naturally expressing in melanoma (e.g., gp100/PMEL and TRP2/DCT). The mechanistic studies using CD11c-DTR transgenic mice and Batf3-deficient mice reveal that CD8α$^+$ DCs are required for the improved T-cell cross-priming. Antibody neutralization assays show that IL-12 and IFN-γ are essential for the Flagrp170-elicited antitumor response, which also involves CD8$^+$ T cells and natural killer cells. The therapeutic efficacy of Flagrp170 and its immunostimulating activity are also confirmed in mouse prostate cancer and colon carcinoma. Together, targeting the tumor microenvironment with this chimeric chaperone is highly effective in mobilizing or restoring antitumor immunity, supporting the potential therapeutic use of this novel immunomodulator in the treatment of metastatic diseases.

The further details of this example have been published as Yu, et al., 2013, Cancer Res; 73(7); 2093-103, and are also presented in provisional patent application No. 61/737,443, filed Dec. 14, 2012.

Example 2: Flagrp170-Based Gene Therapy & Protein-Based Recombinant Vaccine Therapy Studies by others and us have demonstrated that stress/heat shock proteins can be exploited as immunostimulatory adjuvants for generating antitumor immune responses, which is based on their unique ability of integrating both innate and adaptive immune components (1-7). Grp170, the largest endoplasmic reticulum (ER) chaperone (8), displays an exceptional capacity of holding client proteins or antigens, and a superior immunostimulatory vaccine activity when prepared from tumors or complexing with defined tumor antigens (8-19). The Grp170-mediated immunomodulation has been attributed to its highly efficient chaperoning function during antigen presentation to dendritic cells (DCs) (12, 20). Modification of tumor cells for producing extracellular Grp170 also strongly enhanced immunogenicity of tumor (11, 17).

The significance of pathogen-sensing toll-like receptor (TLR) signaling in enhancing antigen presentation-mediated by specialized antigen-presenting cells (e.g., DCs) and activating innate as well as adaptive immune responses is well established (21). Many established and experimental vaccines incorporate agonists for TLRs, not only to protect against infectious diseases, but also in therapeutic immunization against cancer (22,23). To enhance the potency of Grp170 as an immunostimulator in driving antitumor immunity, we engineered a chimeric chaperone by fusing Grp170 with the defined NF-κB-activating domain of Flagellin (24), a major structural protein of the bacterial flagella (25, 26). This novel hybrid chaperone molecule, termed Flagrp170, not only maintains highly efficient antigen-holding ability, but also possesses a strong capability to activate DCs. We show that introduction of Flagrp170 to the tumor site results in profound inhibition of treated tumors, as well as distal metastases. Despite the comparable activity of Flagellin and Flagrp170 in phonotypical activation of DCs, Flagrp170 is much more efficacious than Flagellin in generating an adaptive immune response and eradicating tumors in multiple cancer models. This may be due to the highly efficient capability of Flagrp170 to capture and chaperone tumor antigens for enhanced cross-priming. The superior antitumor efficacy of Flagrp170 compared to unmodified Grp170 or Flagellin is also supported by enhanced T cell activation both locally (i.e., tumor site) and systemically. Our results indicate that targeting the tumor environment using Flagrp170 can subvert tumor-associated immunosuppressive mechanisms and promote highly immunostimulatory presentation of tumor antigens. The therapeutic efficacy of Flagrp170 and its immune stimulating activity are also confirmed in mouse prostate cancer and colon carcinoma. Therefore, Flagrp170 can be used as a powerful immune modulator for therapeutic treatment of cancer and other diseases.

FIG. 1 shows that Flagrp170 possesses antigen chaperoning and presenting activity. A. Schematic depiction of a chimeric chaperone Flagrp170. The NF-κB-activating domain derived from Flagellin is fused to the ATP-binding domain deletion mutant of Grp170 (BLH). SP: Grp170 signal peptide (34aa); FlagN: N terminus of Flagellin (2-175aa); FL: flexible linker; FlagC: C terminus Flagellin (402-495aa); Grp170BLHΔKNDEL-6×His: the BLH domain of Grp170 (431-994aa), from which the KNDEL sequence was removed and replaced with a His-tag. B. Extracellular secretion of Flagrp170 protein following infection of B16 cells with indicated Ads at 100 MOI. Culture supernatants (CM) and whole cell lysates (WCL) were analyzed for transgene expression. Adenovirus-encoding a secretable form of Grp170 was used as a control. C. Antigen-holding capability of Flagrp170, as indicated by its ability to effectively block luciferase denaturation at 43° C. D. Tumor-secreted Flagrp170 promotes antigen crosspresentation. Gp100-specific CD8$^+$ T cells from Pmel mice were cocultured with BMDCs in the presence of gp100 protein and conditioned media from tumor cells infected with indicated Ads. IL-2 levels in the culture media was assessed using ELISA (**, $p<0.005$).

Figures 2A, 2B, 2C, 2D:
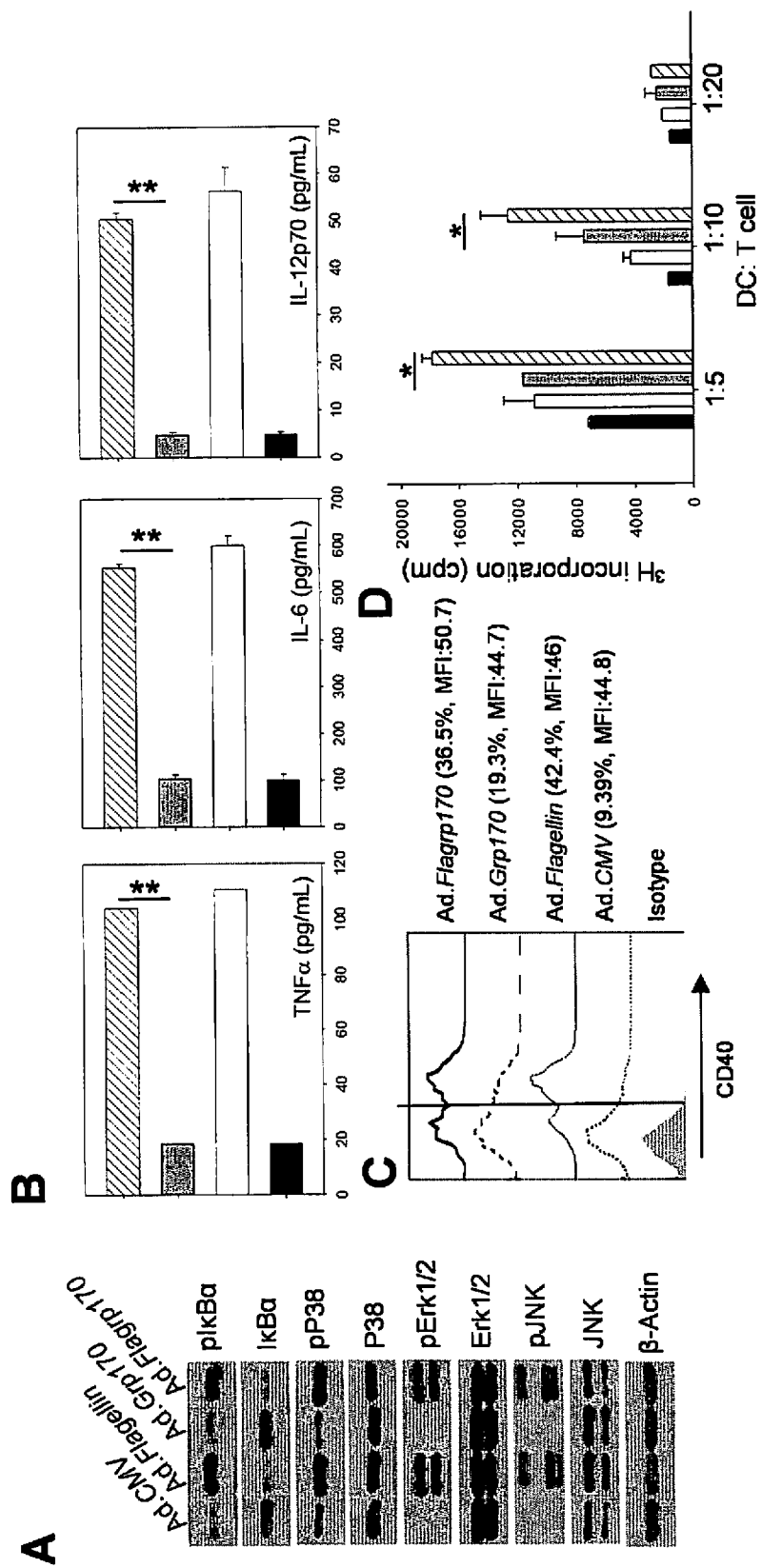
FIG. 2A. Following infection of splenic CD11c$^+$ cells at an MOI of 300 for 90 min, phosphorylation of NF-κBp65 and MAPKs, and degradation of IκBα was determined 24 h later.
FIG. 2B. TNF-α, IL-6 and IL-12p70 were measured using ELISA (, p<0.005).
FIG. 2C. The expression of co-stimulatory molecule CD40 on CD11c$^+$ BMDCs was assessed. D. Adenovirus-infected BMDCs were pulsed with gp100 protein, and cocultured with Pmel cells for 3 days. T cell proliferation was determined using $^3$H-TdR incorporation assays. The experiments were repeated three times with similar results (, p<0.01).

Adenovirus-mediated Flagrp170 expression in DCs enhances functional activation of DCs in vitro, as illustrated in FIG. 2. A. Following infection of splenic CD11c$^+$ cells at an MOI of 300 for 90 min, phosphorylation of NF-κBp65 and MAPKs, and degradation of IκBα was determined 24 h later. B. TNF-α, IL-6 and IL-12p70 were measured using ELISA (, $p<0.005$). C. The expression of co-stimulatory molecule CD40 on CD11c$^+$ BMDCs was assessed. D. Adenovirus-infected BMDCs were pulsed with gp100 protein, and cocultured with Pmel cells for 3 days. T cell proliferation was determined using $^3$H-TdR incorporation assays. The experiments were repeated three times with similar results (, p<0.01). Solid bars in B and D: Ad.CMV; open bars Ad.Flagellin; gray bars Ad.Grp170; striped bars Ad.Flagrp170.

Figures 3A, 3B, 3C:
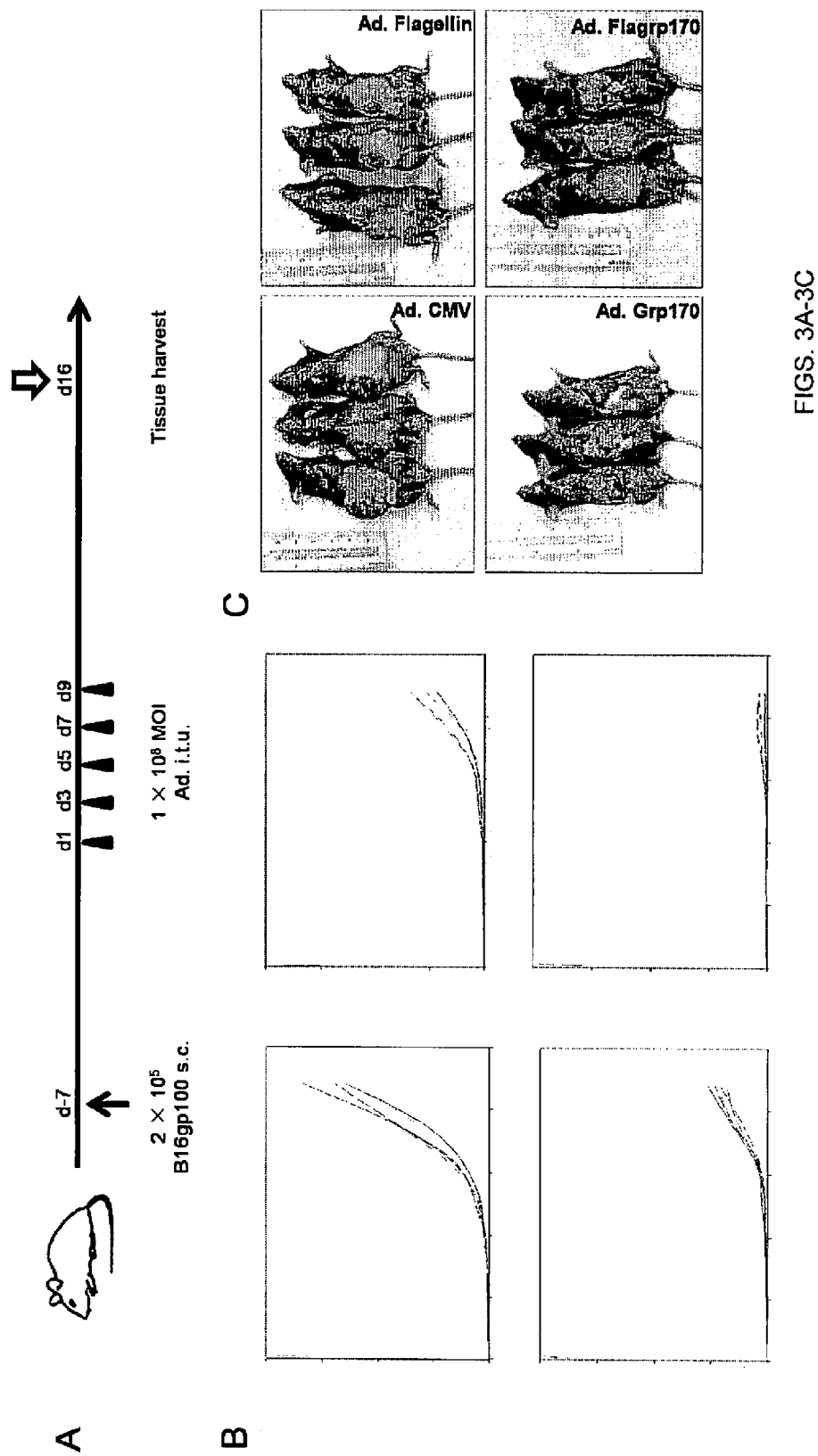
FIG. 3A. illustrates the scheme of intratumoral treatment using Ad.Flagrp170.
FIG. 3B. 2×10$^5$ B16-gp100 cells were implanted subcutaneously (s.c.) on the right flank of C57BL/6 mice (5 mice/group) and 1×10$^8$ p.f.u. of Ads were injected intratumorally when tumors reached a size of 3-4 mm in diameter.
FIG. 3C. Photograph of tumors at the end of the study.

FIG. 3 shows that in situ administration of adenoviruses encoding Flagrp170 induces a potent antitumor response against B16 melanoma in vivo. (A) The scheme of intratumoral treatment using Ad.Flagrp170. (B) Flagrp170 (lower right) effectively controls pre-established B16-gp100 tumors. $2 \times 10^5$ B16-gp100 cells were implanted subcutaneously (s.c.) on the right flank of C57BL/6 mice (5 mice/group) and $1 \times 10^8$ p.f.u. of Ads were injected intratumorally when tumors reached a size of 3-4 mm in diameter. Ad.CMV in upper left; Ad.Flagellin upper right; Ad.Grp170 lower left. The treatment was administrated every other day for a total of five doses. Each line represents data from one individual mouse. Data representative of 3 different experiments are shown. Y-axis is tumor volume in mm³, ranging from 0-4000; x-axis is days, 0-25. (C) Photograph of tumors at the end of the study.

Figures 4A, 4B, 4C:
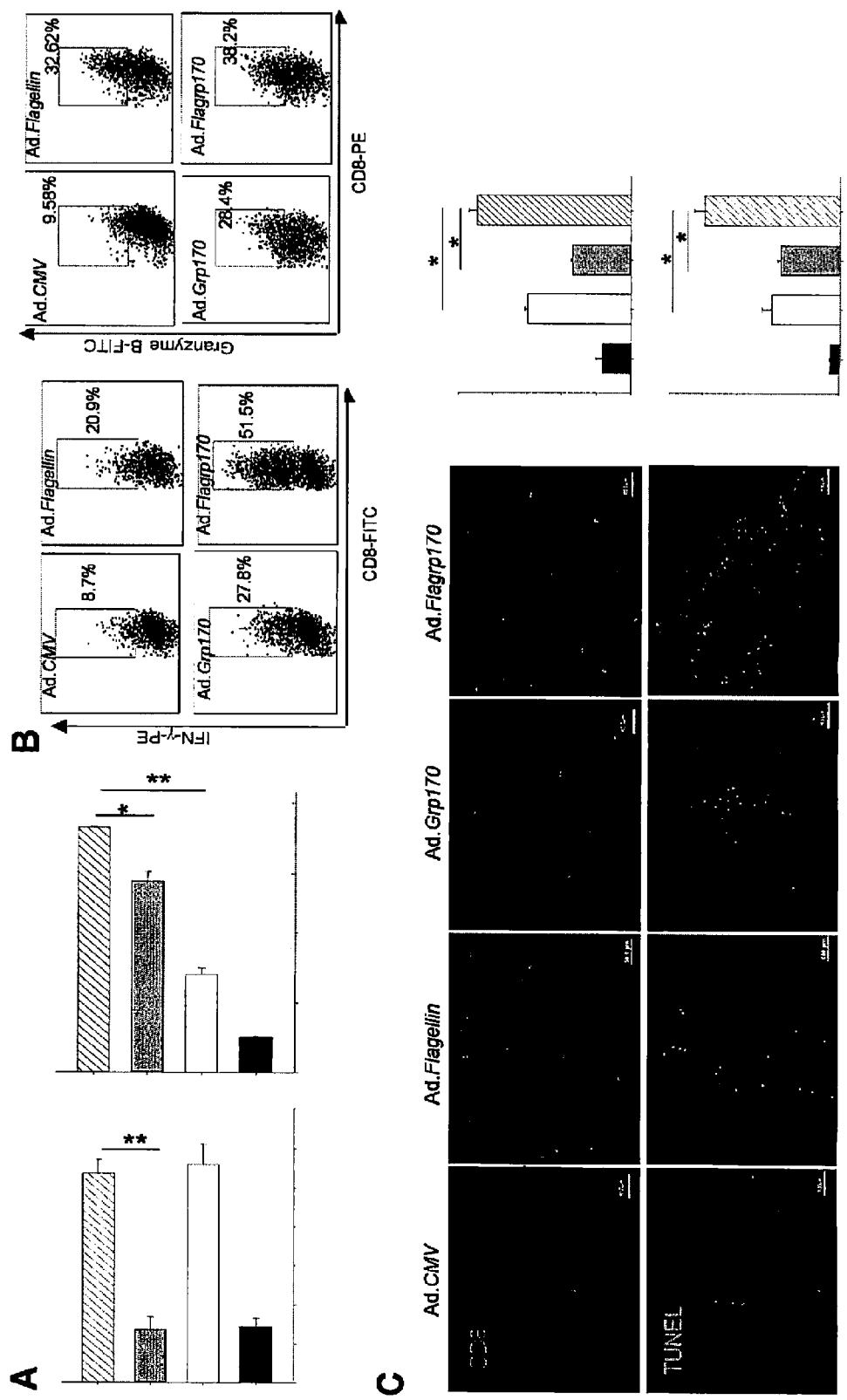
FIG. 4A. Elevation of intratumoral IL-12p70 and IFN-γ in B16 tumors following Ad.Flagrp170 therapy, as determined by ELISA kits.
FIG. 4B. Increased IFN-γ and Granzyme B production in tumor-infiltrating CD8$^+$ T cells, assayed using intracellular cytokine staining.
FIG. 4C. TUNEL assays of tumor cell death and immunofluorescence staining of CD8$^+$ cells. The number of stained cells per mm$^2$ was quantified from 5 randomized visual fields. Scale bars: 50 μm (top) or 100 μm (bottom). Data are representative of three independent experiments. *, p<0.05; **, p<0.01.
Figures 5A, 5B:
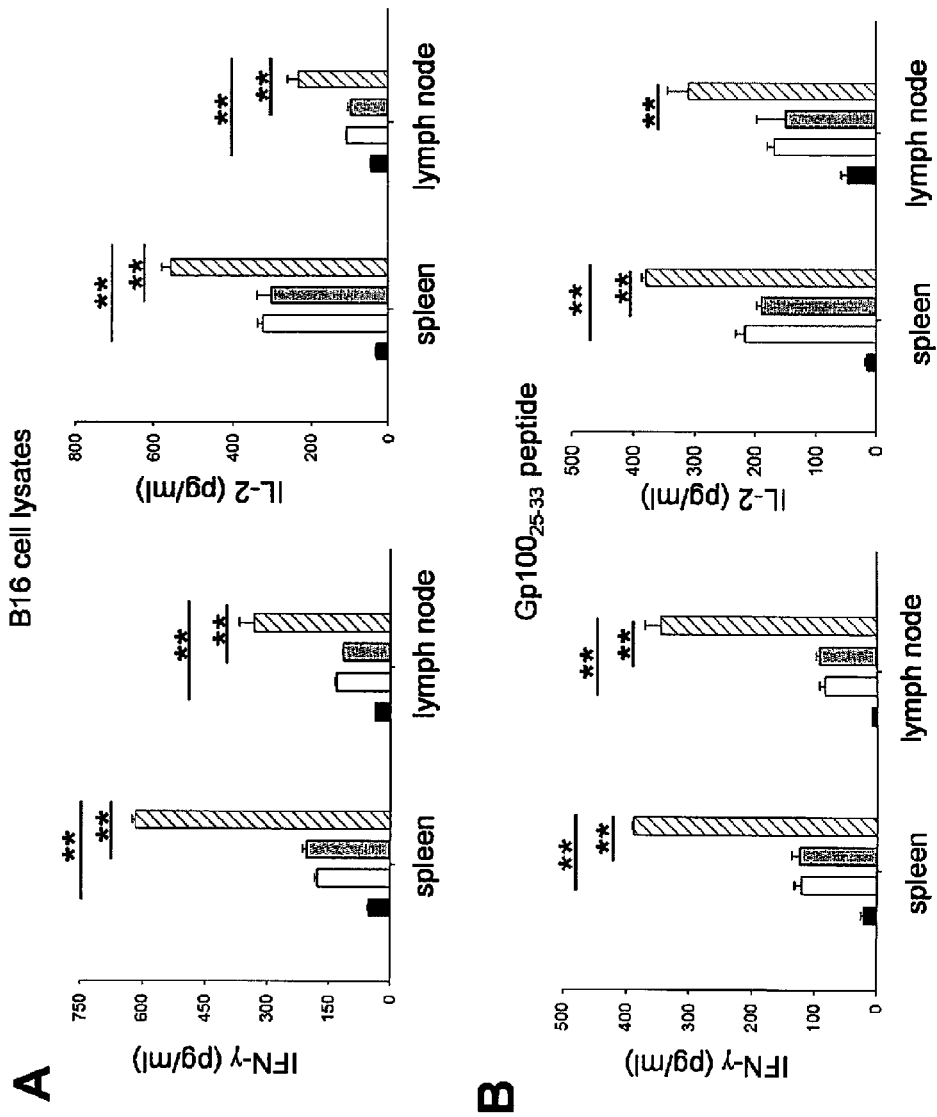
FIGS. 5A-5B. Splenocytes or lymph node cells stimulated with tumor lysates (A). responder cell:tumor cell ratio of 1:3) or gp100$_{25-33}$ peptide (B).
Figure 5C:
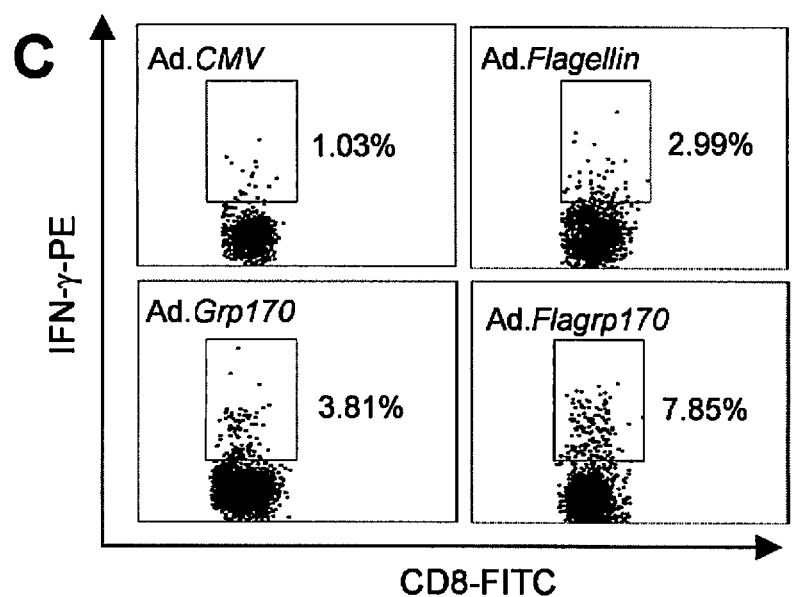
FIG. 5C. Splenocytes were subjected to intracellular cytokine staining for determining the frequency of gp100$_{25-33}$-specific CTLs.
Figure 5D:
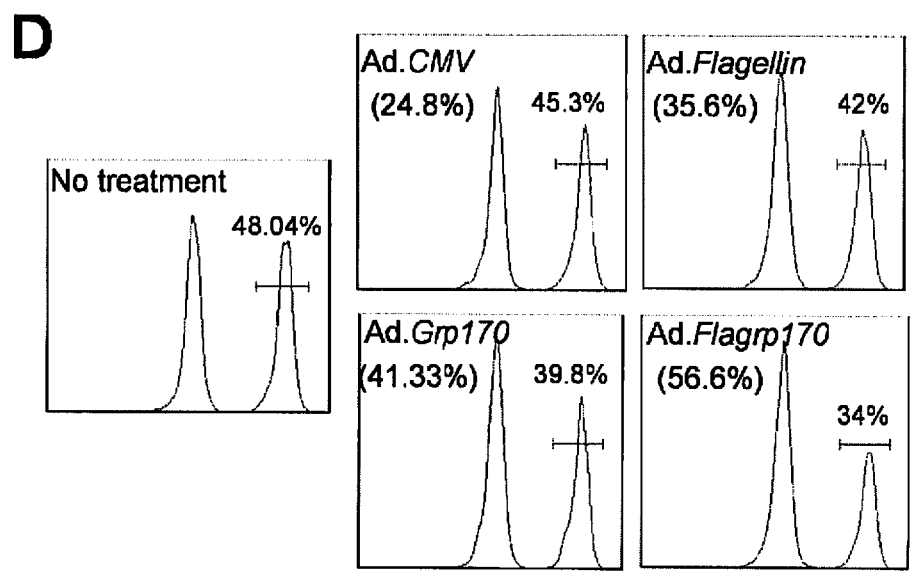
FIG. 5D. Treated mice (n=3) were transferred with gp100$_{25-33}$-pulsed, CFSE$^{high}$ splenocytes (antigen-positive target), and non-pulsed CFSE$^{low}$ splenocytes (negative control) mixed at a ratio of 1:1.
Figures 5E, 5F:
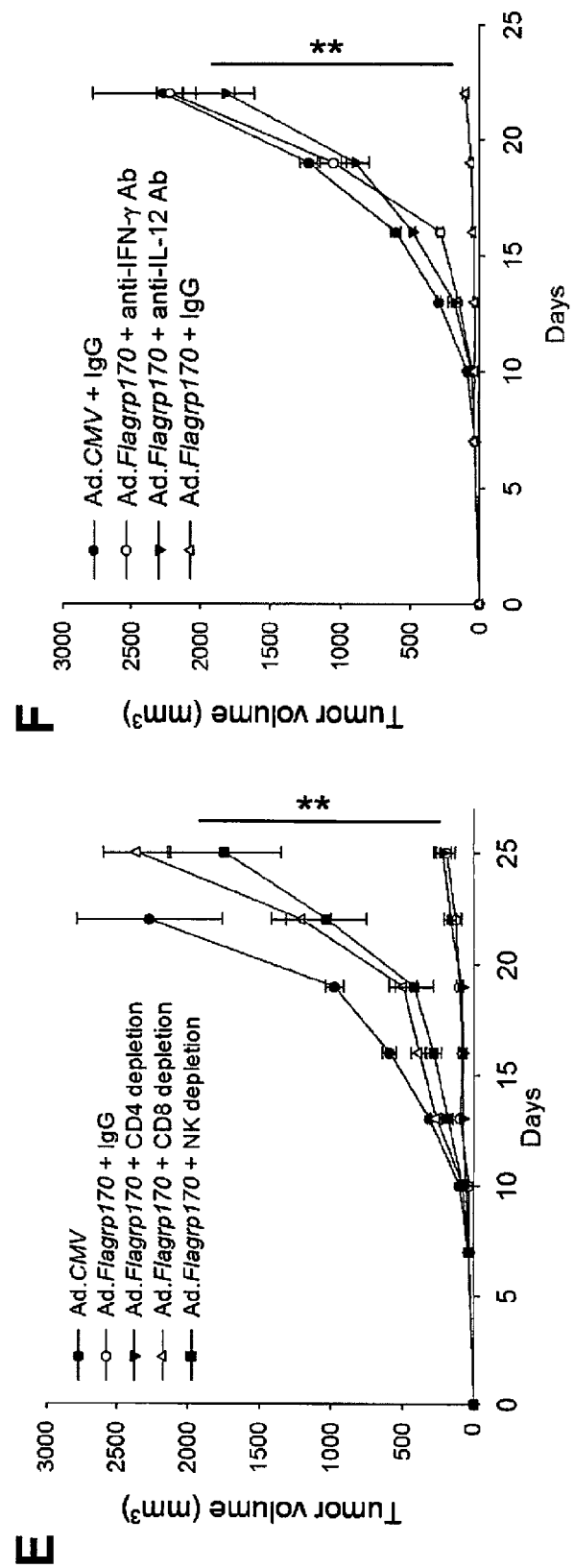
FIG. 5E. Prior to Ad.Flagrp170 therapy, tumor-bearing mice (n=5) were depleted of CD4$^+$, CD8$^+$ or NK cells using Abs. Ad.Flagrp170-treated mice receiving normal IgG and mice treated with Ad.CMV served as controls.
FIG. 5F. Injection of neutralizing Abs for IFN-γ or IL-12 abolished antitumor activity of Ad.Flagrp170.

FIG. 4 illustrates the Ad.Flagrp170 therapy promotion of immune activation in the tumor sites. A. Elevation of intratumoral IL-12p70 (x-axis ranges 0-140) and IFN-γ (y-axis ranges 0-80) in B16 tumors following Ad.Flagrp170 therapy, as determined by ELISA kits. B. Increased IFN-γ and Granzyme B production in tumor-infiltrating CD8⁺ T cells, assayed using intracellular cytokine staining. C. TUNEL assays of tumor cell death and immunofluorescence staining of CD8⁺ cells. The number of stained cells per mm² was quantified from 5 randomized visual fields (y-axis plots 0-100 CD8⁺ or 0-500 apoptotic cell count/mm²). Scale bars: 50 μm (top) or 100 μm (bottom). Data are representative of three independent experiments. *, p<0.05; **, p<0.01. Solid bars in A and C: Ad.CMV; open bars Ad.Flagellin; gray bars Ad.Grp170; striped bars Ad.Flagrp170.

Ad.Flagrp170 therapy generates a robust antigen-specific CTL response, as shown in FIG. 5. Splenocytes or lymph node cells were stimulated with tumor lysates (A. responder cell:tumor cell ratio of 1:3) or gp100$_{25-33}$ peptide (B). IFN-γ and IL-2 levels in the culture media were assessed using ELISA. Solid bars Ad.CMV; open bars Ad.Flagellin; gray bars Ad.Grp170; striped bars Ad.Flagrp170. C. Splenocytes were subjected to intracellular cytokine staining for determining the frequency of gp100$_{25-33}$-specific CTLs. D. Treated mice (n=3) were transferred with gp100$_{25-33}$-pulsed, CFSE$^{high}$ splenocytes (antigen-positive target), and non-pulsed CFSE$^{low}$ splenocytes (negative control) mixed at a ratio of 1:1. Lymph node cells were collected 16 hours later and analyzed using FACS. The numbers in parentheses indicate the percentage of target killing. E. Prior to Ad.Flagrp170 therapy, tumor-bearing mice (n=5) were depleted of CD4⁺ (solid inverted triangles), CD8⁺ (open triangles) or NK (solid squares) cells using Abs. Ad.Flagrp170-treated mice receiving normal IgG (open circles) and mice treated with Ad.CMV (solid circles) served as controls. F. Injection of neutralizing Abs for IFN-γ or IL-12 abolished antitumor activity of Ad.Flagrp170. Data shown are representative of two independent experiments. **, p<0.01.

Figures 6A, 6B:
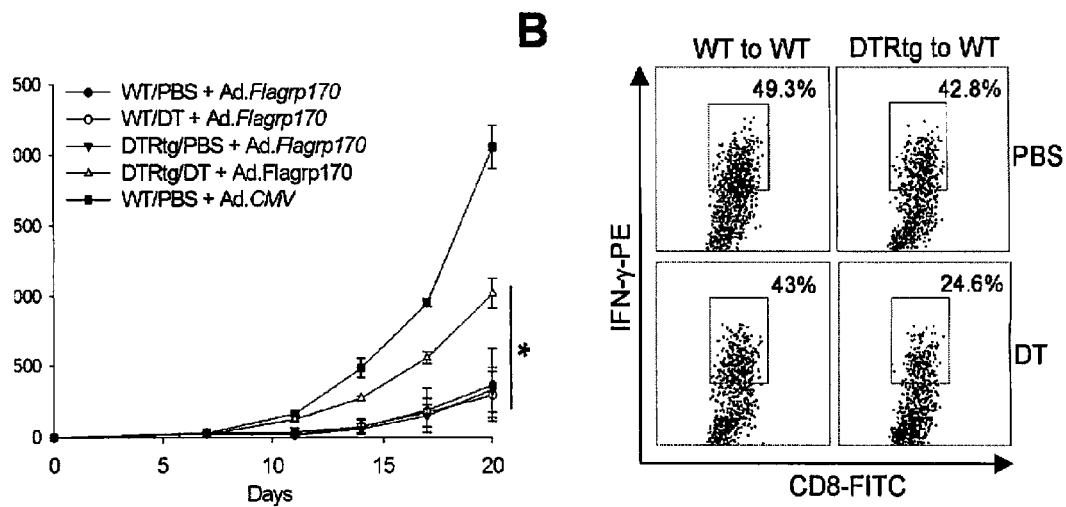
FIG. 6A. Depletion of CD11c$^+$ cells abrogated antitumor response.
FIG. 6B. Frequency of IFN-γ-producing, tumor-infiltrating CD8$^+$ cells was measured with intracellular cytokine staining.
Figures 6E, 6F:
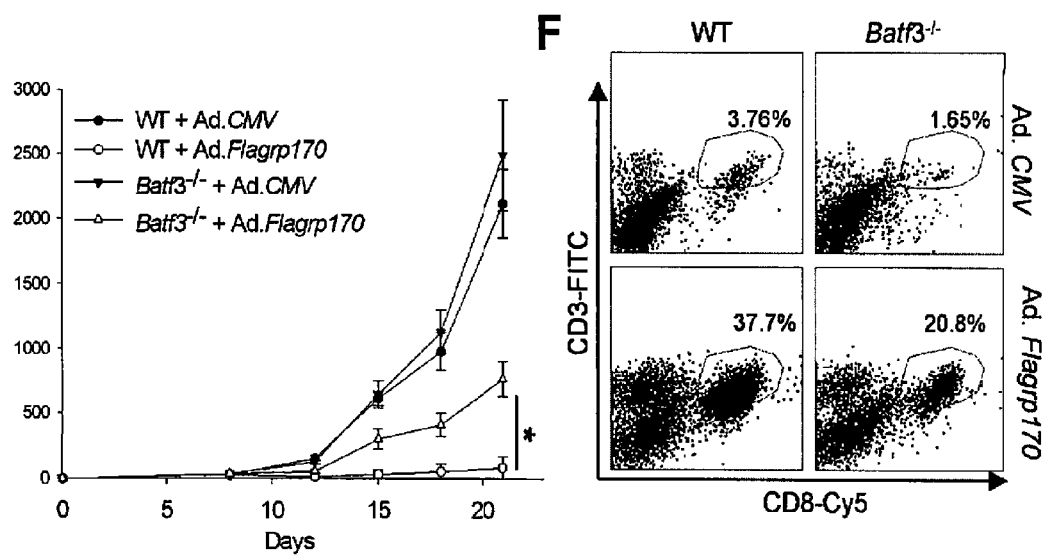
FIG. 6C. mRNA levels of intratumoral Ifnγ and Il12a were quantified using qRT-PCR.
FIG. 6D. IFN-γ and IL-2 production by gp100$_{25-33}$ peptide-stimulated splenocytes was assessed using ELISA.

FIG. 6 shows that CD11c⁺ DCs and CD8α⁺ DCs are required for the Flagrp170-enhanced CTL activation in vivo. A. Depletion of CD11c⁺ cells abrogated antitumor response. Non-Tg littermate mice (n=5) reconstituted with BM from DTRtg or non-Tg mice were treated with DTx (8 ng/g body weight) or PBS. Mice receiving BM from non-Tg mice and treated with Ad.CMV were used as control. Tumor volume is plotted on y-axis in mm³; axis scale ranges from 0-2500. WT/PBS+Ad.Flagrp170 solid circles; WT/DT+Ad.Flagrp170 open circles; DTRtg/PBS+Ad.Flagrp170 solid inverted triangles; DTRtg/DT+Ad.Flagrp170 open triangles; WT/PBS+Ad.CMV solid squares. B. Frequency of IFN-γ-producing, tumor-infiltrating CD8⁺ cells was measured with intracellular cytokine staining. C. mRNA levels of intratumoral Ifnγ and Il12a were quantified using qRT-PCR; relative levels plotted along y-axis, ranging from 0-1.4-fold. D. IFN-γ (left) and IL-2 (both in pg/ml) production by gp100$_{25-33}$ peptide-stimulated splenocytes was assessed using ELISA. In C-D bar graphs, dark bar represents WT to WT; light bar represents DTRtg to WT, E-H. Loss of CD8α⁺ DCs attenuated Flagrp170-induced antitumor effect (E; Tumor volume is plotted on y-axis in mm³; axis scale ranges from 0-3000. WT+Ad.CMV solid circles; WT+Ad.Flagrp170 open circles; Batf3$^{-/-}$+Ad.CMV solid inverted triangles; Batf3$^{-/-}$+Ad.Flagrp170 open triangles), tumor infiltration by CD8⁺ T cells (F), intratumoral Ifnγ IFN-γ mRNA levels (G), as well as cytokine (IFN-γ and IL-2; relative levels plotted along y-axis, ranging from 0-35-fold and 0-70-fold, respectively) production by splenic CD8⁺ T cells (H; pg/ml). In G-H bar graphs, dark bar represents WT; light bar represents Batf3$^{-/-}$. Data are representative of three independent experiments. *, p<0.05; NS, not significant.

Figures 7A, 7B:
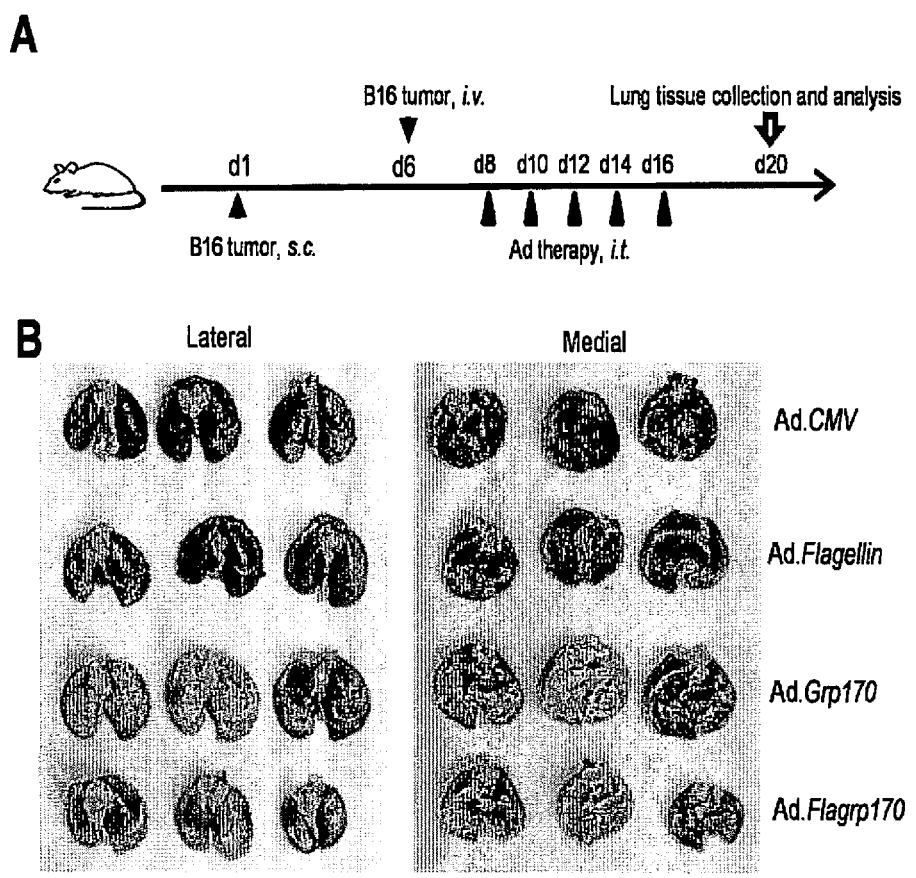
FIG. 7A. The scheme for the treatment of the experimental lung metastatic of B16-gp100 melanoma.
FIGS. 7B-7C) Mice implanted s.c. with B16-gp100 tumors on day −7; injected i.v. with B16-gp100 tumor cells on day −5 to create experimental lung metastases; starting on day 1, mice were treated by administrating adenoviruses to s.c. tumors as indicated. Gross image of lungs with metastatic tumors (B) and the number of tumor nodules on lungs are presented (C).
Figure 7C:
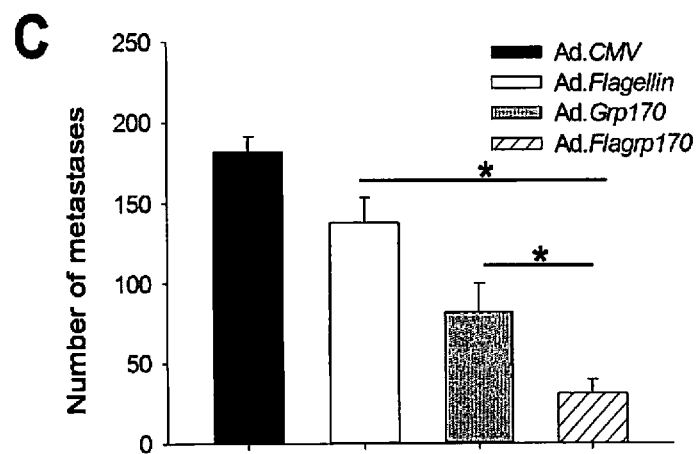
Figure 7D:
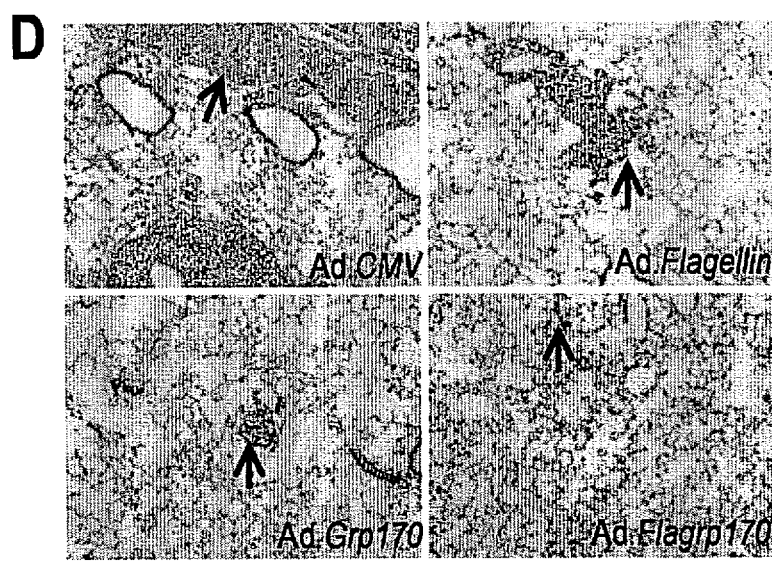
FIG. 7D. Histologic analysis of lung sections after H&E staining. Arrows indicate metastatic lesions.

FIG. 7 demonstrates that treatment of subcutaneous B16 melanoma with Ad.Flagrp170 remarkably reduces distant lung metastases. (A) The scheme for the treatment of the experimental lung metastatic of B16-gp100 melanoma. (B-C) Mice were implanted s.c. with B16-gp100 tumors on day −7. These mice were injected i.v. with B16-gp100 tumor cells on day −5 to create experimental lung metastases. Starting on day 1, mice were treated by administrating adenoviruses to s.c. tumors as indicated. Gross image of lungs with metastatic tumors (B) and the number of tumor nodules on lungs are presented (C). D. Histologic analysis of lung sections after H&E staining. Arrows indicate metastatic lesions. Data shown are from two independent experiments with similar results. *, p<0.05.

Intratumoral administration of Ad.Flagrp170 markedly inhibits the growth of weakly immunogenic TRAMP-C2 prostate tumor and murine CT26 colon tumor, as shown in FIG. 8. Mice (n=5) established with TRAMP-C2 tumors with the size of 3 mm (A) or 6 mm in diameter (B) were treated as indicated. C. Lymphocytes from TRAMP-C2 tumor-bearing mice were stimulated with irradiated TRAMP-C2 cells. IFN-γ levels in the supernatants were measured. Ad.Flagrp170 also profoundly inhibited CT-26 tumors (D) and promoted activation of AH1-specific CD8⁺ T cells (E). CT-26 tumor-free mice that rejected the secondary tumor challenge showed a potent T cell response to AH-1 peptide, as determined using ELISA assays for IFN-γ production (F). Data are representative of two independent experiments. *, p<0.05; **, p<0.01.

Figures 9A, 9B:
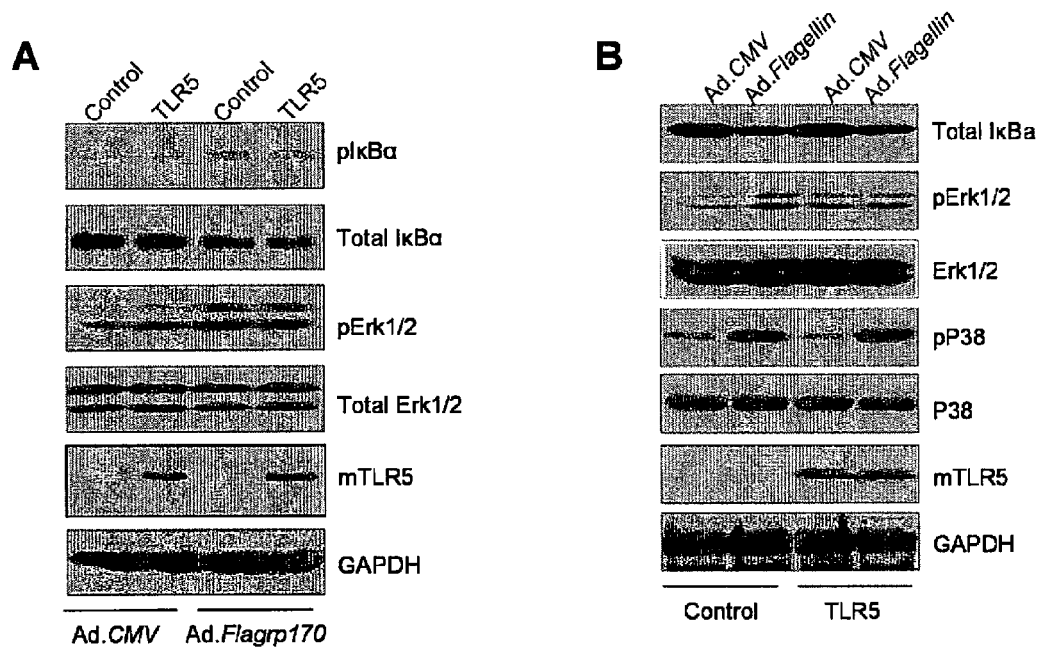
FIGS. 9A-9B. TLR5 expression has little effect on activation of NF-κB and MAPKs in bone marrow-derived DCs following adenovirus-mediated delivery of Flagrp170. BMDCs were infected with lentivirus encoding mouse TLR5 or the control virus. 24 h later, cells were treated with Ad.CMV, Ad.Flagrp170 (A) or Ad.Flagellin (B) for additional 24 h.

FIG. 9 shows that TLR5 expression has little effect on activation of NF-κB and MAPKs in bone marrow-derived DCs following adenovirus-mediated delivery of Flagrp170. BMDCs were infected with lentivirus encoding mouse TLR5 or the control virus. 24 h later, cells were treated with Ad.CMV, Ad.Flagrp170 (A) or Ad.Flagellin (B) for additional 24 h. Phosphorylation of NF-κB, Erk1/2 were determined using immunoblotting.

Figures 10A, 10B, 10C, 10D, 10E:
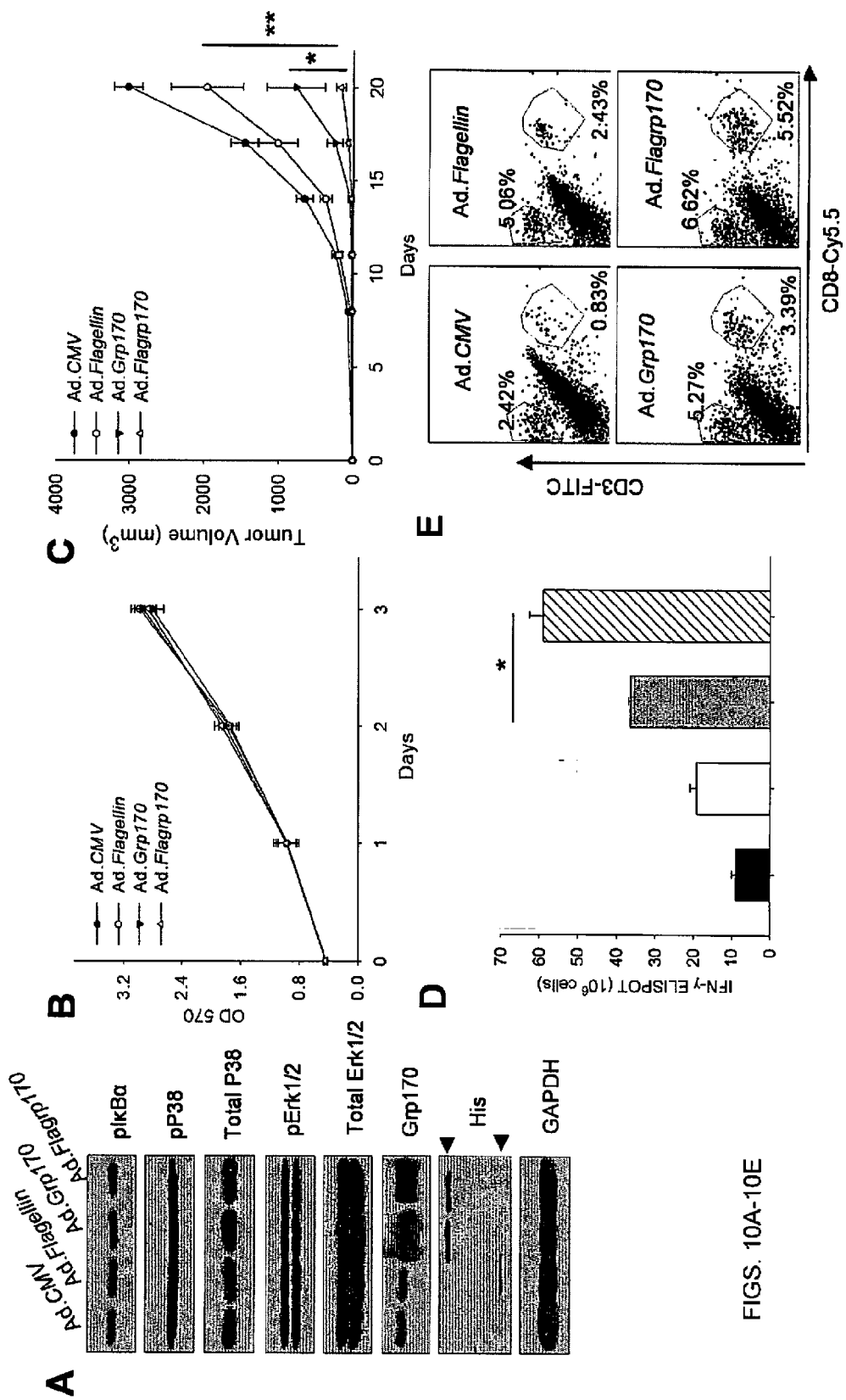
FIG. 10A. NF-κB and MAPK activation in B16 tumor cells after infection with Ad.CMV, Ad.Flagellin, Ad.Grp170 or Ad.Flagrp170 at a MOI of 100.
FIG. 10B. Flagrp170 expression does not affect B16 tumor cell growth in vitro, as determined using MTT assays.
FIG. 10C. Inhibition of the growth of Ad.Flagrp170-modified B16 tumor in vivo 48 h later, 2×10$^6$ cells were inoculated s.c. into the right flank of mice.
FIG. 10D. Tumor growth is associated with increased antigen-specific T cell activation.
FIG. 10E. Tumor-infiltration by CD8$^+$ T cells were assessed using FACS analysis.

The effects of Ad.Flagrp170 on B16 tumor cells are shown in FIG. 10. A. NF-κB and MAPK activation in B16 tumor cells after infection with Ad.CMV, Ad.Flagellin, Ad.Grp170 or Ad.Flagrp170 at a MOI of 100. B. Flagrp170 expression does not affect B16 tumor cell growth in vitro, as determined using MTT assays. C. Inhibition of the growth of Ad.Flagrp170-modified B16 tumor in vivo 48 h later, $2 \times 10^6$ cells were inoculated s.c. into the right flank of mice. (*, $p<0.05$, **, $p<0.01$). D. Tumor growth is associated with increased antigen-specific T cell activation. Splenocytes were prepared from mice bearing adenovirus-modified B16 tumors and stimulated with $gp100_{25-33}$ peptide, followed by Enzyme-linked immunosorbent spot (ELISPOT) assays for IFN-γ production (*, $p<0.05$). E. Tumor-infiltration by $CD8^+$ T cells were assessed using FACS analysis.

Figures 11A, 11B, 11C, 11D, 11E:
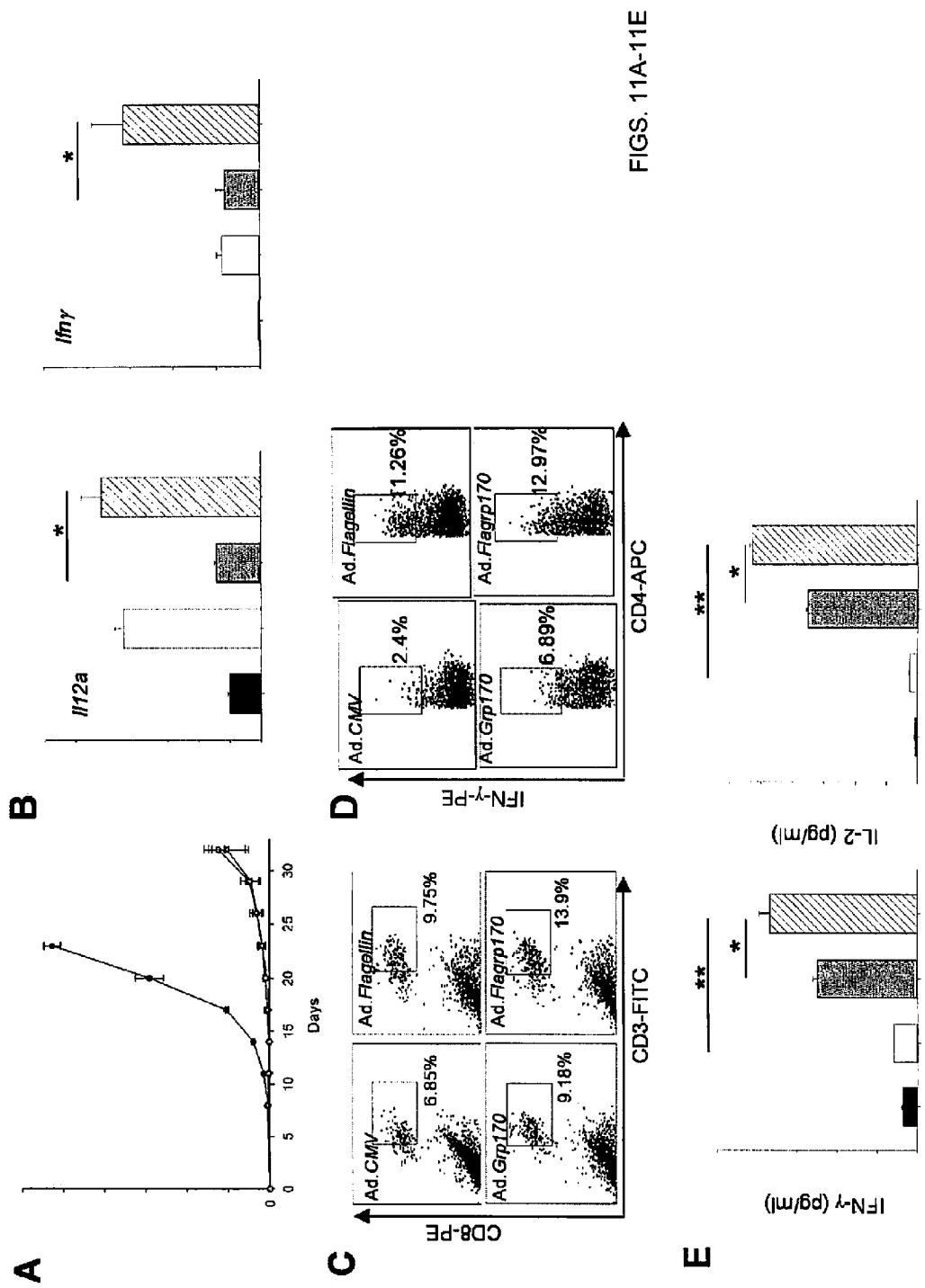
FIG. 11A. Dose effect of Ad.Flagrp170 therapy.
FIG. 11B. Increased mRNA levels of Il12a and Ifnγ in the tumor tissues, as assessed using qRT-PCR (*, p<0.05).
FIG. 11C. Increased recruitment of CD8$^+$ T cells into tumor tissues by Ad.Flagrp170 therapy, as examined using FACS analysis.
FIG. 11D. Elevated production of IFN-γ in tumor infiltrating CD4$^+$ T cells in Ad.Flagrp170-treated mice, as determined by intracellular IFN-γ staining, followed by FACS analysis.
FIG. 11E. Enhanced T cell response against melanoma antigen TRP2. Splenocytes from treated mice were stimulated with MHC I-restricted TRP2$_{180-188}$ (SVYDFFVWL) peptide.

FIG. 11 demonstrates that Ad.Flagrp170 therapy augments a potent immune response against B16 melanoma. A. Dose effect of Ad.Flagrp170 therapy. Tumor-bearing mice were treated with Ad.Flagrp170 for a total of 5 (open circles), 7 (solid inverted triangles) or 9 (open triangles) times, or with Ad.CMV (closed circles). Tumor growth was monitored (y-axis shows tumor volume in 0-3000 mm$^3$). B. Increased mRNA levels of Il12a and Ifnγ in the tumor tissues, as assessed using qRT-PCR (*, $p<0.05$). Y-axis is relative mRNA expression ranging from 0-7 in left panel and 0-200 in right panel. C. Increased recruitment of $CD8^+$ T cells into tumor tissues by Ad.Flagrp170 therapy, as examined using FACS analysis. D. Elevated production of IFN-γ in tumor infiltrating $CD4^+$ T cells in Ad.Flagrp170-treated mice, as determined by intracellular IFN-γ staining, followed by FACS analysis. E. Enhanced T cell response against melanoma antigen TRP2. Splenocytes from treated mice were stimulated with MHC I-restricted $TRP2_{180-188}$ (SVYDFFVWL) peptide. The levels of IFN-γ (pg/ml, y-axis ranges 0-2500) and IL-2 (pg/ml, y-axis ranges 0-300) in the culture media were assessed using ELISA (*, $p<0.05$, **, $p<0.01$). Data representative of two independent experiments with similar results are shown. In B and E, solid bars Ad.CMV; open bars Ad.Flagellin; gray bars Ad.Grp170; striped bars Ad.Flagrp170.

FIG. 12 shows immune activity at the tumor site. A. Recruitment of $CD8α^+CD11c^+$ and $CD11b^+F4/80^+$ cells to the tumor sites following Ad.Flagrp170 therapy. B16 tumor-bearing mice were treated with indicated adenoviruses, and cell infiltration was analyzed using FACS by gating on tumor infiltrating leukocytes. B. IL-12p70 production in tumor-infiltrating myeloid cells was measured using intracellular cytokine staining assays. $CD11c^+$ cells are not the major source of IL-12 (n=3, representative of 3 independent experiments). C. Flow cytometry analysis of splenic $CD11c^+$ cells in DTx (8 ng/kg)-treated chimera mice reconstituted with BM from DTRtg mice.

Figures 13A, 13B:
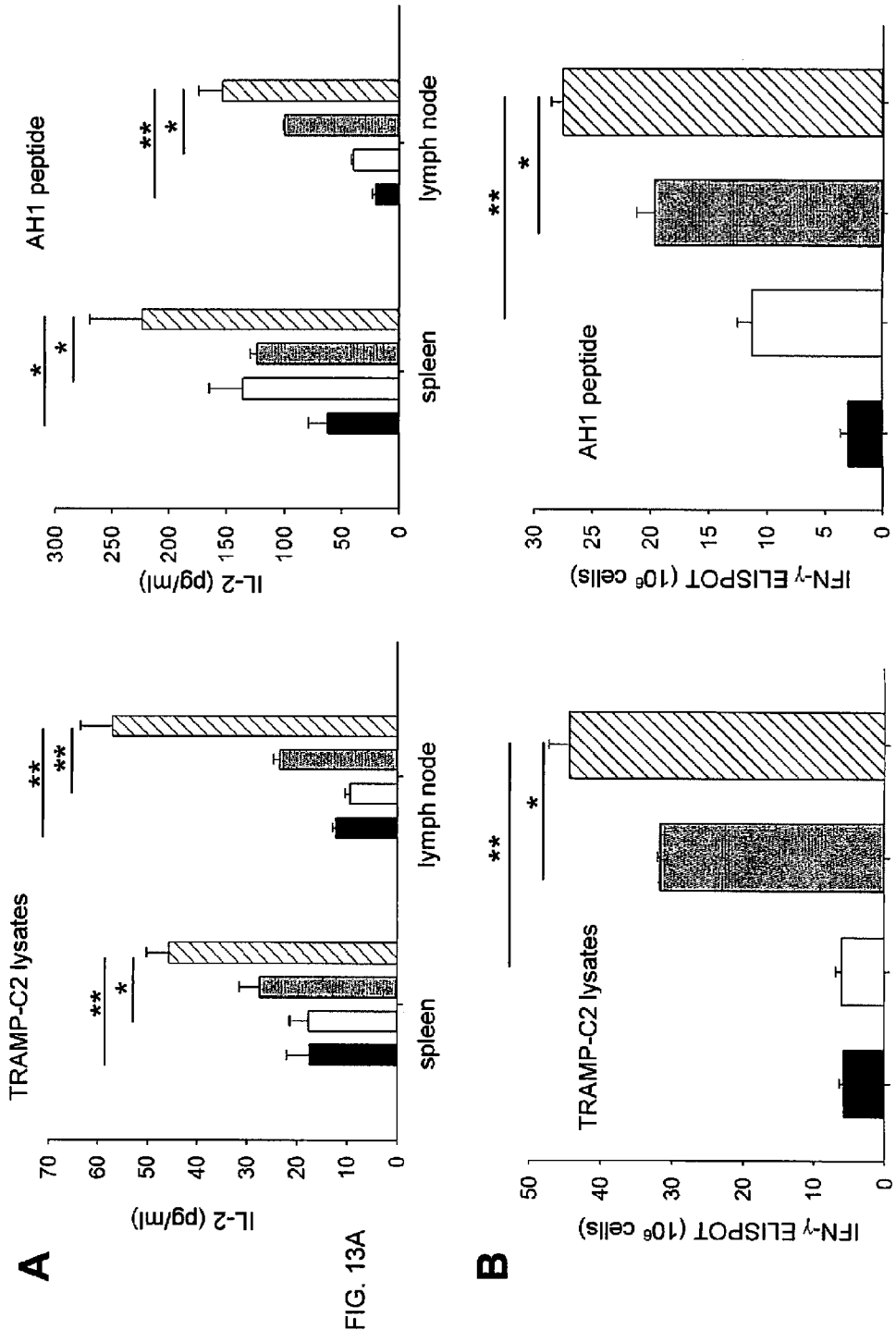
FIG. 13A. Splenocytes and lymph node cells from treated TRAMP-C2 tumor-bearing mice (left panel) or CT-26 tumor-bearing mice (right panel) stimulated with TRAMP-C2 cell lysates or AH1 peptide, respectively, followed by ELISA assays for IL-2 levels in the culture media.
FIG. 13B. ELISPOT assays of IFN-γ-producing T cells after antigen stimulation.

FIG. 13 demonstrates that Ad.Flagrp170 therapy of TRAMP-C2 prostate tumor and CT-26 tumor induces a strong tumor- or antigen-reactive immune response. A. Splenocytes and lymph node cells from treated TRAMP-C2 tumor-bearing mice (left panel) or CT-26 tumor-bearing mice (right panel) were stimulated with TRAMP-C2 cell lysates or AH1 peptide, respectively, followed by ELISA assays for IL-2 levels in the culture media. (*, $p<0.05$; **, $p<0.01$). B. ELISPOT assays of IFN-γ-producing T cells after antigen stimulation. Splenocytes from treated TRAMP-C2 tumor-bearing mice (left panel) or CT-26 tumor-bearing mice (right panel) were stimulated with TRAMP-C2 cell lysates or AH1 peptide, respectively, followed by ELISPOT assays for IFN-γ production (*, $p<0.05$; **, $p<0.01$). Data representative of two independent experiments with similar results are shown. Solid bars Ad.CMV; open bars Ad.Flagellin; gray bars Ad.Grp170; striped bars Ad.Flagrp170.

Flagrp170 Protein-Based Recombinant Vaccine Therapy

Figures 14A, 14B, 14C, 14D:
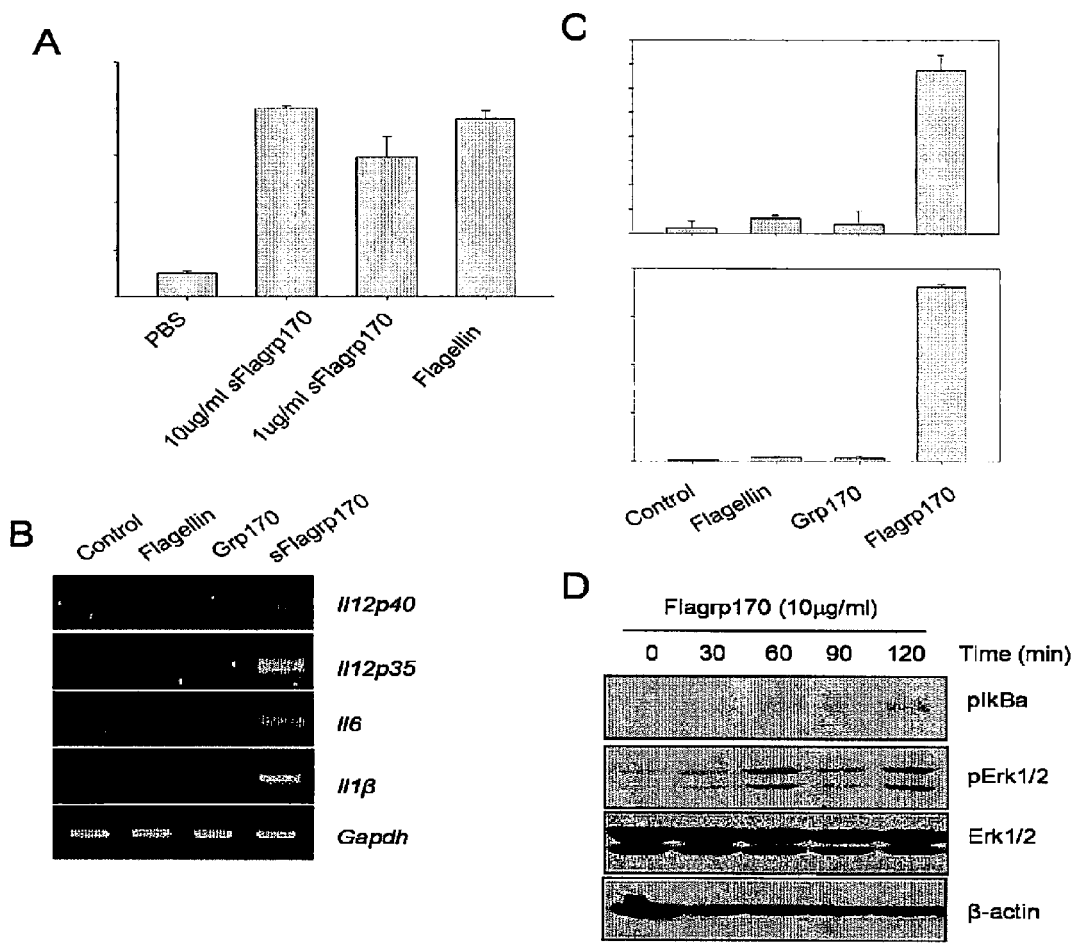
FIG. 14A. The hybrid chaperone stimulates NF-κB activation.
FIG. 14B. Upregulation of proinflammatory cytokine genes by recombinant Flagrp170 protein.
FIG. 14C. Thioglycolate-elicited mouse peritoneal macrophages were stimulated as indicated for 18 h.
FIG. 14D. Activation of NF-κB and ERK by Flagrp170 protein.

As illustrated in FIG. 14, recombinant Flagrp170 protein is highly efficient in stimulating NF-κB signaling activation and cytokine production. A. The hybrid chaperone stimulates NF-κB activation. HEK293-TLR5 cells were transfected with pGL3-NF-κB-luciferase (Luc) and treated with Flagellin or Flagrp170 at the indicated concentrations. NF-κB controlled luciferase activity was assayed using a Glomax luminometer. Relative IFN-κB activation is plotted on y-axis, 0-10. B. Upregulation of proinflammatory cytokine genes by recombinant Flagrp170 protein. Thioglycolate-elicited peritoneal macrophages were stimulated with Flagellin, Grp170 or Flagrp170 (50 μg/ml) recombinant protein as indicated for 6 h. Cells were harvested for RT-PCR analyses of IL12p40, IL12p35, IL6 and IL1β transcription. C. Thioglycolate-elicited mouse peritoneal macrophages were stimulated as indicated for 18 h. The secretion of IL-12p40 (pg/ml on upper panel, y-axis ranges 0-16) and IL-1β (pg/ml on lower panel, y-axis ranges 0-40) were measured by ELISA. D. Activation of NF-κB and ERK by Flagrp170 protein. Mouse bone marrow-derived macrophages were left untreated or stimulated with 10 μg/ml Flagrp170 protein as indicated. Cells were subjected to immunoblotting of phospho-IκBa and phospho-Erk1/2. β-actin was used as a loading control.

Figures 15A, 15B:
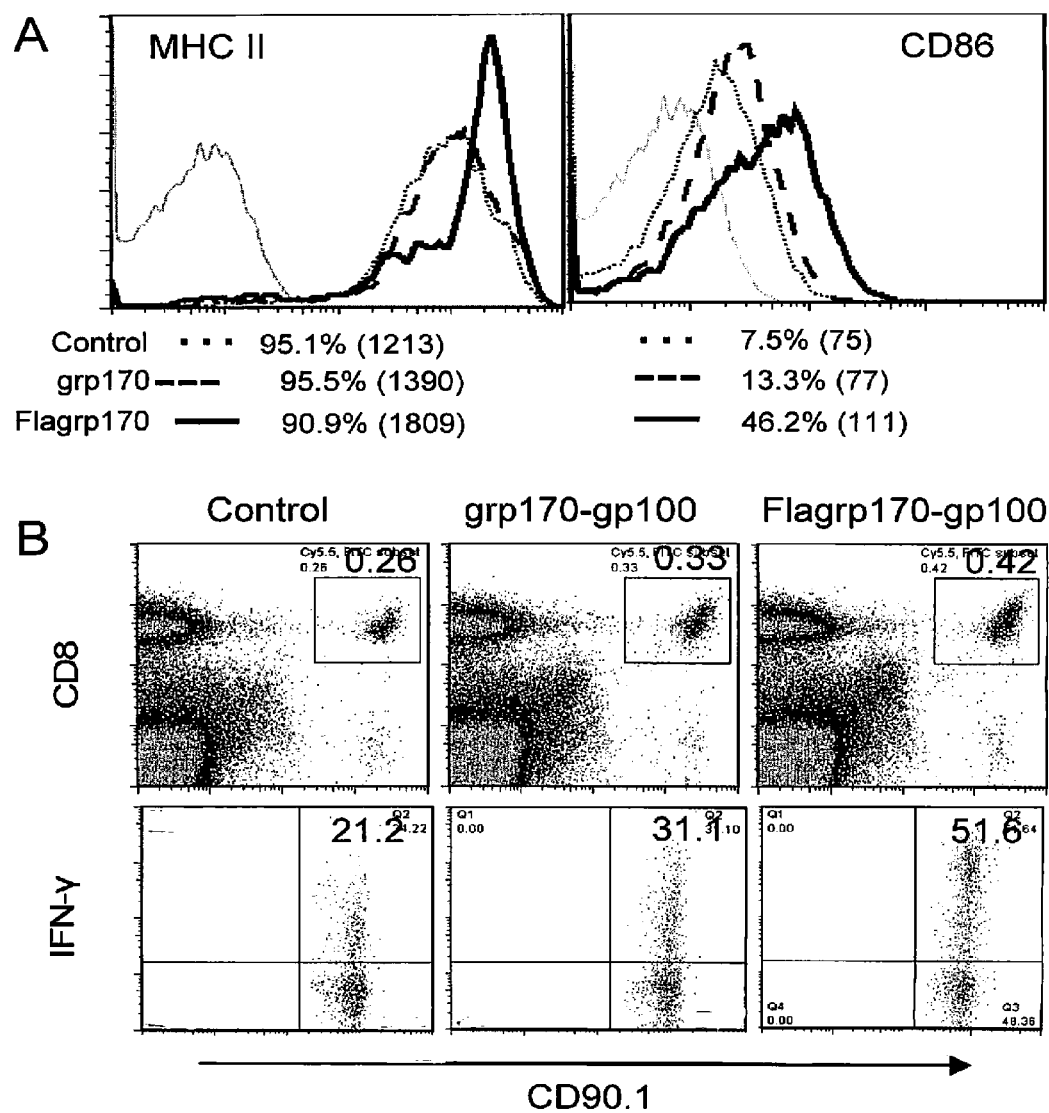
FIG. 15A. DC maturation induced by Flagrp170 protein in vivo.
FIG. 15B. Flagrp170-gp100 complex enhances T-cell priming in vivo.
Figure 16A:
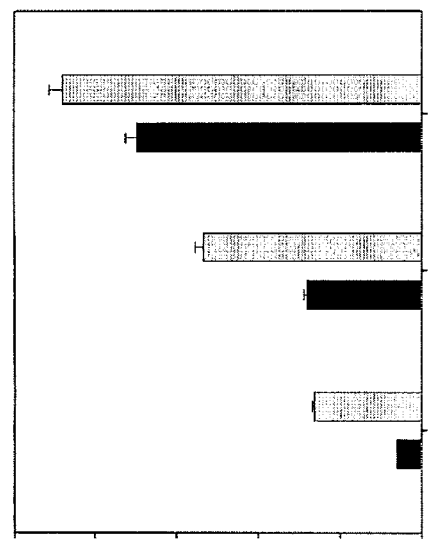
FIG. 16A. Enhanced therapeutic efficacy of Flagrp170-luc complex vaccine.
Figure 16B:
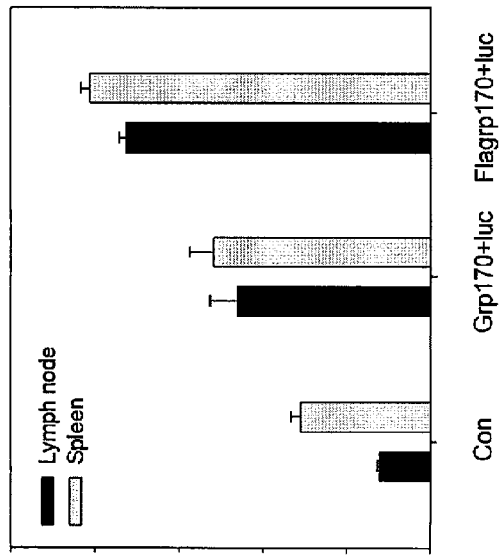
FIG. 16B. Enhanced activation of luc-specific T cells by Flagrp170-luc complex vaccine. After immunization, spleen cells were stimulated with 10 μg/ml of luc protein. ELISPOT was performed to determine the frequency of IFN-γ-producing T cells.
Figure 16C:
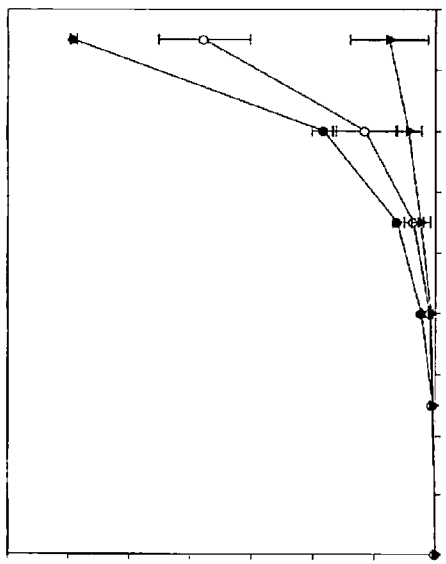
FIGS. 16C-16D. Spleen and lymph node were cocultured with irradiated dying B16-luc cells at 1:5 ratio (tumor:T cells). Culture supernatants were harvested for analysis of IL-2 levels (C) and IFN-γ levels (D) by ELISA.
Figure 16D:
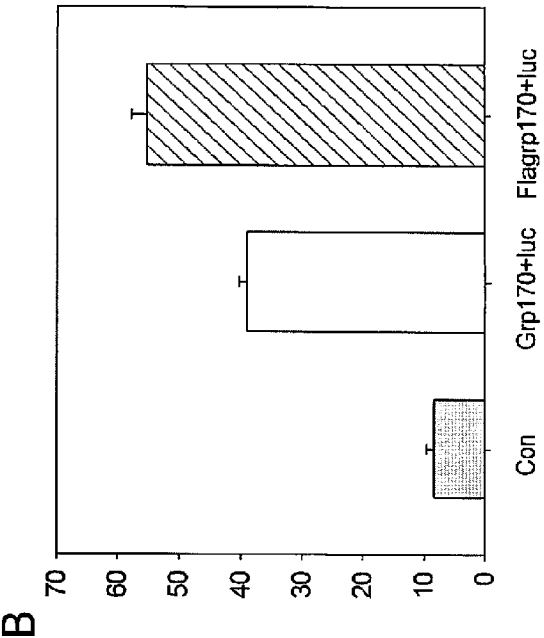

FIG. 15 shows that Flagrp170 is a potent immunostimulatory adjuvant that promotes maturation of DCs and activation of T cells reactive with tumor antigen gp100. A. DC maturation induced by Flagrp170 protein in vivo. Mice were inoculated with saline, 35 μg grp170 or Flagrp170 subcutaneously. 24 h later, draining lymph nodes (DLNs) were removed and cells were double stained for CD11c and MHC II or CD86 expression. $CD11c^+$ cells were gated for analysis by FACS. MFIs are shown in parenthesis. B. Flagrp170-gp100 complex enhances T-cell priming in vivo. Mice were i.v. adoptively transferred with gp100-specific Pmel cells ($10^7$ in 0.5 ml PBS). Mice were immunized s.c. with grp170-gp100 or Flagrp170-gp100 the next day. Single-cell suspensions were prepared from draining lymph nodes (DLNs) 5 days later, and double stained for CD8 and CD90.1 (marker for identifying Pmel cells). Proliferation of gp100-specific T-cells was assessed using FACS analysis gating on $CD8^+CD90.1^+$ cells (upper panels). Cells were stimulated with MHC I-restricted $gp100_{25-33}$ peptide for 5 h and treated with Brefeldin A (BFA). Intracellular IFN-γ was stained and analyzed by gating in $CD8^+CD90.1^+$ cells (lower panels).

FIG. 16 shows that Flagrp170 protein is more effective than Grp170 as an adjuvant in promoting an antigen-specific antitumor immune response. (A) Enhanced therapeutic efficacy of Flagrp170-luc complex vaccine. Mice were inoculated with B16-luciferase (B16-luc) tumors on day 0.5 days later, mice were immunized with 40 μg Grp170-luc complex (open circles), Flagrp170-luc complex (inverted triangles) or left untreated (solid circles). Total three treatments were administrated at 3-day intervals. Tumor growth was then followed by measuring tumor sizes. Tumor volume is plotted on y-axis in mm$^3$; axis scale ranges from 0-3500. Luc is used as a model antigen in combination with luc-expressing B16 tumor model to demonstrate the antitumor efficacy of the recombinant Flagrp170-luc complex. X-axis indicates days, from 0-18. (B) Enhanced activation of luc-specific T cells by Flagrp170-luc complex vaccine. After immunization, spleen cells were stimulated with 10 μg/ml of luc protein. ELISPOT was performed to determine the frequency of IFNγ-producing T cells. Y-axis is $10^6$ cells/well. (C, D) Spleen (light bars) and lymph node (dark bars) were cocultured with irradiated dying B16-luc cells at 1:5 ratio (tumor:T cells). Culture supernatants were harvested for analysis of IL-2 levels (C; plotted as pg/ml, y-axis ranges from 0-500) and IFN-γ levels (D; plotted as pg/ml, y-axis ranges from 0-250) by ELISA. First pair of bars indicates data from untreated contros; data from Grp170-luc complex treated mice are plotted in center pair of bars; third pair of bars indicates mice treated with Flagrp170-luc complex.

Figure 17:
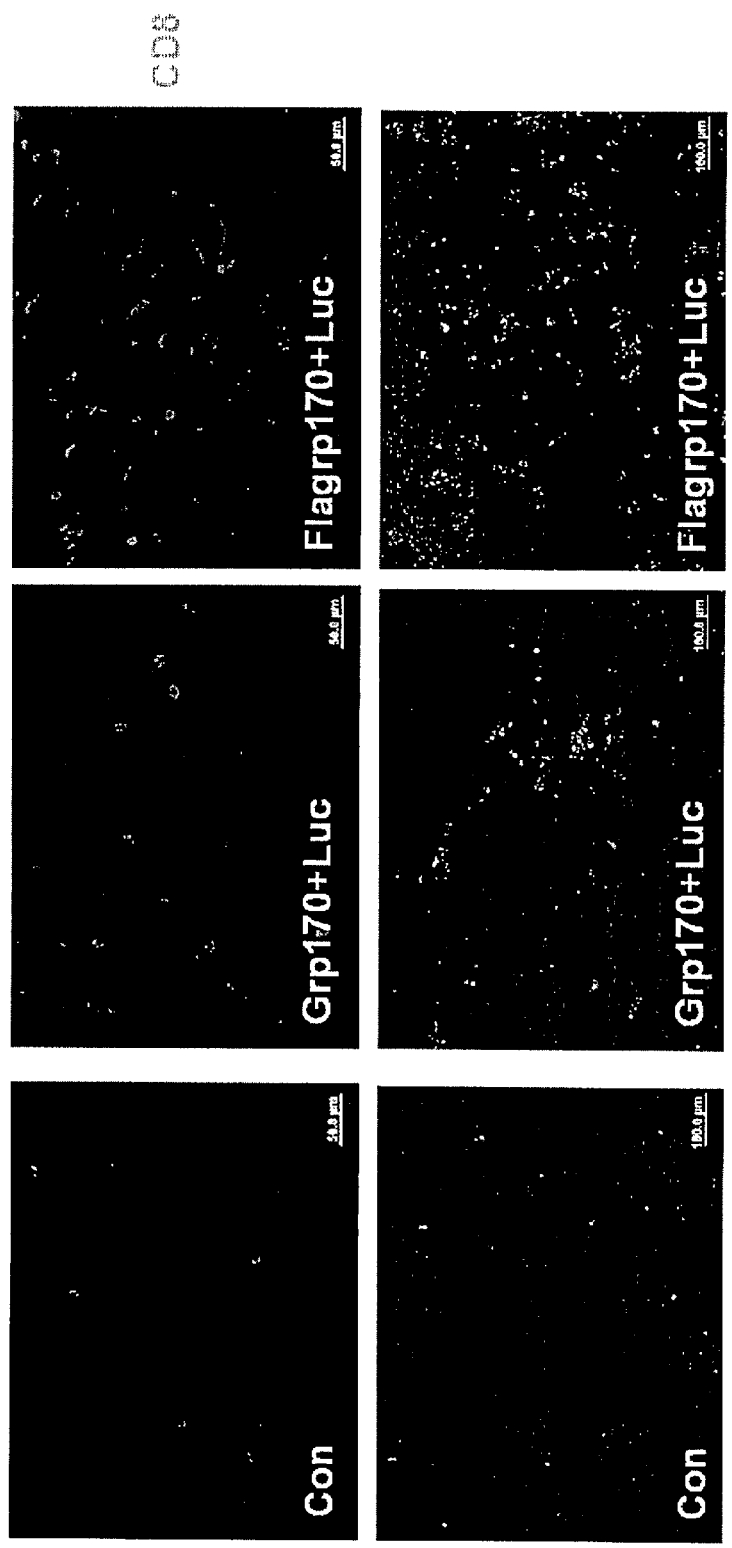
FIG. 17. Therapeutic treatment with Flagrp170-based vaccine results in a robust tumor cell death associated with a strong infiltration of CD8+ T cells. Mice bearing B16-luciferase (B16-luc) tumors were treated with Grp170-luc complex, Flagrp170-luc complex or left untreated. Tumor tissues were harvested after treatment and subjected to TUNEL assays and immunofluorescence staining for the presence of CD8+ cells.

As illustrated in FIG. 17, therapeutic treatment with Flagrp170-based vaccine results in a robust tumor cell death associated with a strong infiltration of CD8+ T cells. Mice bearing B16-luciferase (B16-luc) tumors were treated with Grp170-luc complex, Flagrp170-luc complex or left untreated. Tumor tissues were harvested after treatment and subjected to TUNEL assays (lower panels) and immunofluorescence staining for the presence of CD8+ cells (upper panels).

REFERENCES CITED IN EXAMPLE 2

1. Wang, X. Y., et al. (2006) Handb Exp Pharmacol 172, 305-329
2. Srivastava, P. (2002) Annu Rev Immunol 20, 395-425
3. Srivastava, P. (2002) Nat Rev Immunol 2, 185-194
4. Wang, X. Y., et al. (2000) Immunol Invest 29, 131-137
5. Wang, X. Y., et al. (2006) Handb Exp Pharmacol, 305-329
6. Calderwood, S. K., et al. (2005) Eur J Immunol 35, 2518-2527
7. Murshid, A., et al. (2008) Expert Rev Vaccines 7, 1019-1030
8. Wang, X.-Y., et al. (2007) Large mammalian hsp70 family proteins, hsp110 and grp170, and their roles in biology and cancer therapy Vol. 7, Springer, New York
9. Wang, X. Y., et al. (2001) J Immunol 166, 490-497
10. Park, J., et al. (2003) Biochemistry 42, 14893-14902
11. Wang, X. Y., et al. (2006) J Immunol 177, 1543-1551
12. Wang, X. Y., et al. (2010) J Immunol 184, 6309-6319
13. Wang, X. Y., et al. (2003) Int J Cancer 105, 226-231
14. Wang, X. Y., et al. (2010) J Immunol 184
15. Park, J. E., et al. (2006) Cancer Res 66, 1161-1168
16. Gao, P., et al. (2009) Cancer Immunol Immunother 58, 1319-1328
17. Gao, P., et al. (2008) Cancer Res 68, 3890-3898
18. Arnouk, H., et al. (2010) Int J Hyperthermia 26, 366-375
19. Wang, X. Y., et al. (2004) Methods 32, 13-20
20. Park, J., et al. (2006) Cancer Res 66, 1161-1168
21. Akira, S., and Takeda, K. (2004) Nat. Rev. Immunol. 4, 499-511
22. Medzhitov, R., and Janeway, C. A., Jr. (2002) Science 296, 298-300
23. van Duin, D., et al. (2006) Trends in Immunology 27, 49-55
24. Murthy, K. G. K., et al. (2004) Journal of Biological Chemistry 279, 5667-5675
25. Lowy, J., and Hanson, J. (1964) Nature 202, 538-540
26. Hayashi, F., et al. (2001) Nature 410, 1099-1103

Example 3: Combining Tumor-Specific Oncolytic Destruction and Immune Activation Using a Flagrp170-Based Oncolytic Virus The tumor microenvironment (TME) is a well-known and formidable obstacle to solid cancer treatment. Immune evasion within the TME is also one of emerging hallmarks of cancer, which must be addressed for any new immunotherapies. Replication-selective oncolytic viruses engineered to specifically destroy cancer cells without toxicity to normal tissue represents a promising and unique anticancer therapeutic approach. Antitumor activity and safety profiles of replication-competent adenoviruses controlled by specific promoters (e.g., the human telomerase reverse transcriptase, hTERT) have been demonstrated in several phase I clinical trials in patients with advanced solid tumors. Virus replication-mediated tumor lysis strategically coupled with remodeling of TME with a novel chimeric immunochaperone Flagrp170 should result in highly immunogenic cancer cell death and restoration of innate and adaptive antitumor immune responses. This innovative in situ oncolytic vaccine (ISOV) specifically targets the TME for priming polyclonal populations of T lymphocytes against the entire repertoire of cancer-specific neoantigens.

Figure 18:
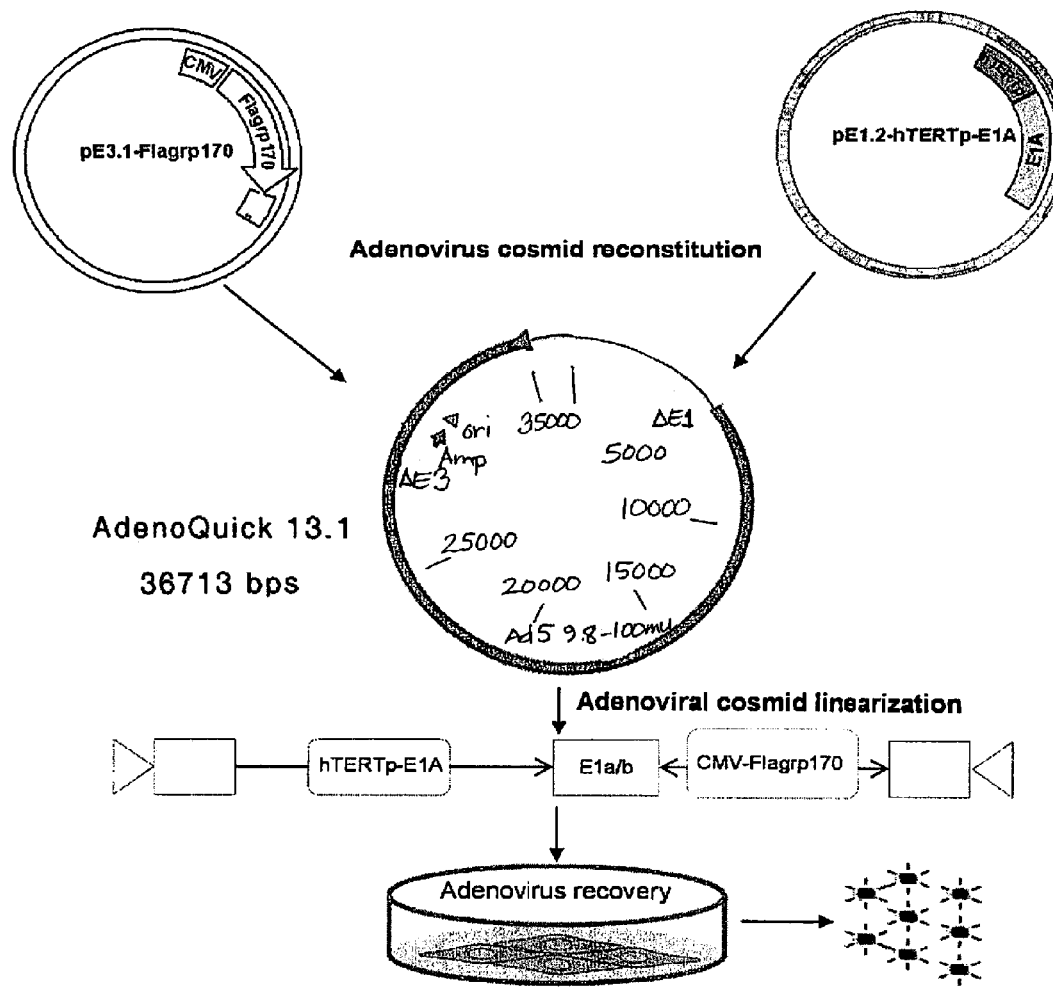
FIG. 18. Schematic illustration of construction of bipartite Ad-hTERTp-E1A-CMV-Flagrp170 adenovirus.

Construction of Bipartite Ad-hTERTp-E1A-CMV-Flagrp170 Adenovirus:

As illustrated in FIG. 18, a hTERT promoter-directed oncolytic adenovirus with concurrent expression of adenovirus early region 1A (E1A) proteins and the chimeric Flagrp170 can be constructed using the AdenoQuick cloning system from OD260, Inc. (Biose, Id.). This system enables construction of bipartite adenoviruses that contain two shuttle vectors (pE1.2 and pE3.1) which carrying independent expression cassettes and can be inserted into the E1 and E3 regions of adenovirus genome. Briefly, hTERT promoter-driven E1A expression cassette is cloned into pE1.2 shutter vector. Similarly, CMV promoter-driven Flagrp170 expression cassette is inserted into the pE3.1 vector. The plasmids pE1.2-hTERTp-E1A and pE3.1-CMV-Flagrp170 are digested with AlwNI and DraIII respectively and the purified fragments are ligated with SfiI-digested AdenoQuick13.1 plasmid simultaneously. The resultant ligated products are packaged into phage lambda particles using MaxPlax packaging extract and transformed into TOP10 E. coli competent cells. After selection with kanamycin and ampicillin, the PacI linearized cosmid extracted from the bacteria can be transfected into 293A cells to rescue the recombinant adenovirus. Additionally, Ad-hTERTp-E1A, Ad-CMV-Flagrp170 or Ad.null adenoviruses can also be made using Adeno-X Adenoviral Expression System (BD Bioscience).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A polypeptide produced by the method of:
    culturing a host cell comprising a fusion construct operably linked to an expression control sequence under conditions suitable for production of a protein encoded by the fusion construct, and
    recovering the protein,
    wherein the fusion construct comprises a polynucleotide encoding an NF-κB-activating domain of Flagellin in operable linkage with a polynucleotide encoding an ATP-binding domain truncated Grp170, and wherein the NF-κB-activating domain of Flagellin comprises N-terminal amino acids 2-175 and C-terminal amino acids 402-495 of SEQ ID NO: 8, and the ATP-binding domain truncated Grp170 consists of amino acids 431-994 of SEQ ID NO: 2 or 3.

2. A polypeptide comprising an NF-κB-activating domain of Flagellin fused with a polynucleotide encoding an ATP-binding domain truncated Grp170, wherein the NF-κB-activating domain of Flagellin comprises N-terminal amino acids 2-175 and C-terminal amino acids 402-495 of SEQ ID NO: 8, and the ATP-binding domain truncated Grp170 consists of amino acids 431-994 of SEQ ID NO: 2 or 3.

3. An immunogenic composition comprising the polypeptide of claim 2.

4. The polypeptide of claim 2, which has the amino acid sequence of SEQ ID NO: 1.

5. The composition of claim 3, wherein the polypeptide is non-covalently complexed with an additional immunogenic polypeptide.

* * * * *

SEQUENCE LISTING

<160> NUMBER OF SEQ ID NOS: 11

<210> SEQ ID NO 1
<211> LENGTH: 920
<212> TYPE: PRT
<213> ORGANISM: Artificial Sequence
<220> FEATURE:
<223> OTHER INFORMATION: recombinant fusion construct -continued

```
<400> SEQUENCE: 1

Met Ala Ala Thr Val Arg Arg Gln Arg Pro Arg Arg Leu Leu Cys Trp
1               5                   10                  15

Ala Leu Val Ala Val Leu Leu Ala Asp Leu Leu Ala Leu Ser Asp Thr
            20                  25                  30

Leu Ala Ala Gln Val Ile Asn Thr Asn Ser Leu Ser Leu Leu Thr Gln
        35                  40                  45

Asn Asn Leu Asn Lys Ser Gln Ser Ala Leu Gly Thr Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ala Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ala Val Gln Ser Ala Asn Ser Thr Asn Ser Gln Ser Asp Leu Asp Ser
    130                 135                 140

Ile Gln Ala Glu Ile Thr Gln Arg Leu Asn Glu Ile Asp Arg Val Ser
145                 150                 155                 160

Gly Gln Thr Gln Phe Asn Gly Val Lys Val Leu Ala Gln Asp Asn Thr
                165                 170                 175

Leu Thr Ile Gln Val Gly Ala Asn Asp Gly Glu Thr Ile Asp Ile Asp
            180                 185                 190

Leu Lys Gln Ile Asn Ser Gln Thr Leu Gly Leu Asp Thr Leu Asn Val
        195                 200                 205

Ser Pro Gly Ile Ser Gly Gly Gly Ile Leu Asp Ser Met Gly
    210                 215                 220

Ala Thr Thr Thr Glu Asn Pro Leu Gln Lys Ile Asp Ala Ala Leu Ala
225                 230                 235                 240

Gln Val Asp Thr Leu Arg Ser Asp Leu Gly Ala Val Gln Asn Arg Phe
                245                 250                 255

Asn Ser Ala Ile Thr Asn Leu Gly Asn Thr Val Asn Asn Leu Thr Ser
            260                 265                 270

Ala Arg Ser Arg Ile Glu Asp Ser Asp Tyr Ala Thr Glu Val Ser Asn
        275                 280                 285

Met Ser Arg Ala Gln Ile Leu Gln Gln Ala Gly Thr Ser Val Leu Ala
    290                 295                 300

Gln Ala Asn Gln Val Pro Gln Asn Val Leu Ser Leu Leu Arg Gly Ser
305                 310                 315                 320

Gly Leu Ala Glu Ala Ala Lys Glu Ala Ala Lys Glu Ala Ala
                325                 330                 335

Ala Lys Glu Ala Ala Lys Ala Ala Ala Gly Glu Phe Lys Val Lys
        340                 345                 350

Pro Phe Val Val Arg Asp Ala Val Ile Tyr Pro Ile Leu Val Glu Phe
    355                 360                 365

Thr Arg Glu Val Glu Glu Pro Gly Leu Arg Ser Leu Lys His Asn
        370                 375                 380

Lys Arg Val Leu Phe Ser Arg Met Gly Pro Tyr Pro Gln Arg Lys Val
385                 390                 395                 400

Ile Thr Phe Asn Arg Tyr Ser His Asp Phe Asn Phe His Ile Asn Tyr
                405                 410                 415
```

-continued

```
Gly Asp Leu Gly Phe Leu Gly Pro Glu Asp Leu Arg Val Phe Gly Ser
            420                 425                 430

Gln Asn Leu Thr Thr Val Lys Leu Lys Gly Val Gly Glu Ser Phe Lys
            435                 440                 445

Lys Tyr Pro Asp Tyr Glu Ser Lys Gly Ile Lys Ala His Phe Asn Leu
            450                 455                 460

Asp Glu Ser Gly Val Leu Ser Leu Asp Arg Val Glu Ser Val Phe Glu
465                 470                 475                 480

Thr Leu Val Glu Asp Ser Pro Glu Glu Glu Ser Thr Leu Thr Lys Leu
                    485                 490                 495

Gly Asn Thr Ile Ser Ser Leu Phe Gly Gly Thr Ser Ser Asp Ala
                    500                 505                 510

Lys Glu Asn Gly Thr Asp Ala Val Gln Glu Glu Glu Ser Pro Ala
                    515                 520                 525

Glu Gly Ser Lys Asp Glu Pro Ala Glu Gln Gly Glu Leu Lys Glu Glu
            530                 535                 540

Ala Glu Pro Pro Ala Glu Glu Thr Ser Gln Pro Pro Ser Glu Pro
545                 550                 555                 560

Lys Gly Asp Ala Ala Arg Glu Gly Glu Lys Pro Asp Glu Lys Glu Ser
                    565                 570                 575

Gly Asp Lys Pro Glu Ala Gln Lys Pro Asn Glu Lys Gly Gln Ala Gly
                    580                 585                 590

Pro Glu Gly Ala Ala Pro Ala Pro Glu Glu Asp Lys Lys Pro Lys Pro
                    595                 600                 605

Ala Arg Lys Gln Lys Met Val Glu Glu Ile Gly Val Glu Leu Ala Val
            610                 615                 620

Leu Asp Leu Pro Asp Leu Pro Glu Asp Glu Leu Ala Arg Ser Val Gln
625                 630                 635                 640

Lys Leu Glu Glu Leu Thr Leu Arg Asp Leu Glu Lys Gln Glu Arg Glu
                    645                 650                 655

Lys Ala Ala Asn Ser Leu Glu Ala Phe Ile Phe Glu Thr Gln Asp Lys
            660                 665                 670

Leu Tyr Gln Pro Glu Tyr Gln Glu Val Ser Thr Glu Glu Gln Arg Glu
            675                 680                 685

Glu Ile Ser Gly Lys Leu Ser Ala Thr Ser Thr Trp Leu Glu Asp Glu
            690                 695                 700

Gly Phe Gly Ala Thr Thr Val Met Leu Lys Asp Lys Leu Ala Glu Leu
705                 710                 715                 720

Arg Lys Leu Cys Gln Gly Leu Phe Phe Arg Val Glu Glu Arg Arg Lys
                    725                 730                 735

Trp Pro Glu Arg Leu Ser Ala Leu Asp Asn Leu Leu Asn His Ser Ser
                    740                 745                 750

Ile Phe Leu Lys Gly Ala Arg Leu Ile Pro Glu Met Asp Gln Val Phe
            755                 760                 765

Thr Glu Val Glu Met Thr Thr Leu Glu Lys Val Ile Asn Asp Thr Trp
            770                 775                 780

Ala Trp Lys Asn Ala Thr Leu Ala Glu Gln Ala Lys Leu Pro Ala Thr
785                 790                 795                 800

Glu Lys Pro Val Leu Leu Ser Lys Asp Ile Glu Ala Lys Met Met Ala
                    805                 810                 815

Leu Asp Arg Glu Val Gln Tyr Leu Leu Asn Lys Ala Lys Phe Thr Lys
            820                 825                 830
```

```
Pro Arg Pro Arg Pro Lys Asp Lys Asn Gly Thr Arg Ala Glu Pro Pro
        835                 840                 845

Leu Asn Ala Ser Ala Gly Asp Gln Glu Glu Lys Val Ile Pro Pro Ala
850                 855                 860

Gly Gln Thr Glu Glu Ala Lys Pro Ile Leu Glu Pro Asp Lys Glu Glu
865                 870                 875                 880

Thr Gly Thr Glu Pro Ala Asp Ser Glu Pro Leu Glu Leu Gly Gly Pro
                885                 890                 895

Gly Ala Gly Pro Glu Gln Glu Gln Ser Ala Gly Gln Lys Arg Pro
                900                 905                 910

Ser His His His His His Gly
        915                 920

<210> SEQ ID NO 2
<211> LENGTH: 999
<212> TYPE: PRT
<213> ORGANISM: Mus musculus

<400> SEQUENCE: 2

Met Ala Ala Thr Val Arg Arg Gln Arg Pro Arg Arg Leu Leu Cys Trp
1               5                   10                  15

Ala Leu Val Ala Val Leu Leu Ala Asp Leu Leu Ala Leu Ser Asp Thr
                20                  25                  30

Leu Ala Val Met Ser Val Asp Leu Gly Ser Glu Ser Met Lys Val Ala
            35                  40                  45

Ile Val Lys Pro Gly Val Pro Met Glu Ile Val Leu Asn Lys Glu Ser
        50                  55                  60

Arg Arg Lys Thr Pro Val Thr Val Thr Leu Lys Glu Asn Glu Arg Phe
65                  70                  75                  80

Leu Gly Asp Ser Ala Ala Gly Met Ala Ile Lys Asn Pro Lys Ala Thr
                85                  90                  95

Leu Arg Tyr Phe Gln His Leu Leu Gly Lys Gln Ala Asp Asn Pro His
            100                 105                 110

Val Ala Leu Tyr Arg Ser Arg Phe Pro Glu His Glu Leu Ile Val Asp
        115                 120                 125

Pro Gln Arg Gln Thr Val Arg Phe Gln Ile Ser Pro Gln Leu Gln Phe
130                 135                 140

Ser Pro Glu Glu Val Leu Gly Met Val Leu Asn Tyr Ser Arg Ser Leu
145                 150                 155                 160

Ala Glu Asp Phe Ala Glu Gln Pro Ile Lys Asp Ala Val Ile Thr Val
                165                 170                 175

Pro Ala Phe Phe Asn Gln Ala Glu Arg Arg Ala Val Leu Gln Ala Ala
            180                 185                 190

Arg Met Ala Gly Leu Lys Val Leu Gln Leu Ile Asn Asp Asn Thr Ala
        195                 200                 205

Thr Ala Leu Ser Tyr Gly Val Phe Arg Arg Lys Asp Ile Asn Ser Thr
    210                 215                 220

Ala Gln Asn Val Met Phe Tyr Asp Met Gly Ser Gly Ser Thr Val Cys
225                 230                 235                 240

Thr Ile Val Thr Tyr Gln Thr Val Lys Thr Lys Glu Ala Gly Met Gln
                245                 250                 255

Pro Gln Leu Gln Ile Arg Gly Val Gly Phe Asp Arg Thr Leu Gly Gly
            260                 265                 270

Leu Glu Met Glu Leu Arg Leu Arg Glu His Leu Ala Lys Leu Phe Asn
        275                 280                 285
```

-continued

```
Glu Gln Arg Lys Gly Gln Lys Ala Lys Asp Val Arg Glu Asn Pro Arg
    290                 295                 300

Ala Met Ala Lys Leu Leu Arg Glu Ala Asn Arg Leu Lys Thr Val Leu
305                 310                 315                 320

Ser Ala Asn Ala Asp His Met Ala Gln Ile Glu Gly Leu Met Asp Asp
                325                 330                 335

Val Asp Phe Lys Ala Lys Val Thr Arg Val Glu Phe Glu Glu Leu Cys
            340                 345                 350

Ala Asp Leu Phe Asp Arg Val Pro Gly Pro Val Gln Gln Ala Leu Gln
        355                 360                 365

Ser Ala Glu Met Ser Leu Asp Gln Ile Glu Gln Val Ile Leu Val Gly
    370                 375                 380

Gly Ala Thr Arg Val Pro Lys Val Gln Glu Val Leu Leu Lys Ala Val
385                 390                 395                 400

Gly Lys Glu Glu Leu Gly Lys Asn Ile Asn Ala Asp Glu Ala Ala Ala
                405                 410                 415

Met Gly Ala Val Tyr Gln Ala Ala Leu Ser Lys Ala Phe Lys Val
            420                 425                 430

Lys Pro Phe Val Val Arg Asp Ala Val Ile Tyr Pro Ile Leu Val Glu
        435                 440                 445

Phe Thr Arg Glu Val Glu Glu Pro Gly Leu Arg Ser Leu Lys His
    450                 455                 460

Asn Lys Arg Val Leu Phe Ser Arg Met Gly Pro Tyr Pro Gln Arg Lys
465                 470                 475                 480

Val Ile Thr Phe Asn Arg Tyr Ser His Asp Phe Asn Phe His Ile Asn
                485                 490                 495

Tyr Gly Asp Leu Gly Phe Leu Gly Pro Glu Asp Leu Arg Val Phe Gly
            500                 505                 510

Ser Gln Asn Leu Thr Thr Val Lys Leu Lys Gly Val Gly Glu Ser Phe
        515                 520                 525

Lys Lys Tyr Pro Asp Tyr Glu Ser Lys Gly Ile Lys Ala His Phe Asn
    530                 535                 540

Leu Asp Glu Ser Gly Val Leu Ser Leu Asp Arg Val Glu Ser Val Phe
545                 550                 555                 560

Glu Thr Leu Val Glu Asp Ser Pro Glu Glu Ser Thr Leu Thr Lys
                565                 570                 575

Leu Gly Asn Thr Ile Ser Ser Leu Phe Gly Gly Thr Ser Ser Asp
            580                 585                 590

Ala Lys Glu Asn Gly Thr Asp Ala Val Gln Glu Glu Glu Ser Pro
        595                 600                 605

Ala Glu Gly Ser Lys Asp Glu Pro Ala Glu Gln Gly Glu Leu Lys Glu
    610                 615                 620

Glu Ala Glu Pro Pro Ala Glu Thr Ser Gln Pro Pro Ser Glu
625                 630                 635                 640

Pro Lys Gly Asp Ala Ala Arg Glu Gly Glu Lys Pro Asp Glu Lys Glu
                645                 650                 655

Ser Gly Asp Lys Pro Glu Ala Gln Lys Pro Asn Glu Lys Gly Gln Ala
            660                 665                 670

Gly Pro Glu Gly Ala Ala Pro Ala Pro Glu Glu Asp Lys Lys Pro Lys
        675                 680                 685

Pro Ala Arg Lys Gln Lys Met Val Glu Glu Ile Gly Val Glu Leu Ala
    690                 695                 700
```

Val Leu Asp Leu Pro Asp Leu Pro Glu Asp Glu Leu Ala Arg Ser Val
705                 710                 715                 720

Gln Lys Leu Glu Glu Leu Thr Leu Arg Asp Leu Glu Lys Gln Glu Arg
            725                 730                 735

Glu Lys Ala Ala Asn Ser Leu Glu Ala Phe Ile Phe Glu Thr Gln Asp
        740                 745                 750

Lys Leu Tyr Gln Pro Glu Tyr Gln Glu Val Ser Thr Glu Glu Gln Arg
    755                 760                 765

Glu Glu Ile Ser Gly Lys Leu Ser Ala Thr Ser Thr Trp Leu Glu Asp
770                 775                 780

Glu Gly Phe Gly Ala Thr Thr Val Met Leu Lys Asp Lys Leu Ala Glu
785                 790                 795                 800

Leu Arg Lys Leu Cys Gln Gly Leu Phe Phe Arg Val Glu Glu Arg Arg
            805                 810                 815

Lys Trp Pro Glu Arg Leu Ser Ala Leu Asp Asn Leu Leu Asn His Ser
        820                 825                 830

Ser Ile Phe Leu Lys Gly Ala Arg Leu Ile Pro Glu Met Asp Gln Val
    835                 840                 845

Phe Thr Glu Val Glu Met Thr Thr Leu Glu Lys Val Ile Asn Asp Thr
850                 855                 860

Trp Ala Trp Lys Asn Ala Thr Leu Ala Glu Gln Ala Lys Leu Pro Ala
865                 870                 875                 880

Thr Glu Lys Pro Val Leu Leu Ser Lys Asp Ile Glu Ala Lys Met Met
            885                 890                 895

Ala Leu Asp Arg Glu Val Gln Tyr Leu Leu Asn Lys Ala Lys Phe Thr
        900                 905                 910

Lys Pro Arg Pro Arg Pro Lys Asp Lys Asn Gly Thr Arg Ala Glu Pro
    915                 920                 925

Pro Leu Asn Ala Ser Ala Gly Asp Gln Glu Glu Lys Val Ile Pro Pro
930                 935                 940

Ala Gly Gln Thr Glu Glu Ala Lys Pro Ile Leu Glu Pro Asp Lys Glu
945                 950                 955                 960

Glu Thr Gly Thr Glu Pro Ala Asp Ser Glu Pro Leu Glu Leu Gly Gly
            965                 970                 975

Pro Gly Ala Gly Pro Glu Gln Glu Gln Ser Ala Gly Gln Lys Arg
        980                 985                 990

Pro Ser Lys Asn Asp Glu Leu
    995

<210> SEQ ID NO 3
<211> LENGTH: 999
<212> TYPE: PRT
<213> ORGANISM: Homo sapiens

<400> SEQUENCE: 3

Met Ala Asp Lys Val Arg Arg Gln Arg Pro Arg Arg Val Cys Trp
1               5                   10                  15

Ala Leu Val Ala Val Leu Leu Ala Asp Leu Leu Ala Leu Ser Asp Thr
            20                  25                  30

Leu Ala Val Met Ser Val Asp Leu Gly Ser Glu Ser Met Lys Val Ala
        35                  40                  45

Ile Val Lys Pro Gly Val Pro Met Glu Ile Val Leu Asn Lys Glu Ser
    50                  55                  60

Arg Arg Lys Thr Pro Val Ile Val Thr Leu Lys Glu Asn Glu Arg Phe
65                  70                  75                  80

```
Phe Gly Asp Ser Ala Ala Ser Met Ala Ile Lys Asn Pro Lys Ala Thr
                85                  90                  95
Leu Arg Tyr Phe Gln His Leu Leu Gly Lys Gln Ala Asp Asn Pro His
            100                 105                 110
Val Ala Leu Tyr Gln Ala Arg Phe Pro Glu His Glu Leu Thr Phe Asp
        115                 120                 125
Pro Gln Arg Gln Thr Val His Phe Gln Ile Ser Ser Gln Leu Gln Phe
130                 135                 140
Ser Pro Glu Glu Val Leu Gly Met Val Leu Asn Tyr Ser Arg Ser Leu
145                 150                 155                 160
Ala Glu Asp Phe Ala Glu Gln Pro Ile Lys Asp Ala Val Ile Thr Val
                165                 170                 175
Pro Val Phe Phe Asn Gln Ala Glu Arg Arg Ala Val Leu Gln Ala Ala
            180                 185                 190
Arg Met Ala Gly Leu Lys Val Leu Gln Leu Ile Asn Asp Asn Thr Ala
        195                 200                 205
Thr Ala Leu Ser Tyr Gly Val Phe Arg Arg Lys Asp Ile Asn Thr Thr
210                 215                 220
Ala Gln Asn Ile Met Phe Tyr Asp Met Gly Ser Gly Ser Thr Val Cys
225                 230                 235                 240
Thr Ile Val Thr Tyr Gln Met Val Lys Thr Lys Glu Ala Gly Met Gln
                245                 250                 255
Pro Gln Leu Gln Ile Arg Gly Val Gly Phe Asp Arg Thr Leu Gly Gly
            260                 265                 270
Leu Glu Met Glu Leu Arg Leu Arg Glu Arg Leu Ala Gly Leu Phe Asn
        275                 280                 285
Glu Gln Arg Lys Gly Gln Arg Ala Lys Asp Val Arg Glu Asn Pro Arg
290                 295                 300
Ala Met Ala Lys Leu Leu Arg Glu Ala Asn Arg Leu Lys Thr Val Leu
305                 310                 315                 320
Ser Ala Asn Ala Asp His Met Ala Gln Ile Glu Gly Leu Met Asp Asp
                325                 330                 335
Val Asp Phe Lys Ala Lys Val Thr Arg Val Glu Phe Glu Glu Leu Cys
            340                 345                 350
Ala Asp Leu Phe Glu Arg Val Pro Gly Pro Val Gln Gln Ala Leu Gln
        355                 360                 365
Ser Ala Glu Met Ser Leu Asp Glu Ile Glu Gln Val Ile Leu Val Gly
370                 375                 380
Gly Ala Thr Arg Val Pro Arg Val Gln Glu Val Leu Leu Lys Ala Val
385                 390                 395                 400
Gly Lys Glu Glu Leu Gly Lys Asn Ile Asn Ala Asp Glu Ala Ala Ala
                405                 410                 415
Met Gly Ala Val Tyr Gln Ala Ala Ala Leu Ser Lys Ala Phe Lys Val
            420                 425                 430
Lys Pro Phe Val Val Arg Asp Ala Val Val Tyr Pro Ile Leu Val Glu
        435                 440                 445
Phe Thr Arg Glu Val Glu Glu Pro Gly Ile His Ser Leu Lys His
450                 455                 460
Asn Lys Arg Val Leu Phe Ser Arg Met Gly Pro Tyr Pro Gln Arg Lys
465                 470                 475                 480
Val Ile Thr Phe Asn Arg Tyr Ser His Asp Phe Asn Phe His Ile Asn
                485                 490                 495
```

-continued

Tyr Gly Asp Leu Gly Phe Leu Gly Pro Glu Asp Leu Arg Val Phe Gly
              500                 505                 510

Ser Gln Asn Leu Thr Thr Val Lys Leu Lys Gly Val Gly Asp Ser Phe
          515                 520                 525

Lys Lys Tyr Pro Asp Tyr Glu Ser Lys Gly Ile Lys Ala His Phe Asn
      530                 535                 540

Leu Asp Glu Ser Gly Val Leu Ser Leu Asp Arg Val Glu Ser Val Phe
545                 550                 555                 560

Glu Thr Leu Val Glu Asp Ser Ala Glu Glu Ser Thr Leu Thr Lys
                  565                 570                 575

Leu Gly Asn Thr Ile Ser Ser Leu Phe Gly Gly Thr Thr Pro Asp
              580                 585                 590

Ala Lys Glu Asn Gly Thr Asp Thr Val Gln Glu Glu Glu Ser Pro
          595                 600                 605

Ala Glu Gly Ser Lys Asp Glu Pro Gly Glu Gln Val Glu Leu Lys Glu
      610                 615                 620

Glu Ala Glu Ala Pro Val Glu Asp Gly Ser Gln Pro Pro Pro Glu
625                 630                 635                 640

Pro Lys Gly Asp Ala Thr Pro Glu Gly Glu Lys Ala Thr Glu Lys Glu
                  645                 650                 655

Asn Gly Asp Lys Ser Glu Ala Gln Lys Pro Ser Glu Lys Ala Glu Ala
              660                 665                 670

Gly Pro Glu Gly Val Ala Pro Glu Gly Glu Lys Gln Lys
          675                 680                 685

Pro Ala Arg Lys Arg Met Val Glu Ile Gly Val Glu Leu Val
      690                 695                 700

Val Leu Asp Leu Pro Asp Leu Pro Glu Asp Lys Leu Ala Gln Ser Val
705                 710                 715                 720

Gln Lys Leu Gln Asp Leu Thr Leu Arg Asp Leu Glu Lys Gln Glu Arg
                  725                 730                 735

Glu Lys Ala Ala Asn Ser Leu Glu Ala Phe Ile Phe Glu Thr Gln Asp
              740                 745                 750

Lys Leu Tyr Gln Pro Glu Tyr Gln Glu Val Ser Thr Glu Glu Gln Arg
          755                 760                 765

Glu Glu Ile Ser Gly Lys Leu Ser Ala Ala Ser Thr Trp Leu Glu Asp
      770                 775                 780

Glu Gly Val Gly Ala Thr Thr Val Met Leu Lys Lys Leu Ala Glu
785                 790                 795                 800

Leu Arg Lys Leu Cys Gln Gly Leu Phe Phe Arg Val Glu Glu Arg Lys
                  805                 810                 815

Lys Trp Pro Glu Arg Leu Ser Ala Leu Asp Asn Leu Leu Asn His Ser
              820                 825                 830

Ser Met Phe Leu Lys Gly Ala Arg Leu Ile Pro Glu Met Asp Gln Ile
          835                 840                 845

Phe Thr Glu Val Glu Met Thr Thr Leu Glu Lys Val Ile Asn Glu Thr
      850                 855                 860

Trp Ala Trp Lys Asn Ala Thr Leu Ala Glu Gln Ala Lys Leu Pro Ala
865                 870                 875                 880

Thr Glu Lys Pro Val Leu Leu Ser Lys Asp Ile Glu Ala Lys Met Met
                  885                 890                 895

Ala Leu Asp Arg Glu Val Gln Tyr Leu Leu Asn Lys Ala Lys Phe Thr
              900                 905                 910

Lys Pro Arg Pro Arg Pro Lys Asp Lys Asn Gly Thr Arg Ala Glu Pro

```
                915                 920                 925
Pro Leu Asn Ala Ser Ala Ser Asp Gln Gly Glu Lys Val Ile Pro Pro
    930                 935                 940

Ala Gly Gln Thr Glu Asp Ala Glu Pro Ile Ser Glu Pro Glu Lys Val
945                 950                 955                 960

Glu Thr Gly Ser Glu Pro Gly Asp Thr Glu Pro Leu Glu Leu Gly Gly
                965                 970                 975

Pro Gly Ala Glu Pro Glu Gln Lys Glu Gln Ser Thr Gly Gln Lys Arg
            980                 985                 990

Pro Leu Lys Asn Asp Glu Leu
        995

<210> SEQ ID NO 4
<211> LENGTH: 34
<212> TYPE: PRT
<213> ORGANISM: Mus musculus

<400> SEQUENCE: 4

Met Ala Ala Thr Val Arg Arg Gln Arg Pro Arg Arg Leu Leu Cys Trp
1               5                   10                  15

Ala Leu Val Ala Val Leu Leu Ala Asp Leu Leu Ala Leu Ser Asp Thr
            20                  25                  30

Leu Ala

<210> SEQ ID NO 5
<211> LENGTH: 34
<212> TYPE: PRT
<213> ORGANISM: Homo sapiens

<400> SEQUENCE: 5

Met Ala Asp Lys Val Arg Arg Gln Arg Pro Arg Arg Val Cys Trp
1               5                   10                  15

Ala Leu Val Ala Val Leu Leu Ala Asp Leu Leu Ala Leu Ser Asp Thr
            20                  25                  30

Leu Ala

<210> SEQ ID NO 6
<211> LENGTH: 564
<212> TYPE: PRT
<213> ORGANISM: Mus musculus

<400> SEQUENCE: 6

Lys Val Lys Pro Phe Val Val Arg Asp Ala Val Ile Tyr Pro Ile Leu
1               5                   10                  15

Val Glu Phe Thr Arg Glu Val Glu Glu Pro Gly Leu Arg Ser Leu
            20                  25                  30

Lys His Asn Lys Arg Val Leu Phe Ser Arg Met Gly Pro Tyr Pro Gln
        35                  40                  45

Arg Lys Val Ile Thr Phe Asn Arg Tyr Ser His Asp Phe Asn Phe His
    50                  55                  60

Ile Asn Tyr Gly Asp Leu Gly Phe Leu Gly Pro Glu Asp Leu Arg Val
65                  70                  75                  80

Phe Gly Ser Gln Asn Leu Thr Thr Val Lys Leu Lys Gly Val Gly Glu
                85                  90                  95

Ser Phe Lys Lys Tyr Pro Asp Tyr Glu Ser Lys Gly Ile Lys Ala His
            100                 105                 110

Phe Asn Leu Asp Glu Ser Gly Val Leu Ser Leu Asp Arg Val Glu Ser
```

-continued

```
            115                 120                 125
Val Phe Glu Thr Leu Val Glu Asp Ser Pro Glu Glu Ser Thr Leu
        130                 135                 140
Thr Lys Leu Gly Asn Thr Ile Ser Ser Leu Phe Gly Gly Thr Ser
145                 150                 155                 160
Ser Asp Ala Lys Glu Asn Gly Thr Asp Ala Val Gln Glu Glu Glu
                165                 170                 175
Ser Pro Ala Glu Gly Ser Lys Asp Glu Pro Ala Glu Gln Gly Glu Leu
                180                 185                 190
Lys Glu Glu Ala Glu Pro Pro Ala Glu Thr Ser Gln Pro Pro
                195                 200                 205
Ser Glu Pro Lys Gly Asp Ala Ala Arg Glu Gly Glu Lys Pro Asp Glu
                210                 215                 220
Lys Glu Ser Gly Asp Lys Pro Glu Ala Gln Lys Pro Asn Glu Lys Gly
225                 230                 235                 240
Gln Ala Gly Pro Glu Gly Ala Ala Pro Ala Pro Glu Glu Asp Lys Lys
                245                 250                 255
Pro Lys Pro Ala Arg Lys Gln Lys Met Val Glu Glu Ile Gly Val Glu
                260                 265                 270
Leu Ala Val Leu Asp Leu Pro Asp Leu Pro Glu Asp Glu Leu Ala Arg
                275                 280                 285
Ser Val Gln Lys Leu Glu Glu Leu Thr Leu Arg Asp Leu Glu Lys Gln
                290                 295                 300
Glu Arg Glu Lys Ala Ala Asn Ser Leu Glu Ala Phe Ile Phe Glu Thr
305                 310                 315                 320
Gln Asp Lys Leu Tyr Gln Pro Glu Tyr Gln Glu Val Ser Thr Glu Glu
                325                 330                 335
Gln Arg Glu Glu Ile Ser Gly Lys Leu Ser Ala Thr Ser Thr Trp Leu
                340                 345                 350
Glu Asp Glu Gly Phe Gly Ala Thr Thr Val Met Leu Lys Asp Lys Leu
                355                 360                 365
Ala Glu Leu Arg Lys Leu Cys Gln Gly Leu Phe Phe Arg Val Glu Glu
                370                 375                 380
Arg Arg Lys Trp Pro Glu Arg Leu Ser Ala Leu Asp Asn Leu Leu Asn
385                 390                 395                 400
His Ser Ser Ile Phe Leu Lys Gly Ala Arg Leu Ile Pro Glu Met Asp
                405                 410                 415
Gln Val Phe Thr Glu Val Glu Met Thr Thr Leu Glu Lys Val Ile Asn
                420                 425                 430
Asp Thr Trp Ala Trp Lys Asn Ala Thr Leu Ala Glu Gln Ala Lys Leu
                435                 440                 445
Pro Ala Thr Glu Lys Pro Val Leu Leu Ser Lys Asp Ile Glu Ala Lys
                450                 455                 460
Met Met Ala Leu Asp Arg Glu Val Gln Tyr Leu Leu Asn Lys Ala Lys
465                 470                 475                 480
Phe Thr Lys Pro Arg Pro Arg Pro Lys Asp Lys Asn Gly Thr Arg Ala
                485                 490                 495
Glu Pro Pro Leu Asn Ala Ser Ala Gly Asp Gln Glu Glu Lys Val Ile
                500                 505                 510
Pro Pro Ala Gly Gln Thr Glu Glu Ala Lys Pro Ile Leu Glu Pro Asp
                515                 520                 525
Lys Glu Glu Thr Gly Thr Glu Pro Ala Asp Ser Glu Pro Leu Glu Leu
                530                 535                 540
```

Gly Gly Pro Gly Ala Gly Pro Glu Gln Glu Gln Ser Ala Gly Gln
545                 550                 555                 560

Lys Arg Pro Ser

<210> SEQ ID NO 7
<211> LENGTH: 564
<212> TYPE: PRT
<213> ORGANISM: Homo sapiens

<400> SEQUENCE: 7

Lys Val Lys Pro Phe Val Val Arg Asp Ala Val Val Tyr Pro Ile Leu
1               5                   10                  15

Val Glu Phe Thr Arg Glu Val Glu Glu Pro Gly Ile His Ser Leu
            20                  25                  30

Lys His Asn Lys Arg Val Leu Phe Ser Arg Met Gly Pro Tyr Pro Gln
        35                  40                  45

Arg Lys Val Ile Thr Phe Asn Arg Tyr Ser His Asp Phe Asn Phe His
    50                  55                  60

Ile Asn Tyr Gly Asp Leu Gly Phe Leu Gly Pro Glu Asp Leu Arg Val
65                  70                  75                  80

Phe Gly Ser Gln Asn Leu Thr Thr Val Lys Leu Lys Gly Val Gly Asp
                85                  90                  95

Ser Phe Lys Lys Tyr Pro Asp Tyr Glu Ser Lys Gly Ile Lys Ala His
            100                 105                 110

Phe Asn Leu Asp Glu Ser Gly Val Leu Ser Leu Asp Arg Val Glu Ser
        115                 120                 125

Val Phe Glu Thr Leu Val Glu Asp Ser Ala Glu Glu Ser Thr Leu
    130                 135                 140

Thr Lys Leu Gly Asn Thr Ile Ser Ser Leu Phe Gly Gly Gly Thr Thr
145                 150                 155                 160

Pro Asp Ala Lys Glu Asn Gly Thr Asp Thr Val Gln Glu Glu Glu
                165                 170                 175

Ser Pro Ala Glu Gly Ser Lys Asp Glu Pro Gly Glu Gln Val Glu Leu
            180                 185                 190

Lys Glu Glu Ala Glu Ala Pro Val Glu Asp Gly Ser Gln Pro Pro
        195                 200                 205

Pro Glu Pro Lys Gly Asp Ala Thr Pro Glu Gly Glu Lys Ala Thr Glu
    210                 215                 220

Lys Glu Asn Gly Asp Lys Ser Glu Ala Gln Lys Pro Ser Glu Lys Ala
225                 230                 235                 240

Glu Ala Gly Pro Glu Gly Val Ala Pro Ala Pro Glu Gly Glu Lys Lys
                245                 250                 255

Gln Lys Pro Ala Arg Lys Arg Arg Met Val Glu Glu Ile Gly Val Glu
            260                 265                 270

Leu Val Val Leu Asp Leu Pro Asp Leu Pro Glu Asp Lys Leu Ala Gln
        275                 280                 285

Ser Val Gln Lys Leu Gln Asp Leu Thr Leu Arg Asp Leu Glu Lys Gln
    290                 295                 300

Glu Arg Glu Lys Ala Ala Asn Ser Leu Glu Ala Phe Ile Phe Glu Thr
305                 310                 315                 320

Gln Asp Lys Leu Tyr Gln Pro Glu Tyr Gln Glu Val Ser Thr Glu Glu
                325                 330                 335

Gln Arg Glu Glu Ile Ser Gly Lys Leu Ser Ala Ala Ser Thr Trp Leu
            340                 345                 350

```
Glu Asp Glu Gly Val Gly Ala Thr Thr Val Met Leu Lys Glu Lys Leu
            355                 360                 365

Ala Glu Leu Arg Lys Leu Cys Gln Gly Leu Phe Phe Arg Val Glu Glu
370                 375                 380

Arg Lys Lys Trp Pro Glu Arg Leu Ser Ala Leu Asp Asn Leu Leu Asn
385                 390                 395                 400

His Ser Ser Met Phe Leu Lys Gly Ala Arg Leu Ile Pro Glu Met Asp
                405                 410                 415

Gln Ile Phe Thr Glu Val Glu Met Thr Thr Leu Glu Lys Val Ile Asn
                420                 425                 430

Glu Thr Trp Ala Trp Lys Asn Ala Thr Leu Ala Glu Gln Ala Lys Leu
            435                 440                 445

Pro Ala Thr Glu Lys Pro Val Leu Leu Ser Lys Asp Ile Glu Ala Lys
450                 455                 460

Met Met Ala Leu Asp Arg Glu Val Gln Tyr Leu Leu Asn Lys Ala Lys
465                 470                 475                 480

Phe Thr Lys Pro Arg Pro Arg Pro Lys Asp Lys Asn Gly Thr Arg Ala
                485                 490                 495

Glu Pro Pro Leu Asn Ala Ser Ser Asp Gln Gly Leu Lys Val Ile
            500                 505                 510

Pro Pro Ala Gly Gln Thr Glu Asp Ala Glu Pro Ile Ser Glu Pro Glu
            515                 520                 525

Lys Val Glu Thr Gly Ser Glu Pro Gly Asp Thr Glu Pro Leu Glu Leu
530                 535                 540

Gly Gly Pro Gly Ala Glu Pro Glu Gln Lys Glu Gln Ser Thr Gly Gln
545                 550                 555                 560

Lys Arg Pro Leu

<210> SEQ ID NO 8
<211> LENGTH: 495
<212> TYPE: PRT
<213> ORGANISM: Salmonella enterica serovar Typhimurium LT2

<400> SEQUENCE: 8

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ala Asn Ile Lys Gly Leu Thr Gln Ala
50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160
```

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
                485                 490                 495

<210> SEQ ID NO 9
<211> LENGTH: 284
<212> TYPE: PRT
<213> ORGANISM: Artificial Sequence
<220> FEATURE:
<223> OTHER INFORMATION: fusion construct

<400> SEQUENCE: 9

Ala Gln Val Ile Asn Thr Asn Ser Leu Ser Leu Leu Thr Gln Asn Asn
1               5                   10                  15

Leu Asn Lys Ser Gln Ser Ala Leu Gly Thr Ala Ile Glu Arg Leu Ser
            20                  25                  30

```
Ser Gly Leu Arg Ile Asn Ser Ala Lys Asp Asp Ala Ala Gly Gln Ala
        35                  40                  45
Ile Ala Asn Arg Phe Thr Ala Asn Ile Lys Gly Leu Thr Gln Ala Ser
        50                  55                  60
Arg Asn Ala Asn Asp Gly Ile Ser Ile Ala Gln Thr Thr Glu Gly Ala
65                      70                  75                  80
Leu Asn Glu Ile Asn Asn Asn Leu Gln Arg Val Arg Glu Leu Ala Val
                85                  90                  95
Gln Ser Ala Asn Ser Thr Asn Ser Gln Ser Asp Leu Asp Ser Ile Gln
                100                 105                 110
Ala Glu Ile Thr Gln Arg Leu Asn Glu Ile Asp Arg Val Ser Gly Gln
                115                 120                 125
Thr Gln Phe Asn Gly Val Lys Val Leu Ala Gln Asp Asn Thr Leu Thr
        130                 135                 140
Ile Gln Val Gly Ala Asn Asp Gly Glu Thr Ile Asp Ile Asp Leu Lys
145                 150                 155                 160
Gln Ile Asn Ser Gln Thr Leu Gly Leu Asp Thr Leu Asn Val Ser Pro
                165                 170                 175
Gly Ile Ser Gly Gly Gly Gly Ile Leu Asp Ser Met Gly Ala Thr
                180                 185                 190
Thr Thr Glu Asn Pro Leu Gln Lys Ile Asp Ala Ala Leu Ala Gln Val
        195                 200                 205
Asp Thr Leu Arg Ser Asp Leu Gly Ala Val Gln Asn Arg Phe Asn Ser
        210                 215                 220
Ala Ile Thr Asn Leu Gly Asn Thr Val Asn Asn Leu Thr Ser Ala Arg
225                 230                 235                 240
Ser Arg Ile Glu Asp Ser Asp Tyr Ala Thr Glu Val Ser Asn Met Ser
                245                 250                 255
Arg Ala Gln Ile Leu Gln Gln Ala Gly Thr Ser Val Leu Ala Gln Ala
                260                 265                 270
Asn Gln Val Pro Gln Asn Val Leu Ser Leu Leu Arg
                275                 280

<210> SEQ ID NO 10
<211> LENGTH: 9
<212> TYPE: PRT
<213> ORGANISM: Homo sapiens

<400> SEQUENCE: 10

Lys Ile Phe Gly Ser Leu Ala Phe Leu
1               5

<210> SEQ ID NO 11
<211> LENGTH: 10
<212> TYPE: PRT
<213> ORGANISM: Homo sapiens

<400> SEQUENCE: 11

Val Leu Gln Gly Leu Pro Arg Glu Tyr Val
1               5                   10
```